(12) United States Patent
Soto et al.

(10) Patent No.: US 7,853,456 B2
(45) Date of Patent: Dec. 14, 2010

(54) SYSTEMS AND METHODS FOR RISK STRATIFICATION OF PATIENT POPULATIONS

(75) Inventors: Gabriel Enrique Soto, Chesterfield, MO (US); John Albert Spertus, Kansas City, MO (US)

(73) Assignee: Health Outcomes Sciences, LLC, Los Angeles, CA (US)

( * ) Notice: Subject to any disclaimer, the term of this patent is extended or adjusted under 35 U.S.C. 154(b) by 1602 days.

(21) Appl. No.: 11/072,053

(22) Filed: Mar. 4, 2005

(65) Prior Publication Data

US 2005/0203773 A1 Sep. 15, 2005

Related U.S. Application Data

(60) Provisional application No. 60/550,763, filed on Mar. 5, 2004, provisional application No. 60/554,700, filed on Mar. 19, 2004.

(51) Int. Cl.
*G06Q 10/00* (2006.01)
*G06F 7/60* (2006.01)
*G06F 9/45* (2006.01)
*G06F 19/00* (2006.01)
*G06G 7/58* (2006.01)
*A61B 5/00* (2006.01)

(52) U.S. Cl. .................... 705/2; 703/2; 703/11; 703/22; 705/3

(58) Field of Classification Search ...... 705/2, 705/3, 4
See application file for complete search history.

(56) References Cited

U.S. PATENT DOCUMENTS

| 4,846,190 A | 7/1989 | John |
| 5,517,405 A | 5/1996 | McAndrew et al. |
| 5,860,917 A * | 1/1999 | Comanor et al. ............ 600/300 |
| 6,120,460 A | 9/2000 | Abreu |
| 6,333,160 B1 | 12/2001 | Tamura |
| 6,385,589 B1 | 5/2002 | Trusheim et al. |
| 7,081,347 B2 | 7/2006 | Yusuf et al. |

(Continued)

FOREIGN PATENT DOCUMENTS

WO WO 03/104939 A2 12/2003

(Continued)

OTHER PUBLICATIONS

Reference A—StatSoft (http://www.statsoft.com/TEXTBOOK/stglz.html).*

(Continued)

*Primary Examiner*—Robert W Morgan
*Assistant Examiner*—Sean K Hunter
(74) *Attorney, Agent, or Firm*—Knobbe, Martens, Olson & Bear LLP

(57) ABSTRACT

A statistical processing system includes a server operably configured with program instructions implementing a plurality of statistical models to at least one of (a) predict a health outcome based on questionnaire responses, (b) assist a patient's choice of therapeutic modality based on questionnaire responses, and (c) assess a health risk or status based on questionnaire responses. Also provided is a research agency communicating with the server and contracted to provide the statistical models using a visual interface communicated by the server. The server is configured to analyze requests received from users relating to a plurality of said statistical models to reduce redundancy in requests for patient data.

71 Claims, 33 Drawing Sheets

U.S. PATENT DOCUMENTS

| | | | |
|---|---|---|---|
| 7,134,994 | B2 | 11/2006 | Alpert et al. |
| 7,187,992 | B2 | 3/2007 | Tuszynski |
| 7,643,969 | B2 | 1/2010 | Soto et al. |
| 2002/0165855 | A1 | 11/2002 | Ohtomo |
| 2003/0229513 | A1 | 12/2003 | Spertus |
| 2004/0172291 | A1* | 9/2004 | Knowlton ............ 705/2 |

FOREIGN PATENT DOCUMENTS

| | | | |
|---|---|---|---|
| WO | WO 03/104939 | A3 | 12/2003 |
| WO | WO03104939 | * | 12/2003 |

OTHER PUBLICATIONS

Rabin, D. S.; Qadeer; U.; Steir, V.E. "A Cost and Outcome Model of Fertility Treatment in a Managed Care Environment." Fertility & Sterility 1996, 66, 896-903.

"Virtual Offices Basic Manual for Professional" by Help Horizons. com v1.14, Apr. 2001, 60 pages.

Office Action (U.S. Appl. No. 10/165,855), date mailed: Apr. 18, 2006.

Office Action (U.S. Appl. No. 10/165,855), date mailed: Nov. 17, 2006.

Office Action (U.S. Appl. No. 10/165,855), date mailed: Jan. 30, 2008.

Office Action (U.S. Appl. No. 10/165,855), date mailed: Aug. 25, 2008.

Office Action (U.S. Appl. No. 11/072,209), date mailed: Mar. 19, 2008.

Office Action (U.S. Appl. No. 11/072,209), date mailed: Oct. 16, 2008.

Office Action (U.S. Appl. No. 11/072,209), date mailed: Apr. 22, 2009.

U.S. Appl. No. 12/620,985, filed Nov. 18, 2009, Soto, et al.

John Spertus, et al.; Health Status Predicts Long-Term Outcome in Outpatients with Coronary Disease; Circulation—Journal of the American Heart Association; Jul. 2, 2002; pp. 43-49.

Colleen A. McHorney, et al.; The MOS 36-Item Short-Form Health Survey (SF-36): II. Psychometric and Clinical Tests of Validity in Measuring Physical and Mental Health Constructs; Medical Care; 1993; pp. 247-263; vol. 31-No. 3; J.B. Lippincott Company.

T A Rockall, et al.; Risk Assessment After Acute Upper Gastrointestinal Haemorrhage; Gut; 1996; pp. 316-321; vol. 38.

Ga L' Abbate, et al.; On-Line Integration and Analysis of Cardiological Data to Support Medical Decision Making; IEEE; Computers in Cardiology; 2004; pp. 189-192; vol. 31.

Elizabeth R. Delong, et al.; Comparing the Areas Under Two or More Correlated Receiver Operating Characteristic Curves: A Nonparametric Approach; Biometrics; Sep. 1988; pp. 837-845; vol. 44.

William A. Knaus, et al.; APACHE II: A Severity of Disease Classification System; Critical Care Medicine; Oct. 1985; pp. 818-829; vol. 13-No. 10; The Williams & Wilkins Co.

Frederic D. Wolinsky, et al.; Perceived Health Status and Morality Among Older Men and Women; Journal of Gerontology; 1992; pp. S304-S312; vol. 47-No. 6.

Philip S. Wells, et al.; Accuracy of Clinical Assessment of Deep-Vein Thrombosis; The Lancet; May 27, 1995; pp. 1326-1330; vol. 345.

Salim Yusuf, et al.; Effect of Coronary Artery Bypass Graft Surgery on Survival: Overview of 10-year results from Randomised Trials by the Coronary Artery Bypass Graft Surgery Trialists Collaboration; The Lancet; Aug. 27, 1997; pp. 563-570; vol. 344.

Peter C. Block, et al.; Identification of Variables Needed to Risk Adjust Outcomes of Coronary Interventions: Evidence-Based Guidelines for Efficient Data Collection; JACC; Jul. 1998: pp. 275-282: vol. 32-No. 1: Elsevier Science Inc.

Robert H. Jones, et al.; Identification of Preoperative Variables Needed for Risk Adjustment of Short-Term Mortality after Coronary Artery Bypass Graft Surgery; JACC; Nov. 15, 1996; pp. 1478-1487; vol. 28-No. 6; Elsevier Science Inc.

Robert M. Califf, et al.; Importance of Clinical Measures of Ischemia on the Prognosis of Patients with Documents Coronary Artery Disease; JACC; Jan. 1988; pp. 20-26; vol. 11-No. 1; Elsevier Science Inc.

John S. Rumsfeld, et al.; Health-Related Quality of Life as a Predictor of Mortality Following Coronary Artery Bypass Graft Surgery; JAMA; Apr. 14, 1999; pp. 1298-1303; vol. 281-No. 14.

Susan Gross Fisher, et al.; Mortality Ascertainment in the Veteran Population: Alternatives to the National Death Index; American Journal of Epidemiology; 1995; vol. 141-No. 3; The Johns Hopkins University School of Hygiene and Public Health.

John Spertus, et al.; Association Between Depression and Worse Disease-Specific Functional Status in Outpatient with Coronary Artery Disease; American Heart Journal; Jul. 2000; pp. 105-110; vol. 140-No. 1.

John A. Spertus, et al.; Monitoring the Quality of Life in Patients with Coronary Artery Disease; The American Journal of Cardiology; Dec. 15, 1994; 1240-1244; vol. 74.

John A. Spertus, et al.; Development and Evaluation of the Seattle Angina Questionnaire: A New Functional Status Measure for Coronary Artery Disease; JACC; Feb. 1995; pp. 333-341; vol. 25-No. 2; American College of Cardiology.

Ge Soto, et al; PRISM™: A Web-Based Framework for Deploying Predictive Clinical Models; Computers in Cardiology; Nov. 2004; pp. 193-196; vol. 31; IEEE.

Eric L. Eisenstein, et al.; Assessing the Clinical and Economic Burden of Coronary Artery Disease: 1986-1998; Medical Care; Nov. 8, 2001; pp. 824-835; vol. 39-No. 8; Lippincott Williams & Wilkins, Inc.

William Cassidy; http://archive.gamespy.com/halloffame/september02/pcs/; Pinball Construction Set; Bill Budge and Electronic Arts; 4 sheets.

Charles Hu, et al.; http://www.medcacl.com/heartrisk.html; Coronary Heart Disease Risk Calculator; Jan. 15, 2000; 1 sheet.

Visiontree; various pages from http://www.idegomethodologies.com; 2004; Idego Methodologies; 19 sheets.

Gabriel E. Soto, et al.; PRISM: A Novel Tool for Deploying Predictive Clinical Models; Circulation; May 25, 2004; p. 47; vol. 109-No. 20.

Gabriel E. Soto, et al.; PRISM Update: Experiences Using a Web-based Framework for the Deployment of Predictive Clinical Models at the Point of Care; Poster Presentations e341.

* cited by examiner

Model Details
_____

General Information:
_____

Name: | Angina Symptoms at One Year (Angioplasty/Stent) |

Outcome: | Probability of Having Angina Symptoms at One Year ▼ |

Description: | This model predicts the probability of having angina symptoms at one year for patients undergoing a percutaneous intervention for their coronary artery disease. Data for the model is derived from 1199 subjects participating in INFORM, a registry of Acute Coronary Syndrome (ACS) patients at the Mid America Heart Institute and Truman Medical Center (Kansas City, MO). |

Model Type: | Generalized Linear ▼ |

Version: | 1.0.0 |

Build Status:  In Progress

Active: ☑

Publish: ☑

Fig. 27A

Model Structure:

Link Function: [Logit ▼]  Linear Predictor $\eta$:

Inference: [Population ▼]  $\eta = \beta_0 + \beta_1 X_{\tau-1} + \ldots + \beta_\eta X_{\tau-\eta}$ Intercept Term(s): [✓]  Where coefficients $\beta_0, \ldots, \beta_\eta$
and terms $X_{\tau-1}, \ldots, X_{\tau-\eta}$ Error Parameterization: [✓]  are defined below. Estimator $\mu$:

$$\mu = (1+e^{-\eta})^{-1}$$

Output Plot Options:

Plot Label: [Angioplasty]

Condensed Plot Label: [PCI]  *(For mobile devices)*

Model Parameters: ($X_1, X_2, \ldots, X_N$)  [Edit List]

| Name | Category | Type |
|---|---|---|
| Age | Demographics | Continuous |
| Angina | Patient Characteristics | Nominal |
| AvoidCare | Patient Characteristics | Nominal |
| LungDisease | Comorbidities | Binary |
| SF12PCS | Clinical Characteristics | Continuous |

Parameter Transformations: ($X_K \rightarrow X_{T-1}, X_{T-2}, \ldots$)  [Add New Transformation]

| Name | Parameter | Type | |
|---|---|---|---|
| Age | Age | Identity | [Edit] |
| Ang_IndR2 | Angina | Indicator | [Edit] |
| AvCr_IndR2 | AvoidCare | Indicator | [Edit] |
| LungDz | LungDisease | Identity | [Edit] |
| SF12PCS | SF12PCS | Identity | [Edit] |

Model Terms: ($X_{T-1}, X_{T-2}, \ldots, X_{T-N}$)  [Add New Term(s)]

Fig. 27B

| Name | Description | Degenerate | | |
|---|---|---|---|---|
| Angin_i1 | 1 if Angina r=1; 0 otherwise | ☑ | ↑↓ | [Edit] |
| Angin_i2 | 1 if Angina r=2; 0 otherwise | ☑ | ↑↓ | [Edit] |
| Avoid_i1 | 1 if AvoidCare r=1; 0 otherwise | ☑ | ↑↓ | [Edit] |
| Avoid_i2 | 1 if AvoidCare r=2; 0 otherwise | ☑ | ↑↓ | [Edit] |
| Age_ID | Age | ☑ | ↑↓ | [Edit] |
| LungD_ID | LungDisease[0/1] | ☑ | ↑↓ | [Edit] |
| SF12P_ID | SF12PCS | ☑ | ↑↓ | [Edit] |

Coefficient Vector: $(\beta_0, \beta_1, ..., \beta_\eta)$  ▶ Import

| Intercept $(\beta_0)$ | Angin_i1 $(\beta_1)$ | Avoid_i1 $(\beta_2)$ |
|---|---|---|
| 0.5946918691 | 0.4675835737 | 0.87075678 |

| Age_ID $(\beta_3)$ | LungD_ID $(\beta_4)$ | SF12P_ID $(\beta_5)$ |
|---|---|---|
| -0.020630729 | 1.0356287352 | -0.026204752 |

Error Parameterization: *(Required for computing confidence intervals)*

Covariance Matrix:  ▶ Import

| | Intercept $(c_0)$ | Angin_i1 $(c_1)$ | Avoid_i1 $(c_2)$ | Age_ID $(c_3)$ | LungD_ID $(c_4)$ |
|---|---|---|---|---|---|
| Intercept $(c_0)$ | 0.456042215 | -0.117099971 | -0.042157233 | -0.003534012 | -0.0187443 |
| Angin_i1 $(c_1)$ | -0.117099971 | 0.1138507627 | 0.0072959287 | -0.000009428 | 0.00306582 |
| Avoid_i1 $(c_2)$ | -0.042157233 | 0.0072959287 | 0.048365083 | 0.0003534514 | 0.00014297 |
| Age_ID $(c_3)$ | -0.003534012 | -0.000009428331 | 0.0003534514 | 0.0000506005 | -0.0000140 |
| LungD_ID $(c_4)$ | -0.018744335 | 0.0030658202 | 0.0001429759 | -0.000014042 | 0.06492194 |
| SF12P_ID $(c_5)$ | -0.002432639 | 0.0001835103 | 0.0001659837 | 0.000007332421 | 0.00025297 |

NOTE: Values below the diagonal will be refreshed on 'Update'

Update    Delete this model    Cancel

Fig. 27C

Edit Outcome Definition

General Information:

Name: New Outcome
Outcome: One Year Outcomes (INFORM)
Description: Test outcome
Type: Survival
Active Status: ☐

Output Plot Options:

Output Styles:
- Solid Bar
- Digital
  Op1: 06 (75,85)
  Op2: 61 (57,64)
  Op3: 50 (40,53)

Caption: Test
Subtitle:
Minimum Value: 0
Maximum Value: 1
Scale Factor: 1
Use Custom Axis Labels: ☐
Use Scale Annotations: ☐

Custom Reports:                    [Add New Report]

Report Name                         [Edit]
Test report

Update    Delete this outcome    Cancel

Fig. 28

Edit Parameter Definition

General Information:

Name: Angina

Category: Patient Characteristics ▼

Description: Assessment of Angina Frequency. This question is derived from the Seattle Angina Questionnaire (Item number 4).

Type: Nominal ▼

Active Status: ■

Rendering/Collection Details:

Full Text: Over the past four weeks, have you had any chest pain, chest tightness or angina, or taken nitroglycerin (tablets or spray) for these symptoms?

Short Text: Angina within 4 weeks

Responses:

| | Item | Full Text | Condensed | [Add Response] |
|---|---|---|---|---|
| ✏ ☒ | 1 | Yes | Y | |
| ✏ ☒ | 2 | No | N | |

Report Name                                    [Edit]
Test report

Update    Delete this outcome    Cancel

Fig. 29

Home ClinicalTools Workgroup Discussions About ManageLibraries ManagePortal
Manage Account | Logoff Outcome Models No patient selected.                                    Select Patient Category: [All ▼]                                    Select All: ☑

---

☑ ⊞  Angina Symptoms at One Year (Angioplasty/Stent)

☑ ⊞  Angina Symptoms at One Year (Bypass Surgery)

☑ ⊞  Angina Symptoms at One Year (Medical Management)

☑ ⊞  In-Hospital Mortality for AMI in NSTEMI Patients

☑ ⊞  In-Hospital Mortality for AMI in STEMI Patients

---

Page 1 of 4                                    View: 5 | 10 | 15 | 20 | 25
[ << Previous Page] [Next Page >>]

---

To run one or more of the above models, simply follow these three steps:

● Click 'Select Patient' to use an existing record or to add a new patient.

● Place a check by the model(s) you wish to run.

◉ Click to 'Run Selected Model(s)'.

Fig. 31

Please complete all of the requested items below:

| | | |
|---|---|---|
| 1. | Age (years): | 55 |
| 2. | Gender: | |
| | ◉ Male | |
| | ○ Female | |
| 3. | History of Diabetes: | ☑ |
| 4. | History of Renal Failure: | ☐ |
| 5. | History of Recent Heart Failure: | ☐ |
| 6. | History of Prior PCI: | ☐ |
| 7. | History of Chronic Lung Disease: | ☑ |
| 8. | History of Cerebrovascular Disease: | ☐ |
| 9. | History of Peripheral Vascular Disease: | ☐ |
| 10. | LV Ejection Fraction: | 0.7 |
| 11. | NYHA Class II - IV: | ☐ |
| 12. | Non-elective PCI: | ☐ |
| 13. | Shock at the Time of PCI: | ☑ |
| 14. | Left Main Coronary Artery Lesion: | ☐ |
| 15. | Proximal LAD Coronary Artery Lesion: | ☐ |
| 16. | AHA Lesion Type: | |
| | ○ Low Risk (Type A) | |
| | ◉ Moderate Risk (Type B) | |
| | ○ High Risk (Type C) | |
| 17. | Graft Treated: | ☑ |

Fig. 32

SYSTEMS AND METHODS FOR RISK STRATIFICATION OF PATIENT POPULATIONS

CROSS REFERENCE TO RELATED APPLICATIONS

This application claims benefit of priority to provisional patent application Ser. No. 60/550,763 filed Mar. 5, 2004, and to provisional patent application Ser. No. 60/554,700, filed Mar. 19, 2004, both of which are hereby incorporated by reference in their entirety.

BACKGROUND OF THE INVENTION

The invention relates to methods and systems that provide computerized health care management, and more specifically, to methods and systems providing statistical assessment and prognostic information for individuals.

This application hereby incorporates by reference in its entirety another application filed on even date by the same inventors as and entitled "Methods and Apparatus for Providing Decision Support."

The past decade of health services research has witnessed an explosion of prognostic models to help physicians understand the risks and benefits of proposed medical therapies. However, the application of such models to clinical practice has been limited by both their complexity and the lack of a practical mechanism for making them available at the time of medical decision-making.

Furthermore, both the patient and the attending health care professional should be involved in making clinical health care treatment decisions that affect the patient's desired heath goals and quality of life concerns. These decisions may vary depending upon the patient's age, sex, socioeconomic, demographic and clinical characteristics, genetic, proteomic and biomarker parameters. The factors affect the relative risk and successfulness of outcomes of medical and surgical procedures and are referred to in the art by the term "clinical data."

One goal of medical care is to make treatment recommendations to patients commensurate with their goals and values. To achieve this goal, one must describe the risks and benefits of a treatment that are relevant to a unique constellation of comorbidities and function of each particular patient. Several known risk-stratification models exist for diseases ranging from coronary artery disease to deep venous thrombosis to mortality from a gastrointestinal hemorrhage, e.g., as reported in Knaus W A et al., APACHEII: a severity of disease classification system. Critical Care Medicine 13(10) 818-29 (1985, October) (a model for ICU patients); Wells PS et al., Accuracy of clinical assessment of deep-vein thrombosis. Lancet. 345:1326-30 (1995) (a score for the probability of deep vein thrombosis); Rockall TA et al., Risk assessment after acute upper gastrointestinal haemorrhage. Gut 38:316-21 (1996). Currently, these models remain largely academic and without a practical method or mechanism for being used in routine clinical care.

Computerized expert systems process information that usually correspond to rules or procedures that are applied by human experts to solve similar problems. One example of an expert system in the health care field is described in U.S. Pat. No. 5,517,405 to McAndrew et al. This system prompts users with questions directed towards a particular medical condition or symptom. The system consults a database or library to dynamically generate queries on the basis of user responses. Ultimately, the system provides a diagnosis together with a recommendation for a medical procedure or other treatment.

Another example of an expert system in the health care field is described in U.S. Pat. No. 6,385,589 to Trusheim et al. The system described therein accepts input from data sources that target identification of a "medical event." The data sources include laboratory data confirming a disease diagnosis, pharmacy benefits manager data, hospital admissions data, physician records, home health care data, and health insurance data. The system described by Trusheim et al. also provides member characterization data, which is compiled using member surveys, care provider data, insurance claim data, and historical health care data. The system uses a combination of member characteristics and medical event data to identify risk situations, such as diabetes, hypertension, dementia, unmedicated heart conditions, and discharge of elderly patients with no caregiver support. Although member survey responses may be used in making these risk assessments, Trusheim et al. does not appear to use the survey responses to identify the nature and extent of risk in terms of a statistical risk assessment. For example, a condition may be diagnosed in which an elderly person has been discharged with no caregiver, but without any assessment of whether the discharge poses mild or severe health status risk. Proactive follow-ups after identification of a risk situation are left to a medical care provider who assesses the patient.

Other known methods for evaluating and risk-stratifying patients to (for example) identify those with the greatest likelihood of future coronary conditions include exercise treadmill tests, nuclear stress tests, and stress echocardiography. Once these tests identify patients with an adverse prognosis, further risk-stratifying patients are expensive and, in some cases, invasive. Additionally, the results from such tests can require several days for a trained technician or statistician to process and there is no clear mechanism for integrating the data in statistical models to better refine risk or to determine how such risk may vary as a function of alternative treatment strategies. Most importantly, the subsequent outcomes of alternative treatment strategies for a given risk profile are neither generated nor presented.

The following references are provided for background purposes and are specifically incorporated herein by reference, as are any and all other references cited herein, including patents and patent applications:

1. Yusuf S, Zucker D, Peduzzi P, Fisher L D, Takaro T, Kennedy J W, Davis K, Killip T, Passamani E, Norris R, et al. Effect of coronary artery bypass graft surgery on survival: overview of 10-year results from randomised trials by the Coronary Artery Bypass Graft Surgery Trialists Collaboration. *Lancet.* 1994; 344:563-70.
2. Spertus J, McDonell M, Fihn S. Association between depression and worse disease-specific functional status in outpatients with coronary artery disease. *Am Heart J.* 2000; 140:105-110.
3. Spertus J A, Winder J A, Dewhurst T A, Deyo R A, Fihn S D. Monitoring the quality of life in patients with coronary artery disease. *Am J Cardiol.* 1994; 74:1240-1244.
4. Spertus J A, Winder J A, Dewhurst T A, Deyo R A, Prodzinski J, McDonell M, Fihn S D. Development and evaluation of the Seattle Angina Questionnaire: A new functional status measure for coronary artery disease. *J Am Coll Cardiol.* 1995; 25:333-341.
5. McHorney C A, Ware J E, Jr., Raczek A E. The MOS 36-Item Short-Form Health Survey (SF-36): II. Psychometric and clinical tests of validity in measuring physical and mental health constructs. *Med Care.* 1993; 31:247-63.
6. Fisher S G, Weber L, Goldberg J, Davis F. Mortality ascertainment in the veteran population: alternatives to the National Death Index. *Am J Epidemiol.* 1995; 141:242-50.

7. Jones R H, Hannan E L, Hammermeister K E, Delong E R, O'Connor G T, Luepker R V, Parsonnet V, Pryor D B. Identification of preoperative variables needed for risk adjustment of short-term mortality after coronary artery bypass graft surgery. The Working Group Panel on the Cooperative CABG Database Project. *J Am Coll Cardiol.* 1996; 28:1478-1487.
8. Block P C, Peterson E C, Krone R, Kesler K, Hannan E, O'Connor G T, Detre K. Identification of variables needed to risk adjust outcomes of coronary interventions: evidence-based guidelines for efficient data collection. *J Am Coll Cardiol.* 1998; 32:275-82.
9. Wolinsky F D, Johnson R J. Perceived health status and mortality among older men and women. *J Gerontol.* 1992; 47:S304-12.
10. Rumsfeld J S, MaWhinney S, McCarthy M, Jr., Shroyer A L, VillaNueva C B, O'Brien M, Moritz T E, Henderson W G, Grover F L, Sethi G K, Hammermeister K E. Health-related quality of life as a predictor of mortality following coronary artery bypass graft surgery. Participants of the Department of Veterans Affairs Cooperative Study Group on Processes, Structures, and Outcomes of Care in Cardiac Surgery. *JAMA.* 1999; 281:1298-303.
11. Califf R M, Mark D B, Harrell F E, Jr., Hlatky M A, Lee K L, Rosati R A, Pryor D B. Importance of clinical measures of ischemia in the prognosis of patients with documented coronary artery disease. *J Am Coll Cardiol.* 1988; 11:20-6.
12. Eisenstein E L, Shaw L K, Anstrom K J, Nelson C L, Hakim Z, Hasselblad V, Mark D B. Assessing the clinical and economic burden of coronary artery disease: 1986-1998. *Med Care.* 2001; 39:824-35.

BRIEF DESCRIPTION OF THE INVENTION

Some aspects of the present invention provide a method for supplying information. This method includes operating, or contracting with an agent to operate a server to communicate via one or more networks with at least one of a research agency or an intermediary agency. The method further includes contracting with the research agency for the research agency to supply to the server, via at least one of the networks, statistical models each using one or more parameters, wherein the models are configured to determine statistical outcomes of at least one course of procedure or of non-treatment, or risks of developing a pathological condition later in life. (By way of example only, and not by way of limitation, the latter, when provided, might include a 10-year risk of developing CAD or another condition, based on, for example, genetic and other clinical factors). The method further includes contracting with the intermediary agency for the intermediary agency to receive, on request from the intermediary agency via at least one of the networks, parameter lists with reduced redundancy sufficient to apply the requested statistical models to produce model results and with default values of parameters when such default values are available, to receive and reformat the parameter lists and default values, when available, for transmission to end users or their agents as queries, to transmit information received in response to the queries to the server for processing in the requested models, to receive statistical results from the models, and to reformat the results and transmit the reformatted results to the end users or their agents.

In another aspect, the present invention provides a method for risk-stratifying individual patients. In this aspect, the method includes contracting with a research agency for the research agency to create statistical health models configured to provide model results including patient risk assessments using health query responses, health parameter data, or both. In addition, the method includes operating a server to store instructions to receive requests to use the models, to distribute requests for data used by the models, and to apply a redundancy reduction procedure to the requests for data when a plurality of models are requested that pertain to a single patient, to analyze data received in response to the requests. The method further includes transmitting results from the analysis, and contracting with an intermediary agency for the intermediary agency to receive model requests from users, to transmit the model requests to the server use the stored instructions relating to the model, and to disseminate reduced redundancy requests for data relating to requested models. The intermediary agency is also contracted to transmit data received in response to the data requests to the server, to receive the transmitted results from the analysis, and to format the results from the analysis for transmission to users.

In yet another aspect, the present invention provides a statistical processing system. The statistical processing system includes a server operably configured with program instructions implementing a plurality of statistical models to at least one of (a) predict a health outcome based on questionnaire responses or other data inputs relevant to a particular patient, (b) assist a patient's choice of therapeutic modality based on questionnaire responses or other relevant inputs, and (c) assess a health risk or status based on questionnaire responses and/or data inputs. Also provided is a research agency communicating with the server and contracted to provide the statistical models using a visual interface communicated by the server. The server is configured to analyze requests received from users relating to a plurality of said statistical models to reduce redundancy in requests for patient data.

In still another aspect, the present invention provides a method for supplying information. This method includes operating, or contracting with an agent to operate a server to communicate via one or more networks with a research agency and with either end users or their agents. The method further includes contracting with the research agency for the research agency to supply to the server, via at least one of the networks, statistical models each using one or more parameters, the models configured to determine statistical outcomes of at least one course of procedure or of non-treatment, or risks of developing a pathological condition later in life. Other steps in the method include receiving, via at least one of the networks, requests for use of the statistical models, constructing parameter lists with reduced redundancy sufficient to apply the requested statistical models to produce model results and with default values of parameters when such default values are available, transmitting the reduced redundancy parameter lists and default values, when available, to end users or their agents as queries, receiving information in response to the queries for processing in the requested models, and transmitting statistical results of the models to the end users or their agents.

In yet another aspect, the present invention provides a method for supplying information that includes operating, or contracting with an agent to operate a server to communicate via one or more networks including an intermediary agency and providing, in the server, statistical models each using one or more parameters, the models configured to determine statistical outcomes of at least one course of procedure or of non-treatment, or risks of developing a pathological condition later in life. The method also includes contracting with the intermediary agency for the intermediary agency to receive, on request from the intermediary agency via at least one of the networks, parameter lists with reduced redundancy sufficient to apply the requested statistical models to produce model results and with default values of parameters when such default values are available, to receive and reformat the parameter lists and default values, when available, for transmission to end users or their agents as queries, to transmit information received in response to the queries to the server for processing in the requested models, to receive statistical results from the models, and to reformat the results and transmit the reformatted results to the end users or their agents.

It will thus be appreciated that configurations of the present invention provide systems and methods for analyzing medical information by comparing the medical information against a statistically validated study to make an expert description or proactive recommendation in the form of a risk assessment. Methods and apparatus of the present invention have the capacity to rapidly disseminate assessments in a variety of formats and to be updatable as new information becomes available. Thus, some configurations of the present invention provide assurance that the most accurate models can be provided for use at all times. Information provided can be used by physicians and patients to make informed decisions, such that the risk associated with a medical procedure can be gauged relative to the potential benefit of performing the procedure. Therefore, configurations of the present invention can help maximize the potential benefit from a particular intervention procedure and allow selection of the best of several alternative procedures.

Furthermore, some configurations of the present invention facilitate rapid translation of evidenced-based predictive models into robust tools (for example, web-based tools) capable of providing visual representations of predicted outcomes. When used in a medical environment to provide outcome predictions at the point of patient care, some configurations of the present invention can be used to rapidly disseminate the newest knowledge to the clinical setting.

Moreover, outcomes researchers can use various configurations of the present invention to create powerful evidence-based tools that deliver decision support at the point of care for diagnostic workups and treatment selection. In the management of acute coronary syndromes (ACS), for example, physicians can get immediate probability estimates for outcomes such as survival, angina frequency, or physical limitation at one year for all possible treatment options, as well as risk-projections for procedural complications.

BRIEF DESCRIPTION OF THE DRAWINGS

FIG. 27 is an example of a display of a visual selection of parametric regression model forms.

FIG. 28 is an example of a display of an outcome type screen.

FIG. 29 is an example of a display of a parameter name screen.

FIG. 31 is an example of a display that provides a visual selection of previously stored models.

FIG. 32 is an example of a display requesting parameter data.

DETAILED DESCRIPTION OF THE INVENTION

Figure 1:
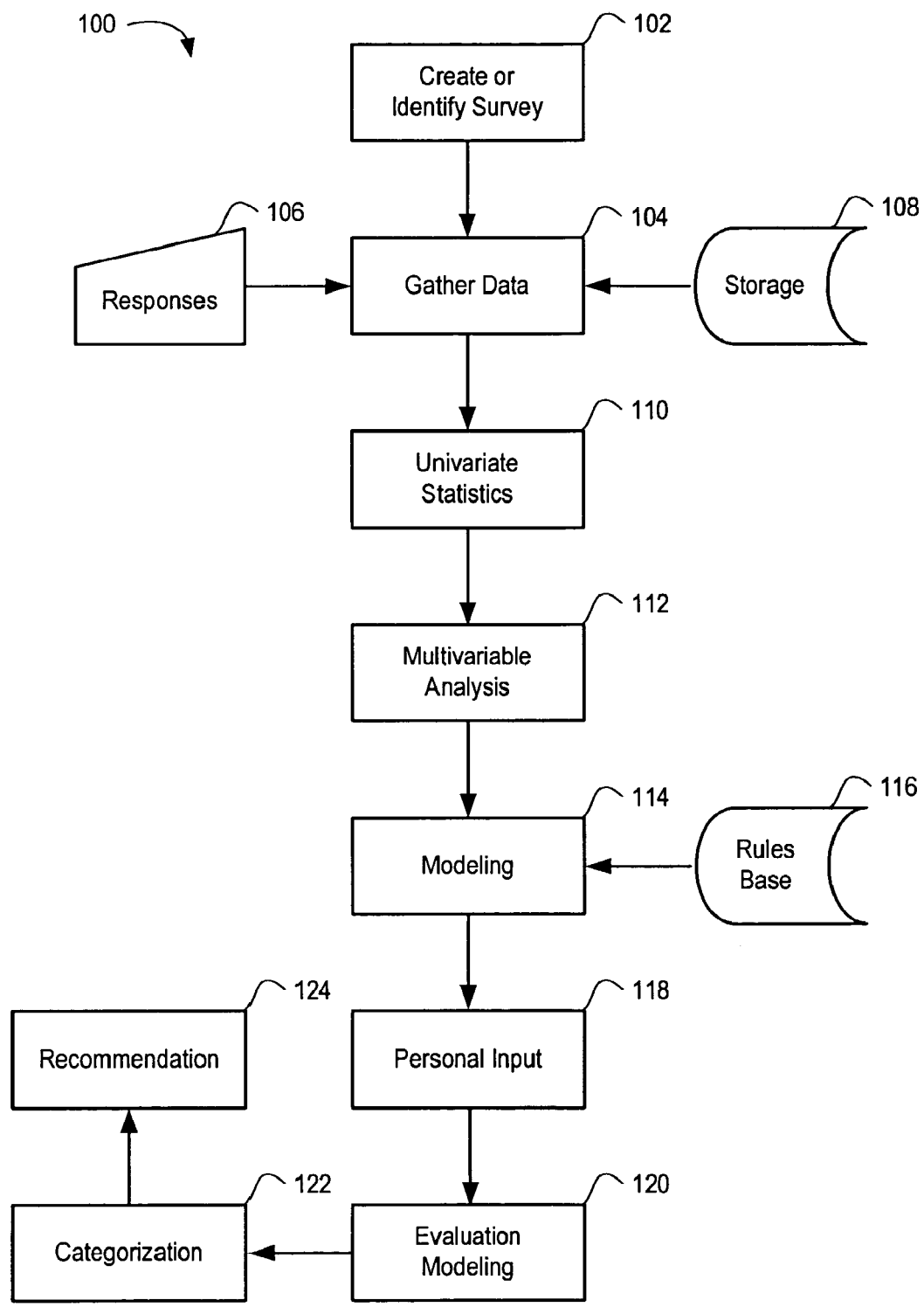
FIG. 1 is a process schematic diagram that illustrates the creation of a statistical model through the use of data collection and statistical processing, together with inversion and prognostic use of the statistical model in evaluating new responses.

Some configurations of the present invention provide a user-friendly architecture for a clinician to input patient data on an internet, mobile, or handheld computerized device. The device may be a remote device that is part of an intranet, internet, or both, and calculations may be performed on the remote device or on a server. Analysis of inputted data uses statistical models that may be downloaded from the internet, a CD, DVD, or other electronic medium or may be created by the user or by another entity via a guided process for formula construction. Statistical models may include linear, logistic, ordinal, cumulative logit, survival, and multinomial models. The results of the statistic analysis are displayed within minutes such that they may be used as a rapid clinical decision aid. Numerous display options allow clinicians and patients to choose how the results appear. For example, horizontal graphs, vertical graphs, side-by-side stacking plots, whisker plots, etc. are provided as user-selectable options.

Some configurations of the present invention integrate with existing information technology infrastructure. The multi-tiered architecture of some configurations includes presentation, application, and data layers, which are separately identifiable but interoperable. In some configurations, an application layer controls data collection, model execution, and portal site management. The data layer contains encrypted or otherwise protected data, in conformance with HIPAA regulations for the protection of health information.

The emergence of the internet and mobile computing devices has created new opportunities for researchers in the health care field to translate their evidenced-based predictive models into clinical decision aids. However, a number of barriers continue to prevent researchers from taking advantage of these technologies, including (1) the need for expertise in a computer programming language or application development environment; (2) the challenge of creating a system that can adapt to a broad range of clinical practice settings, each with unique workflow constraints; (3) the need for a sustainable mechanism for updating predictive models and deploying revisions in a timely fashion; (4) the difficulty of integrating with existing information technology (IT) infrastructures and disparate clinical information systems; and (5) the need to maintain the highest level of security for storing and transmitting protected health information (PHI) in accordance with HIPPA.

In an ideal world, outcomes researchers would have a pre-existing, technological framework in place that would allow them to rapidly translate their predictive models into clinical decision aids without having to invest significant personnel or financial resources. Researchers could use a visually-based interface for implementing prediction models and would have access to a full range of services for managing and deploying models across a broad range of devices in diverse health-care settings. The need for primary data entry on the part of clinicians and their staff would be minimized by built-in data storage capabilities as well as support for industry-standard protocols for exchanging health information with existing systems. These same data exchange mechanisms could also be used to provide web-based services that could go beyond clinical decision aids; for example, resource planning services that input whole population databases to project future disease prevalences and resource requirements.

In some configurations, a risk manager service is an application suite useful for building customizable web-based prediction tools that can be readily integrated into the workflow of patient care. Some configurations make use of Microsoft.NET framework and Microsoft Internet Information Services (IIS) and Microsoft SQL Server to create a robust multi-tier system that can deliver enterprise-level performance. However, configurations of the present invention are not limited to using any particular software company's software tools.

Some configurations of the present invention provide a web portal delivery system. A customizable portal engine delivers content to web-based clients. Page content in some configurations is authored using a built-in interface similar to that of a word processor, or the content can be edited directly as HTML or other appropriate mark-up language. A set of portal content modules includes, in some configurations, workgroup directories, discussion threads, and document repositories that allow outcomes research groups to create, manage, and build their own collective web sites.

Some configurations of the present invention provide a virtual prediction formula designer. An intuitive graphical user interface is provided that allows researchers to implement prediction formulae derived from standard statistical models. In many configurations, it is not necessary that researchers write software code directly. Instead, the configuration guides users through each phase of the formula construction process while supporting a range of statistical models. These models can include linear, logistic, cumulative logit, and multinomial models. Validation checks are used in some configurations to ensure the internal consistency of formulae before the formulae are published to the web either for direct us, use through an intermediary, or use via a handheld PDA or similar device.

Also, some configurations of the present invention provide a dynamic data collection system that individually customizes the necessary data input to the most parsimonious set of variables needed to conduct the requested analysis. A rendering engine creates data-input forms "on-the-fly." Collected data can be stored for subsequent retrieval, and data entry fields can be pre-populated with previously stored values in accordance with administratively defined data expiration policies.

In addition, some configurations of the present invention provide a graphical display of model output. Some configurations provide a plurality of graphical display options that are configured to help clinicians and patients understand model results and drive shared decision making. Examples include gradient-filled horizontal bar plots, solid-filled vertical bar plots, whisker plots, and "figuring" plots. Optional side-by-side stacking of plots provided in some configurations makes it easier to compare related outcomes (for example, expected results of different treatments for a particular condition) and allow display of relative treatment benefits derived from previously conducted randomized clinical trials. Customizable report templates are also provided in some configurations to allow such outputs to be configured into decision aids, informed consent documents, and patient educational materials.

Some configurations of the present invention provide cross-platform support. For example, support is provided for a plurality of platforms that may include Netscape, Internet Explorer, and mobile device support for WAP/WML and/or Pocket Browser devices. Thus, physicians can have access to predictive models in various clinical settings in which wired and/or wireless network service is available.

Some configurations provide a broad assortment of graphical output options that facilitate the sharing of information with patients, thereby allowing physicians and patients to reach a consensus decision regarding therapy that best meets the desires, needs, and expectations of the patient.

Enterprise-level performance is provided using a multi-tier application architecture that allows organizations to use high-performance servers such as IIS and Microsoft SQL Server for delivering web-content and managing data resources. Pages are constructed using dynamically-loaded controls that use configurable output caching. ADO.NET data access is implemented in some configurations using SQL stored procedures to increase performance and reduce network traffic. An XML-based configuration caches system-wide settings to reduce disk accession frequency during startup and operation.

Some configurations support both Microsoft WINDOWS® authentication using a domain/active directory and Forms-based authentication using a stored username/password. A role-based security infrastructure is used to maintain access control. Protected Health Information (PHI) is encrypted using dynamically generated ciphers (e.g., 128-bit minimum ciphers) that are unique to each user.

In some configurations, private and shared data management modes are provided to give authorized healthcare providers flexible access to patient information without compromising security. In private mode, each user can only access his or her own personal patient record set, whereas in shared mode, all authorized users can access a common patient record set. Some configurations also provide optional support for user aliasing. User aliasing allows individual physicians to create additional sets (for example, up to 10) of login credentials that map to their own account. This aliasing provides a convenient method for giving clinical support staff access to patient information while maintaining the ability to audit record access under a pre-existing role.

Also, some configurations provide XML web services that facilitate integration with existing IT infrastructures. These services allow healthcare organizations to rapidly link a patient database or databases created in configurations of the present invention with existing clinical information systems. For example, the link is provided over the Internet using industry standard protocols such as SOAP. Predictive tools are published in some configurations as a web service for automated model execution or as a service to third parties.

Some configurations of the present invention utilize a multi-tier application architecture wherein the presentation, application and/or data layers are separate but interoperable, allowing for a high degree of scalability, maintainability, and customization to meet the needs of an outcomes research group or healthcare organization.

The presentation layer in some configurations comprises web forms that utilize dynamically populated controls. These web forms are used to handle display and management of data for a user. Logic for model design and management, as well as data collection and model execution in some configurations, are handled by the application tier or layer. The application layer also provides business logic that is used for managing the portal site and associated web services, including, in some configurations, user and role management. Model definitions, patient information, portal content, and/or user information are stored in a server (for example, an SQL server database) that is access via stored procedures. These stored procedures are called from within a Microsoft.NET assembly in some configurations. Stored procedures provide a clean separation between the SQL database store and the middle-tier data access layer, thereby resulting not only in easier maintenance but also performance benefits since the procedures can be optimized the first time they are run and then retained in memory for subsequent calls.

In some configurations, role-based security and auditing procedures are built into the application and data layers. These security and auditing procedures are used to ensure that authenticated users can access only data for which they the users are authorized. Configuration settings in some configurations are stored in an XML file, including high level portal, tab, and module definitions. Additional performance gains are achieved in some configurations through caching of the portal settings, wherein settings are reloaded only if the configuration file has changed.

A general regression model framework is used for expressing predictions, encompassing various types of prognostic models including linear, logistic, ordinal, multinomial, and survival models. Models are serialized in some configurations of the present invention.

An outcomes researcher identifies parameters that go into a prediction formula. New parameters can be created de novo or selected from an existing parameter library. The use of parameter libraries permits standardization of parameter definitions across all models. Researchers can also set up shared libraries to facilitate collaboration with other groups on model implementations and data collection.

Once parameters have been defined, one or more data transformations are assigned to each. Examples of transformations include identity, polynomial, and "dummy-variable" transformations. Custom transformation types can also be defined in some configurations, to provide a broad range of complex formulae.

Main effects and interaction terms derived from the input parameters and their transformations are defined. In addition, regression coefficients are provided. These regression coefficients are used for calculating point estimates for an outcome of interest. Some configurations allow covariance estimates to be entered, as well. These covariance estimates are used for computing dynamically generatable confidence intervals.

Intuitive graphical user interfaces are provided in some configurations that guide model developers through formula construction and/or directly import formula definitions from an XML or other suitably formatted file using a predefined schema.

Once models have been constructed and published to the web via the portal, a built-in form rendering engine provided in some configurations of the present invention can be used to collect data elements required to run models. Some configurations also store collected data is in an internal database or piped to a data mapping service that readies the data for subsequent funneling into the specified model algorithm for execution. Results are then returned to the requesting client.

Scalability is provided in some configurations via a multi-tier application architecture. For example, server administrators can farm the front end of the portal across a number of servers while maintaining the ability to pull information from a single unique data store. Some configurations support all three modes of session state management currently implemented in .NET, allowing administrators to create dedicated state management servers for further performance gains under selected usage conditions or to support server farm configurations.

A modular architecture is used in some configurations of the present invention to provide extensibility. For example, some configurations are written entirely in C# and Transact-SQL, wherein business logic for performing a specific task or closely related tasks is encapsulated within a single code module. For example, a PortalModuleControl base class is provided for use by developers. Developers writing new modules can have these modules inherit this base class, which provides hooks that are used for the portal module to interact with the fundamental framework. Once created, administrators can readily integrate and manage new modules from within the administrative pages.

A code-behind-coding model is used in some configurations to maintain compatibility with Microsoft's Visual Studio.NET™ developer environment.

Some configurations of the present invention utilize both authentication and authorization to provide security. Authentication is a process by which the application verifies a user's identity and credentials. Authorization actually verifies the authenticated user's permissions for a requested resource.

A portal component is provided in some configurations that supports both Forms-based and Windows® authentication. When operated in the Forms-based authentication mode, configurations of the present invention store usernames and passwords within a database. When using the Windows® authentication, configurations of the present invention use a domain/active directory with NTLM challenge/response protocol to authenticate users.

Role-based security is used to provide authorization for the portal in some configuration of the present invention. Role based security determines whether or not a user has access to a particular resource. Users are grouped into various roles (for example, administrators, power users, users, etc.) and the role mappings are stored in the database. Resource access control is determined at the level of each portal tab and module. Redundant role checking is performed at the time of module initialization to prevent unauthorized access to administrative functionality. The patient database also employs redundant identity checking at the data access level to ensure that only authorized users can query or modify patient information. Some configurations provide an added measure of security by encrypting Protected Health Information (PHI) in the database using (for example) a system of dynamically generated 128-bit (minimum) ciphers that are unique to each user. All patient records belonging to a user are encrypted in some configurations using a unique set of ciphers so that other users or intruders cannot access the information.

Various configurations of the present invention translate complex risk stratification models and outcomes predictions to the interface of patient care. As such, medical decision-making and the quality of delivered care can be improved. Potential applications include decision support and shared decision making. Evidence-based tools can be built that deliver decision support at the point of care for diagnostic workups and treatment selection. For example, immediate probability estimates for specific diseases can be provided in order to select optimal diagnostic strategies for individual patients. Also, risks and outcomes can be estimated for patients considering one of several treatment options.

Visual representations of projected outcomes can be shared with patients to help them appreciate consequences of treatments, so that patients can select treatment options. Patients can thus be involved in selecting therapies most aligned with their individual goals and preferences.

Resource utilization can be improved using risk-stratification models deployed by various configurations of the present invention. Clinicians, nurses, and/or administrators can use the models to triage patients between different levels of care within a hospital or outpatient setting, while social workers and discharge teams can use the models to assess the need for additional social services at the time of discharge.

Customizable support templates are provided by some configurations of the present invention. These support templates can be used to generate "informed consent" documents that represent the anticipated risks and benefits of treatment, and individualize them to a specific patient.

Some configurations of the present invention create personalized informational brochures that can be used to educate patients about their disease condition and future prognosis. Outcomes associated with different lifestyle choices (e.g., exercise, smoking, etc.) can also be presented to help patients make more informed choices about their compliance with lifestyle or medication recommendations.

Web services provided in some configurations of the present invention can be used to pass entire databases spanning whole patient populations through models projecting future disease prevalences, treatment costs, resource requirements, or any other outcome of interest.

Some configurations of the present invention thus can improve the quality of medical decision making, reduce expenses related to incorrect or unnecessary tests or treatments, and empower patients to make informed decisions. Configurations of the present invention can also be useful for organizations monitoring national or global health threats. These organizations can use configurations of the present invention as a database for population studies, wherein demographic data may be accessed to monitor or predict the spread of disease.

Traditional use of medical information has been limited to clinical evaluation or similar studies indicating a present status in the progression of a disease, in quantifying the burden of disease, and disease-related impact on health related quality of life. Experts may use these data in making clinical assessments; however, the prognostic significance of a medical information score is traditionally unknown. Use of this information in prognostic fashion, according to the description below, facilitates systematic results that describe and evaluate a patient's medical information from new perspectives. Accordingly, physicians and patients can make better-informed decisions as to medical intervention, and the risks of intervention can now be quantitatively balanced against what the patient might expect if intervention does not occur.

The following discussion of processing medical information illustrates a particular embodiment in the field of cardiac health status information by way of example, not by limitation. The principles described below may be generally followed to produce analogous results in any field of health care for any disease or conditions.

FIG. 1 is a block diagram illustrating a general process 100 for practicing the aforementioned concepts. The process 100 may be implemented through the use of program instructions on a single computer, in a distributed processing environment, or with human intervention at respective illustrated steps. Step 102 entails the creation or identification of a survey designed to procure medical information, such as health status information, and possibly other information that may sometimes overlap with medical information, such as demographic information and clinical information. As a particular example of medical information, health status information means information that focuses upon a disease or medical condition as measured by symptomatology, physical effects (e.g., limited range of motion or lifting capability), or mental effects of the disease (e.g., depression or anxiety). The health status information may also monitor the effects of treatment. In these contexts, demographic data means descriptive information that could be used to characterize or classify a person in a statistically meaningful way, for example, age, smoking habits, income, geographic location, marital status, race, gender, military service, or drinking habits. Clinical information may include medical history information about the person or diagnostic test results from that person.

Particularly useful clinical information includes the identification of adverse outcomes, which are defined as a medical event that people normally wish to avoid. Adverse outcomes may include, for example, hospitalizations, death, onset of mental depression, and surgery. The clinical data may also include positive outcomes, such as five year cancer survival, cancer remission, or the effectiveness of a class of therapeutic modality in treating a disease.

A variety of health status questionnaires are available and generally known to medical practitioners. Many of these questionnaires have been validated by direct or indirect means to show that patient responses to the questionnaires bear some relationship in describing a present disease state or medical condition. Pre-existing questionnaires may be selected for use as the survey in step 102. This manner of selection accelerates the time required for completion of step 102. Alternatively, it is not necessary to use health status questionnaires, and any medical information may be applied for these purposes, e.g., laboratory test results, such as blood work, biopsy, endocrine tests; genetic tests, such as microarray testing for a variety of diseases or conditions; health screening tests; cancer tests; and physical examination findings.

A survey may be created in step 102 using research that identifies conditions, results, symptoms and/or descriptions of a medical disease or condition. This research is preferably completed by a medical expert as to the disease or medical condition. The questions may be prepared to present survey respondents with a variety of selectable options that are each assigned a score on a relative scale that indicates a relative severity of the disease or medical condition. The overall survey may be scored on the basis of accumulated scores from some or all answers to the questions. The questions may be scored on the basis of the overall score or subsets of questions addressing domains or categories of disease symptomatology, for example, domains of physical limitation, severity of symptomatology, frequency of symptomatology, quality of life, and satisfaction with treatment. The creation of surveys for purposes of using them according to the various instrumentalities and embodiments of the invention does not fundamentally differ from traditional techniques of producing these surveys or questionnaires.

In step 104, the survey that is created or identified in step 102 may be administered to a test study group of persons who provide responses 106. Administration may occur by using written or electronic instrumentalities. Additional data including clinical or demographic data may optionally be obtained from additional responses 106 or from electronic data storage 108, such as the database of a health insurance company, medical informatics company, medical hospital, or governmental agency.

The data-gathering step 104 may proceed over a period of time, such that the survey responses 106 may continually update throughout this period, with the initial response forming a baseline. The survey responses are scored by a suitable scoring system, and the data is subjected to statistical processing in steps 110 and 112. Univariate statistics may be calculated in step 110 to identify potentially significant predictors of future health states. The statistical results may, for example, relate health status information from the responses 106 to adverse outcomes and/or positive outcomes in the clinical data. The medical information may be used to stratify the outcomes into ranges. Still further, the statistical information may be related to outcomes over a period of time. Demographic data and clinical data may be used to correct outcomes for factors that are not directly related to the medical condition that is the focus of the medical information survey, such as by correcting overall mortality in a cardiac study for mortality arising from diabetes.

In step 114, the results of statistical calculations from steps 110 and 112 may be subjected to expert review, for example, review by medical and statistical experts in the field. The lessons gleaned from this review may be represented by program logic and stored in a rules base 116. Statistical correlations or algorithms may also be created for use in prognostic modeling. A particularly useful technique, for example, is the Kaplan-Meier method of relating a parameter to an adverse outcome over time. A plurality of Kaplan-Meier curves may, for example, represent stratified groupings of medical information. The statistical results may, for example, be related to health status information, demographic data, and/or clinical data through use of artificial intelligence or self-training algorithms, such as neural networks or adaptive filters. The result of step 116 may produce an inverted statistical model or rules that may be used to assess probabilities of outcomes on the basis of medical information.

In step 118, a person (such as a patient or other individual) may be administered a questionnaire that is identical, or at least statistically identical, to the survey that was created or identified in step 102. Additional surveys may be administered or other data sources may be used to obtain, as completely as possible from the person, an identical set of data in comparison to the data that was gathered from individuals in the test study group in step 104. Step 120 may include submitting the personal input data from step 118 for processing through the inverted model derived from step 114. The result of the evaluation modeling step 120 may be to assess the probabilities of outcomes on the basis of the person's medical information.

The results from step 120 may be categorized in step 122, e.g., by the use of delimiting values or rules-based score groupings, to select persons who are at a relatively greater or lower risk of having a particular outcome. In step 124, a recommendation may be generated, for example, that the person seek out a physician for treatment, or that the person may wish to consider one medical procedure over another.

The Seattle Angina Questionnaire (SAQ) is a well-known and widely-accepted health status questionnaire providing a disease-specific health status measure for patients with coronary artery disease; however, the questionnaire has not heretofore been shown to be a valid predictive tool. There will now be demonstrated, by way of example and not of limitation, a methodology according to the process 100 for relating health status measures to adverse outcomes, such as mortality, hospitalization and poor quality of life.

EXAMPLE 1

Survey Data Collection

Example 1 demonstrates data collection techniques for gathering data that were used as steps 102 and 104 of FIG. 1. In some cases, an expert devised questions to obtain data possibly having some relevancy in assessing prognostic outcomes. In other cases, a well-accepted study may be selected for this purpose.

A literature search identified the SAQ as a leading survey pertaining to health status of acute coronary syndromes (ACS) or coronary artery disease (CAD). A total of 5,558 Veteran's Administration patients reporting coronary artery disease were administered the SAQ. Patient responses to the SAQ were evaluated by conventional SAQ assessment techniques to provide scores assessing physical limitation characteristics according to traditional risk variables including physical limitation, angina stability, angina frequency, CAD-specific treatment satisfaction and quality of life. The patients were also asked to provide demographic information and medical history data. Selection of the SAQ for this example was made because the questionnaire is generally accepted to be a valid indicator of the status it was designed to measure, namely, patients' disease-specific physical limitations, angina stability, angina frequency, treatment satisfaction and quality of life. SAQ selection was also made because the SAQ is generally accepted as a valid clinical tool by the medical profession. The SAQ is a self-administered, disease specific measure for patients with coronary artery disease. The questionnaire is valid, reproducible, and sensitive to clinical change.

SAQ responses were obtained from a test study group of cardiac patients. The SAQ was scored to quantify the patients in a plurality of domains. The domains included physical limitations due to angina, the frequency and recent change in patient symptoms, patient satisfaction with treatment, and the degree to which patients perceive that disease has impacted their quality of life. The scores were transformed to assess the scores on a distribution across a range of 0 to 100, according to conventional SAQ methodology where higher scores indicate better status function, e.g., less physical limitation, less angina and better quality of life. The normalized scores from the test study group were divided into quartile ranges of increasing severity for ease of interpretation. The SAQ domains of this particular study included physical limitation, angina, and better quality of life.

Demographic or clinical data not directly linked to health status information was shown to have statistical significance in using health status data to assess outcomes including morbidity and ACS hospital admission. Data was collected from the survey respondents who were asked to provide information including:

gender;

race;

medical comorbidities arising from or related to previous hospitalization, cancer, chronic heartburn, depression, drug abuse, kidney problems, liver disease (yellow jaundice or hepatitis), post traumatic stress disorder, seizures or convulsions, peptic ulcer disease, and thyroid disease;

cardiac risk factors including diabetes, hypertension, and smoking history; and cardiovascular disease severity factors indicated by stroke, congestive heart failure (CHF), previous hospitalization for ACS, prior coronary revascularization procedure, and prior myocardial infarction (MI).

Additional demographic data was obtained using standard questionnaires that were also scored, such as the SF-36, as described in McHomey et al., The MOS-36 Item Short-form Health Survey (SF-36): II Psychometric and clinical test of validity in measuring physical and mental health constructs, Med. Care. 1193; 31:247-63.

Outcomes were tracked for each patient during a two-year course of study. The primary outcome was one-year mortality. Mortality was tracked using information provided by the Veteran's Administration. A second outcome tracked during the two-year course of the study was hospital admission for ACS.

EXAMPLE 2

Statistical Processing of Life Survey Data Collection

The data collected in Example 1 was subjected to statistical processing, e.g., as generally shown in steps 110 and 112 of FIG. 1 to create a model relating the respective adverse outcomes to scores on the SAQ. All analyses were performed using commercially available statistical computer programs, namely, SAS™ Version 6.12 (a trademark of SAS Institute, Inc. of Cary, N.C.) and S-Plus 2000™ for Windows (a trademark of Statistical Sciences, Inc., of Seattle, Wash.). Statistical curves for all cause mortality were calculated using Kaplan-Meier analysis. The data were stratified by quartiles of the initial or baseline SAQ scores. Log-rank tests were used to compare data from the respective groups to establish that patients with lower scores initially died sooner and more frequently than patients reporting higher scores. Predictive models were developed for one year mortality and ACS hospitalization, by logistic regression.

Three models were constructed for each of the adverse outcomes including mortality and hospitalization. The first model included only SAQ domain scores. The second model included only demographic data and clinical variables. In each case, the models were developed by incorporating predictors with significant univariate associations with outcome (probability value less than or equal to 0.1) and using backward elimination until all remaining factors were significant at the 0.1 level. Age was entered as a continuous predictor, and the remaining independent variables were categorical. A final model was developed by combining significant variables from the first two models to estimate the incremental prognostic value of the SAQ score above demographic and clinical characteristics alone. For all modes reported in Table 1, probability values and estimated odds ratios are presented.

Model calibration was assessed by comparing predicted and observed outcomes by deciles of predicted risk. Goodness of fit was determined by the Hosmer-Lameshow test. Discriminatory power was evaluated by use of c-statistics and compared by Mann-Whitney tests, as described in DeLong et al., Comparing the areas under two or more correlated receiver operating characteristic curves: a nonparametric approach. Biometrics, 1988; 44; 837-845. Model calibration and shrinkage were validated on 200 bootstrap resamples of the original data set, as described in Harrell et al., Multivariable prognostic models: issues in developing models, evaluating assumptions and adequacy, and measuring and reducing errors, Stat. Med. 1996; 15:361-387.

In fewer than 0.3% of the cases, baseline and clinical variables were missing from the input data. The missing baseline and clinical data was imputed to the mean or by random sampling of data. Nineteen percent of patients had missing SAQ scores because of incomplete questionnaires. The one year mortality for these patients was higher (7.5% versus 5.3) and the ACS hospital admission was lower (2.3% versus 3.6) than patients who filled out completed questionnaires. Primary analyses were performed on those with complete SAQ data. Supporting analyses were performed to determine the impact of missing data were conducted with multiple imputation techniques that conditioned upon the available SAQ and SF-36 scores, according to techniques described in Little et al., Statistical Analysis with Missing Data, New York, N.Y., Wiley; 1987. S-plus subroutines devel-

EXAMPLE 3

Univariate Calculation Results

The results of statistical calculations in Example 2 were inverted to provide a model for prognostic use. Table 1 provides the baseline characteristics and univariate odds ratios for one-year mortality and hospitalization. The mean SF-36 PCS was 30.8±10.5, indicating that these patients scored almost two standard deviations below the mean United States population in terms of general physical health status. Over the one year of observation, there were 238 deaths (5.3% of the test population) and 154 ACS hospital admissions (3.6% of the test population).

Table 1 describes the relative odds of death at one year by demographic characteristics, comorbidities, and SAQ scores. The most powerful predictive parameters were age, presence of congestive heart failure, and health status. In Table 1, the "Odds Ratio" for "One-Year Mortality" is calculated as the actual mortality divided by the "Minimal" mortality. The low p-values show that the reported modes are statistically valid predictors because the p-values are less than an arbitrary delimiting value, in this case less than 0.05. Thus, the "Odds Ratio" for the "Minimal" quartile is understood to be 1.0. A person in the "Severe" quartile is 6.2 times more likely to die than a person in the "Minimal" quartile. Table 1 provides a model for prognostic use because Table 1 may be used to relate a person's health status, demographic, or clinical information, with an outcome likelihood in the domain of mortality or ACS hospitalization. This is done, for example, by assessing the person's SAQ score as to physical limitation and entering Table 1 to determine the likelihood. This modeling capability may, for example, be performed through program instructions that apply an expert set of rules in reporting from a database.

Figure 2:
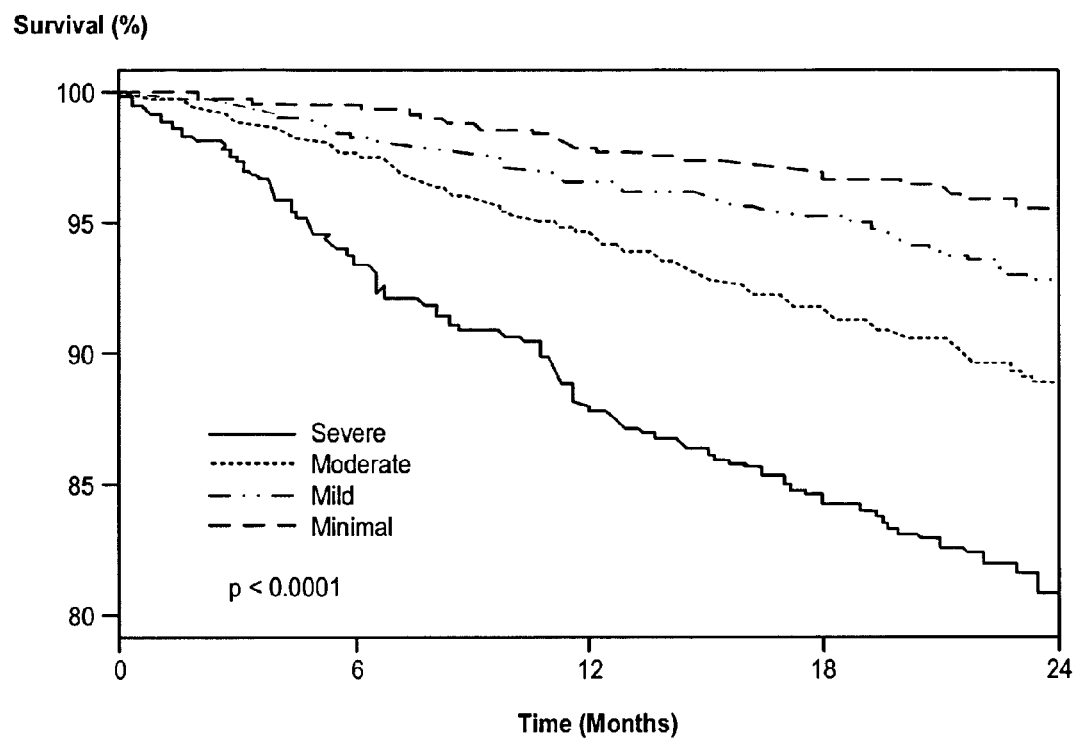
FIG. 2 shows a prognostic statistical model including Kaplan-Meier calculation results that demonstrate increasing mortality over time on the basis of Seattle Angina Questionnaire (SAQ) scores that have been stratified in quartiles of relative disease severity.

FIG. 2 shows the Kaplan-Meir survival curves over time for the SAQ physical limitation domain, which was broken out into quartiles representing severe (0-24), moderate (25-49), mild (50-74), and minimal (75 to 100) physical limitation. Separation of the curves, especially for those having the worst function, begins immediately and continues over the two-year period of observation. The mortality rates shown in FIG. 2 are the actual mortality rates, as opposed to the odds ratio shown in Table 1. Linear regression, such as a least squares technique, may be used to calculate an algorithm for each of the stratified domains to obtain a prognostic model on the basis of SAQ score.

As shown in Table 1, SAQ scores were divided into domains including physical limitation, angina stability, angina frequency, and quality of life.

Specifically, the SAQ was scored in a different manner for each domain to assess these parameters. The domains were divided into SAQ ranges. Table 1 also describes the odds of hospital admission for ACS. The strongest predictor of admission was a previous ACS-related hospitalization. The next most powerful predictors were SAQ angina frequency, physical limitation, and quality of life domains. For example, those reporting severe angina were 3.1 times more likely to be admitted to the hospital for ACS than those reporting minimal angina.

TABLE 1

BASELINE CHARACTERISTICS AND UNIVARIATE ODDS RATIOS

|  | n = 4,484 | One-Year Mortality Odds Ratio (95% CI) | p-value | One-Year ACS Admission Odds Ratio (95% CI) | p-value |
|---|---|---|---|---|---|
| Age (years)* | 67 ± 10 | 1.6 (1.4, 1.9) | <0.001 | 1.0 (0.8, 1.2) | 0.895 |
| Male | 4405 (98.3%) | 1.4 (0.5, 5.6) | 0.58 | N/A | 0.11 |
| Caucasian | 3697 (85.6%) | 1.1 (0.7, 1.6) | 0.71 | 1.0 (0.7, 1.6) | 0.97 |
| Prior hospitalization (any) | 720 (16.1%) | 1.7 (1.2, 2.3) | 0.001 | 4.6 (3.3, 6.4) | <0.001 |
| Prior hospitalization for ACS | 148 (3.3%) | 1.6 (0.8, 2.8) | 0.12 | 10.3 (6.6, 15.7) | <0.001 |
| Cancer | 612 (13.7%) | 1.9 (1.4, 2.6) | <0.001 | 0.9 (0.6, 1.5) | 0.77 |
| GERD | 1059 (23.6%) | 0.8 (0.6, 1.1) | 0.20 | 1.1 (0.8, 1.6) | 0.53 |
| Congestive Heart Failure (CHF) | 887 (19.8%) | 2.4 (1.8, 3.2) | <0.001 | 1.5 (1.1, 2.2) | 0.02 |
| Depression | 1280 (28.6%) | 1.0 (0.8, 1.4) | 0.76 | 1.1 (0.8, 1.5) | 0.69 |
| Diabetes | 1283 (28.6%) | 1.4 (1.1, 1.9) | 0.01 | 1.4 (1.0, 1.9) | 0.05 |
| Drug abuse | 91 (2.0%) | 0.8 (0.2, 2.0) | 0.70 | 0.3 (0.0, 1.4) | 0.21 |
| MI | 2355 (52.5%) | 1.4 (1.1, 1.8) | 0.02 | 1.6 (1.2, 2.3) | 0.004 |
| Hypertension | 2853 (63.6%) | 0.8 (0.6, 1.1) | 0.11 | 1.0 (0.7, 1.4) | 0.95 |

TABLE 1-continued

BASELINE CHARACTERISTICS AND UNIVARIATE ODDS RATIOS

| | n = 4,484 | One-Year Mortality | | One-Year ACS Admission | |
|---|---|---|---|---|---|
| | | Odds Ratio (95% CI) | p-value | Odds Ratio (95% CI) | p-value |
| Smoking status | | | | | |
| Never | 686 (15.6%) | — | 0.12 | — | 0.24 |
| Past | 2721 (62.0%) | 1.3 (0.8, 1.9) | | 1.3 (0.8, 2.3) | |
| Current | 980 (22.3%) | 1.6 (1.0, 2.5) | | 1.6 (0.9, 2.9) | |
| Chronic renal insufficiency | 694 (15.5%) | 1.6 (1.1, 2.1) | 0.005 | 1.1 (0.7, 1.7) | 0.55 |
| Liver disease | 320 (7.1%) | 1.3 (0.8, 2.0) | 0.30 | 0.6 (0.3, 1.2) | 0.22 |
| Post-traumatic stress disorder | 516 (11.5%) | 1.1 (0.7, 1.6) | 0.74 | 1.3 (0.8, 2.0) | 0.27 |
| Seizures/convulsions | 187 (4.2%) | 1.0 (0.5, 1.8) | 0.98 | 0.4 (0.1, 1.2) | 0.16 |
| Peptic ulcer disease | 984 (21.9%) | 1.2 (0.9, 1.6) | 0.28 | 1.1 (0.7, 1.6) | 0.64 |
| Stroke | 742 (16.6%) | 1.6 (1.2, 2.2) | 0.002 | 1.4 (1.0, 2.1) | 0.07 |
| Thyroid disease | 196 (4.4%) | 1.6 (0.9, 2.7) | 0.07 | 0.6 (0.2, 1.4) | 0.31 |
| Prior PTCA or CABG | 2138 (47.7%) | 1.2 (0.9, 1.6) | 0.16 | 1.9 (1.4, 2.6) | <0.001 |
| SAQ Physical Limitation | | | | | |
| Minimal | 856 (19.1%) | — | <0.001 | — | <0.001 |
| Mild | 1239 (27.6%) | 1.6 (0.9, 2.8) | | 1.6 (0.9, 3.0) | |
| Moderate | 1728 (38.5%) | 2.5 (1.5, 4.2) | | 2.7 (1.6, 5.0) | |
| Severe | 661 (14.7%) | 6.2 (3.7, 10.3) | | 2.8 (1.5, 5.3) | |
| SAQ Angina Stability | | | | | |
| Much better | 831 (18.5%) | — | <0.001 | — | 0.05 |
| Slightly better | 439 (9.8%) | 1.3 (0.8, 2.2) | | 1.7 (0.8, 3.5) | |
| Unchanged | 2339 (52.2%) | 1.2 (0.8, 1.8) | | 1.9 (1.2, 3.4) | |
| Slightly worse | 576 (12.9%) | 1.1 (0.7, 1.9) | | 2.5 (1.4, 4.8) | |
| Much worse | 299 (6.7%) | 2.9 (1.8, 4.8) | | 2.3 (1.1, 4.9) | |
| SAQ Angina Frequency | | | | | |
| Minimal | 2437 (54.4%) | — | <0.001 | — | <0.001 |
| Mild | 1268 (28.3%) | 1.0 (0.7, 1.4) | | 1.6 (1.1, 2.3) | |
| Moderate | 539 (12.0%) | 1.8 (1.3, 2.6) | | 2.6 (1.6, 4.0) | |
| Severe | 240 (5.4%) | 2.6 (1.6, 4.0) | | 3.1 (1.7, 5.3) | |
| SAQ Quality of Life | | | | | |
| Excellent | 1791 (39.9%) | — | 0.002 | — | <0.001 |
| Good | 1461 (32.6%) | 1.3 (0.9, 1.7) | | 2.1 (1.4, 3.3) | |
| Fair | 916 (20.4%) | 1.5 (1.1, 2.2) | | 3.2 (2.0, 4.9) | |
| Poor | 316 (7.1%) | 2.4 (1.5, 3.7) | | 2.2 (1.1, 4.1) | |

*Odds ratios per +10 years

Figure 3:
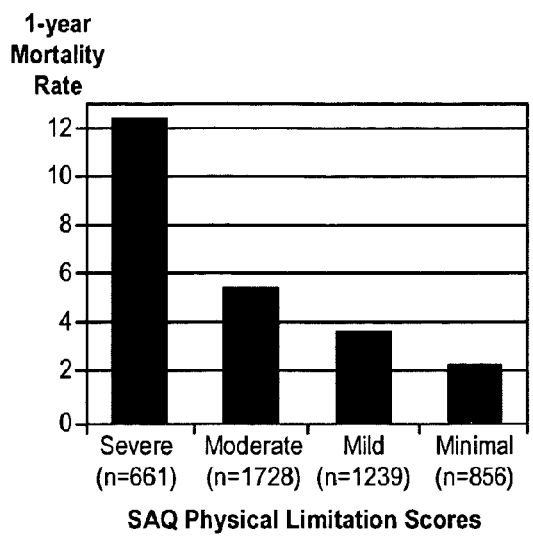
FIG. 3 shows a prognostic statistical model including a bar graph that relates SAQ physical limitation scores to one year mortality in the test study group.
Figure 4:
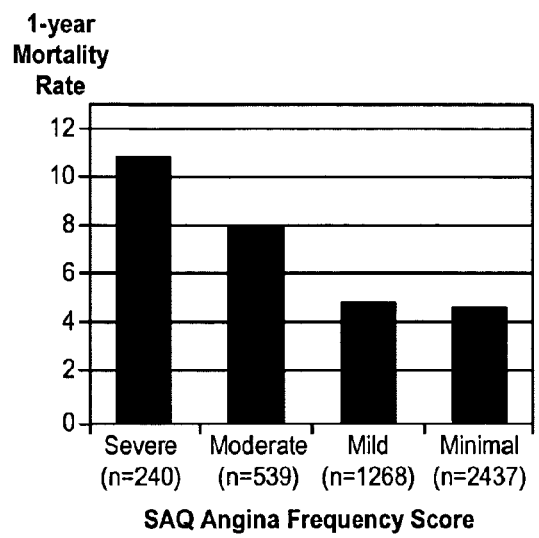
FIG. 4 shows a prognostic statistical model including a bar graph that relates SAQ angina frequency scores to one year mortality in the test study group.
Figure 5:
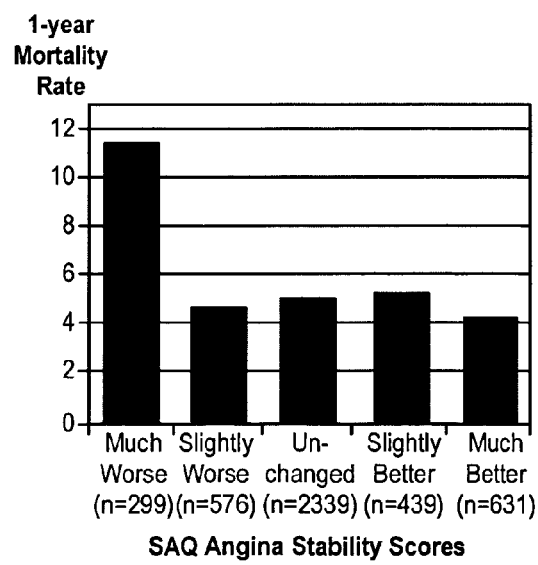
FIG. 5 shows a prognostic statistical model including a bar graph that relates SAQ angina stability scores to one year mortality in the test study group.
Figure 6:
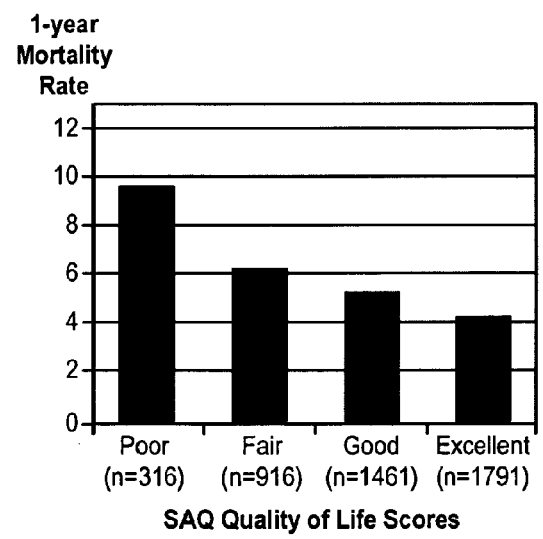
FIG. 6 shows a prognostic statistical model including a bar graph that relates SAQ quality of life scores to one year mortality in the test study group.

The information from Table 1 may be depicted graphically and used in a three dimensional model. For example, the Kaplan-Meier curves shown in FIG. 2 may be linked to SAQ scores through a common mortality. Accordingly, the model is able to project that a person with an initial SAQ baseline in one of the stratified rankings may cross the boundary into another stratification having a higher mortality at a future point in time. For example, FIG. 3 is a bar graph providing point-in-time graphical representation of actual mortality rates for SAQ quartile ranges of the physical limitation domain. FIG. 4 is a bar graph providing a graphical representation of actual mortality results for the angina frequency domain, which was divided into SAQ ranges including Much Worse (0-24), Slightly Worse (25-49), Unchanged (50), Slightly Better (51-75), and Much Better (76-100). FIG. 5 is a bar graph providing a graphical representation of results for the angina stability domain. FIG. 6 is a bar graph providing a graphical representation of quartile results for the quality of life domain.

In this particular study group, the strongest health status predictor was SAQ physical limitation. Angina frequency and quality of life domains all had a significant trend toward lower mortality with higher patient function, fewer symptoms, and better quality of life. The angina stability SAQ scores measure changes in patients' angina. Those patients reporting increased angina over the past month had a one year mortality rate of 11.4% compared with 4.9% for the rest of the study population. An expert-defined rules base may concentrate upon making prognostic assessments of outcome likelihood on the basis of the strongest predictors, or on the basis of a combination of the strongest predictors. For example, a combination of predictors may be used to enhance overall results through use of a multivariate prognostic model that is produced using the strongest predictors, as shown in Example 4.

EXAMPLE 4

Multivariable Prognostic Models

As shown above, physical limitation and angina frequency were the best SAQ-based predictors for both one year mortality and ACS hospital admission. These predictors were studied in combination with demographic and clinical data, as shown in Tables 2 and 3. The effect of the multivariable analysis was, for example, to correct the univariate results shown in Table 1 for demographic and clinical factors that are unrelated to ACS, and vice versa. For example, the odds ratio for the "Severe" range of the "Physical Limitation" domain is shown as being 6.0 in the univariate approach and 4.0 when corrected for the contribution of other factors, such as cancer, age, previous hospitalization, and CHF. In addition to adjusting the magnitude of the scores in a minor way, these multivariable results confirmed that SAQ scores in the physical limitation and angina frequency domains are valid independent predictors of future mortality and ACS hospitalization.

TABLE 2

PROGNOSTIC MODELS FOR ONE-YEAR MORTALITY

| | Model 1 (SAQ) | | Model 2 (Clinical) | | Model 3 (Combined) | |
|---|---|---|---|---|---|---|
| | Odds Ratio (95% CI) | p-value | Odds Ratio (95% CI) | p-value | Odds Ratio (95% CI) | p-value |
| Physical Limitation | | | | | | |
| Minimal | — | <0.001 | | | — | <0.001 |
| Mild | 1.7 (1.0, 3.0) | | | | 1.5 (0.9, 2.7) | |
| Moderate | 2.6 (1.6, 4.4) | | | | 2.0 (1.2, 3.5) | |
| Severe | 6.0 (3.6, 10.6) | | | | 4.0 (2.4, 7.2) | |
| Angina Frequency | | | | | | |
| Minimal | — | 0.068 | | | — | 0.078 |
| Mild | 0.8 (0.5, 1.1) | | | | 0.8 (0.6, 1.2) | |
| Moderate | 1.1 (0.8, 1.6) | | | | 1.2 (0.8, 1.8) | |
| Severe | 1.4 (0.9, 2.2) | | | | 1.6 (0.9, 2.5) | |
| Age (per +10 years) | | | 1.6 (1.4, 1.9) | <0.001 | 1.6 (1.3, 1.8) | <0.001 |
| CHF | | | 2.3 (1.7, 3.0) | <0.001 | 1.9 (1.4, 2.5) | <0.001 |
| Cancer | | | 1.5 (1.1, 2.1) | 0.015 | 1.5 (1.0, 2.0) | 0.031 |
| Prior hospitalization | | | 1.5 (1.1, 2.0) | 0.024 | 1.4 (1.0, 1.9) | 0.065 |
| Diabetes | | | 1.3 (1.0, 1.7) | 0.059 | 1.3 (0.9, 1.7) | 0.129 |
| Stroke | | | 1.3 (1.0, 1.8) | 0.092 | 1.2 (0.8, 1.6) | 0.396 |
| c-statistic | 0.66 | | 0.69 | | 0.72 | |
| Original dataset Validated | 0.66 | | 0.67 | | 0.70 | |
| Hosmer-Lemeshow p-value | 0.57 | | 0.16 | | 0.26 | |

TABLE 3

| PROGNOSTIC MODELS FOR ONE-YEAR ACS ADMISSION | | | | | | |
|---|---|---|---|---|---|---|
| | Model 1 (SAQ) | | Model 2 (Clinical) | | Model 3 (Combined) | |
| | Odds Ratio (95% CI) | p-value | Odds Ratio (95% CI) | p-value | Odds Ratio (95% CI) | p-value |
| Physical Limitation | | | | | | |
| Minimal | — | 0.030 | | | — | 0.102 |
| Mild | 1.4 (0.7, 2.6) | | | | 1.5 (0.8, 2.9) | |
| Moderate | 2.1 (1.2, 3.8) | | | | 2.0 (1.1, 3.8) | |
| Severe | 1.9 (1.0, 3.7) | | | | 1.8 (0.9, 3.6) | |
| Angina Frequency | | | | | | |
| Minimal | — | 0.005 | | | — | 0.016 |
| Mild | 1.4 (0.9, 2.0) | | | | 1.4 (0.9, 2.0) | |
| Moderate | 2.1 (1.3, 3.3) | | | | 2.0 (1.2, 3.2) | |
| Severe | 2.4 (1.3, 4.3) | | | | 2.2 (1.2, 4.2) | |
| Prior hosp (ACS) | | | 11.7 (7.4, 18.1) | <0.001 | 10.6 (6.7, 16.7) | <0.001 |
| Prior hosp (other) | | | 2.8 (1.9, 4.2) | <0.001 | 2.7 (1.8, 4.0) | <0.001 |
| Prior PTCA/CABG | | | 1.6 (1.2, 2.3) | 0.005 | 1.6 (1.2, 2.3) | 0.004 |
| c-statistic | 0.63 | | 0.69 | | 0.73 | |
| Original dataset | 0.62 | | 0.66 | | 0.70 | |
| Validated Hosmer-Lemeshow p-value | 0.32 | | 0.87 | | 0.80 | |

EXAMPLE 5

Personal Input and Evaluation Modeling

The models shown in Tables 1-3 are used as inverted models in the sense that they were created in a forward manner from the analysis of vast amounts of statistical data, but they may be used in a reverse manner by:

- accepting personal input data;
- calculating a SAQ score; and
- entering the tables to determine whether the person has a relatively greater risk of encountering an adverse outcome according to any particular modality.

In a hypothetical example, John Doe is hospitalized for a treatment of moderate blockages of his coronary arteries (atherosclerosis). As a routine matter to pass time while undergoing treatment, a doctor administers the SAQ. John dutifully provides a response, which is scanned and scored electronically in accord with the personal input step 118 of FIG. 1. The score places John in a severe range for physical limitation and a severe range for angina frequency. Accordingly, in the evaluation step 120 an electronic system accesses the model shown in Table 2 to show that John has a 4× greater chance of dying in the next year than does someone with minimal physical limitation, and a 1.6× greater chance of dying than does someone with minimal angina frequency, resulting in a combined mortality risk that is 6.4-fold greater than someone with minimal physical limitations on angina. Alternatively, the system can also consult FIG. 3 to ascertain that his overall one year mortality rate, as someone with severe physical limitation and angina, is about 12%.

EXAMPLE 6

Categorization and Recommendation

In Example 5, John may be categorized as a man, as a man who has mild atherosclerosis, as a man who has severe physical limitation, and as a person with severe angina. As a person with cancer, John may stand a greater chance of dying from cancer than from CAD over the next year. Due to his particular cancer and the treatment employed, it may not be practicable to implement treatment for his CAD, or only a few treatments may be workable. Other options may be affected by his age in combination with his cancer. These categorizations may be assisted by demographic or clinical data obtained for his personal input.

On the basis of categorization data and input from the expert-defined rules base 116, a medical recommendation in step 124 may be rendered according to the categorization. Significantly, some configurations of the present invention provide evidence of predicted outcomes that can assist in the selection of therapies aligned with the goals and values of the individual patient under the guidance of their physician rather than providing so-called "right" or "wrong" decisions that an expert rules-based decision system might provide.

EXAMPLE 7

Disease Management Program

Figure 7:
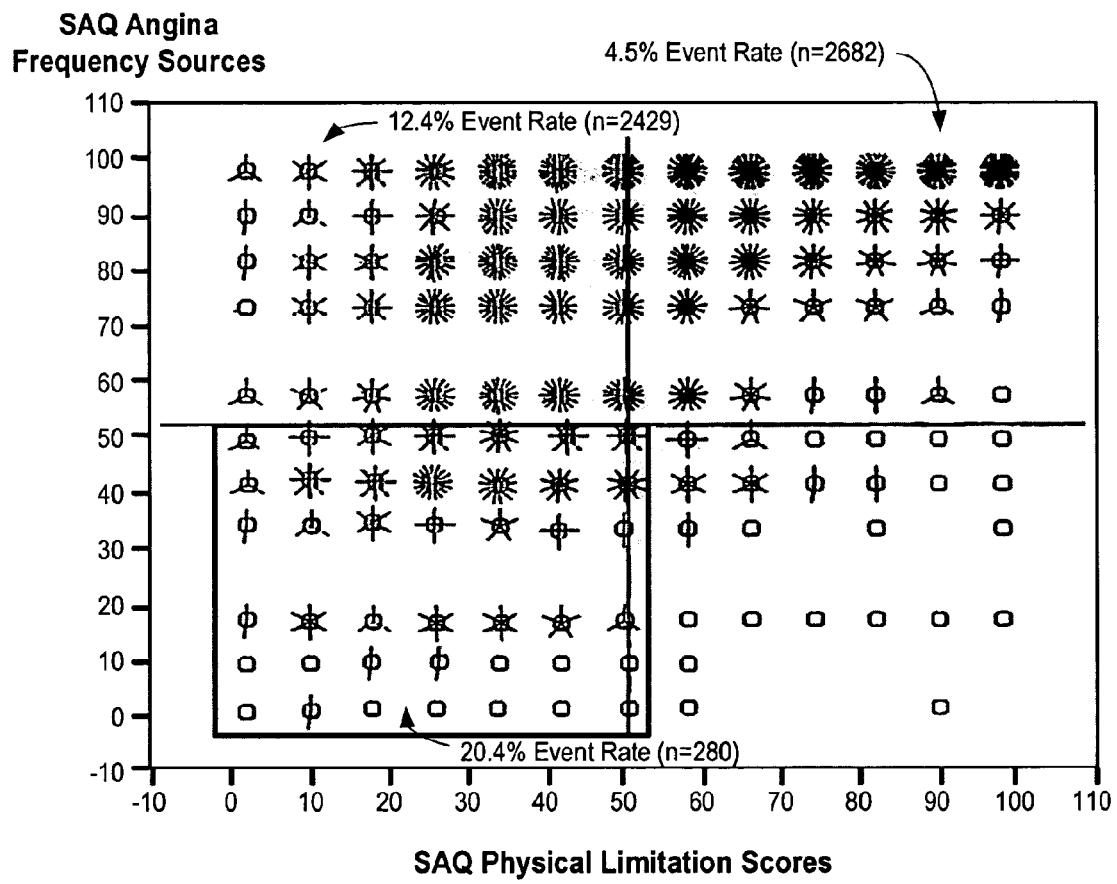
FIG. 7 shows a descriptive statistical model including a plot of scores from two different health status domains including SAQ Angina Frequency Score and SAQ Physical Limitation Score, such that spatial regions of the plot are associated with extremely high risk of mortality.

FIG. 7 demonstrates the application of the data from FIGS. 2-6 into a disease management model. FIG. 7 provides an example of the general principle of leveraging the health status scores of populations of patients to identify high risk individuals. SAQ angina frequency scores (abscissa) are plotted against SAQ physical limitation scores (ordinate) for the same person to form a distribution. Those patients in the lower left quadrant have frequent angina (SAQ angina frequency scores <50) and marked physical limitation (SAQ Physical Limitation <50). Statistical calculations show that those patients in the upper left quadrant have a 20.4% chance of dying over the next 2 years. Those in the lower left quadrant have a 12.4% chance of dying while those in both quadrants on the right side of the graph have a 4.5% risk.

A healthcare system managing a population of patients may use such a categorization technique, i.e., plotting different personal score domains from the same health status survey against one another, stratifying the data on the basis of spatial location (e.g., the lower left quadrant), and calculating the odds of an outcome on the basis of this stratification. In FIG. 7, the technique has produced an astonishing predictor indicating a 20.4% chance of death. This information would certainly be of value to a person who stands, for example, a 1% chance of dying while undergoing an elective cardiac procedure. Prospectively, a person showing a SAQ score in the lower left quadrant would benefit most from a cardiac consultation. A health care provider or a health maintenance organization might choose to use these statistics to manage a healthcare plan with scarce resources in such a way that persons who will benefit the most from services with limited availability receive the services on a preferential basis.

Figure 8:
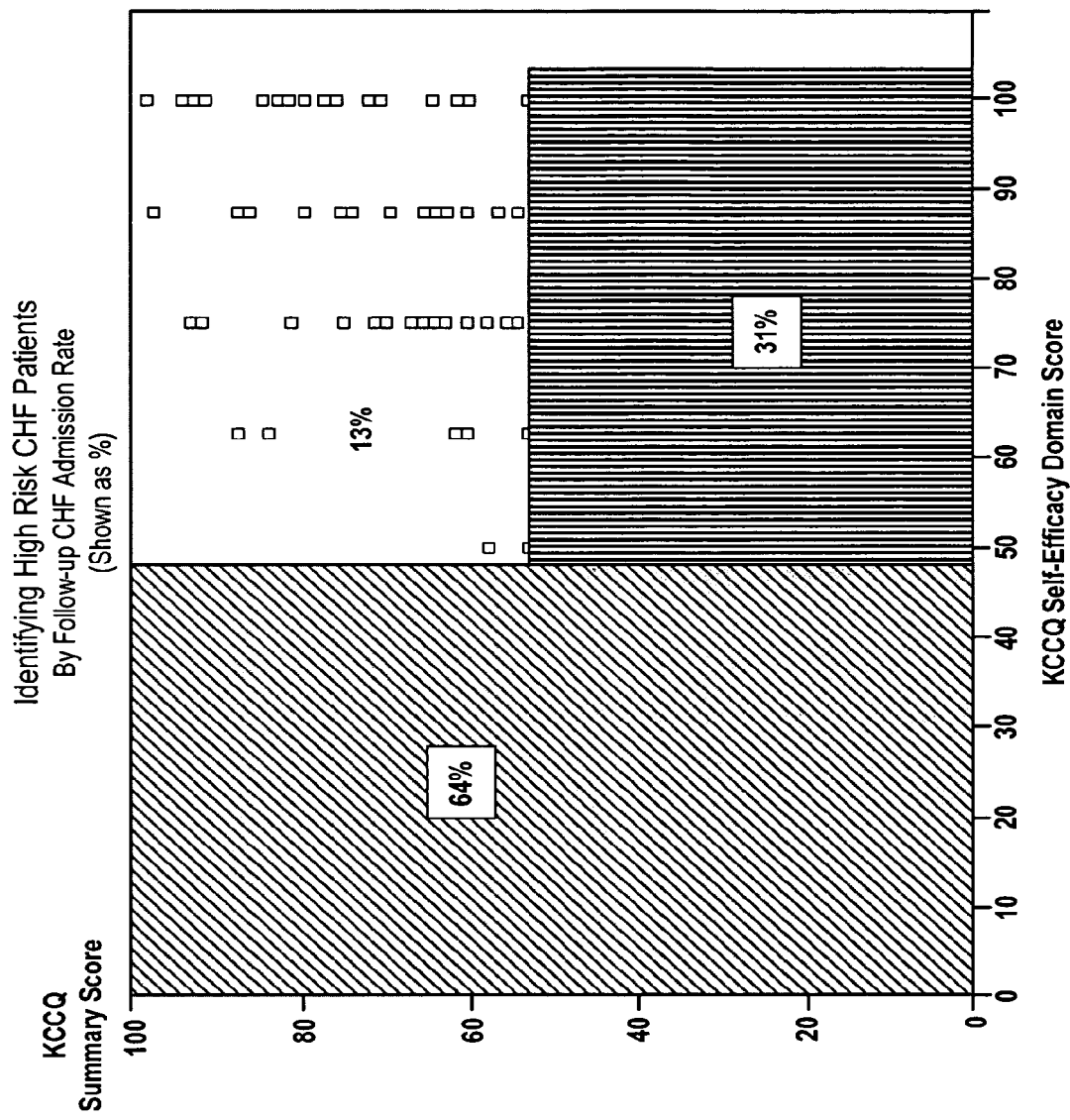
FIG. 8 shows a descriptive statistical model including a plot of scores from two different health status domains including Kansas City Cardiomyopathy (KCCQ) Summary Score and KCCQ Self-Efficacy Domain Score; such that spatial regions of the plot are associated with extremely high risk of mortality.

Similarly, FIG. 8 shows a similar model for patients with congestive heart failure using cross-plotted domains from the Kansas City Cardiomyopathy Questionnaire. An overall summary score (abscissa) is plotted against the self-efficacy score (ordinate). Differing rates of hospital admission and death are statistically correlated to spatial domains, as in FIG. 8. Admission rates differ from 64% for persons who plot on the lower right hand area to 31% and 13% for persons in the respective left hand side and upper right areas.

Figure 9:
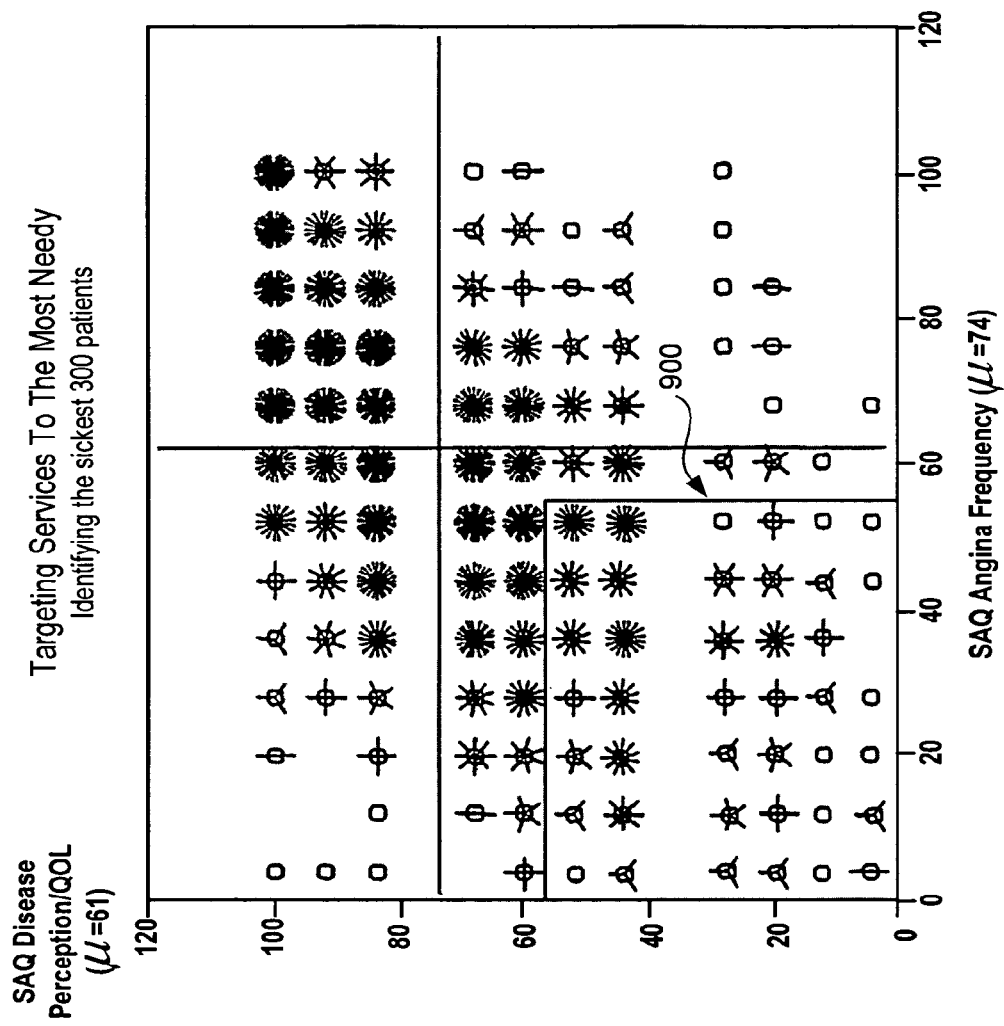
FIG. 9 shows a descriptive statistical model including a plot of scores from two different health status domains including SAQ Angina Frequency Score and SAQ Disease Perception/Quality of Life Score, such that spatial regions of the plot are associated with patients experiencing frequent symptoms that are having an extremely adverse effect upon their quality of life.

FIG. 9 is a model formed as a plot of SAQ angina frequency versus SAQ quality of life scores. The shaded region 900 identifies patients who have angina occurring approximately once-a-week or greater and who are moderately to extremely limited in their quality of life because of the angina. On the basis of subjectively defined rules that can be tailored to a particular healthcare environment using the expert-defined rules base 116, these patients may warrant careful evaluation for opportunities to improve their symptom control.

Figure 10:
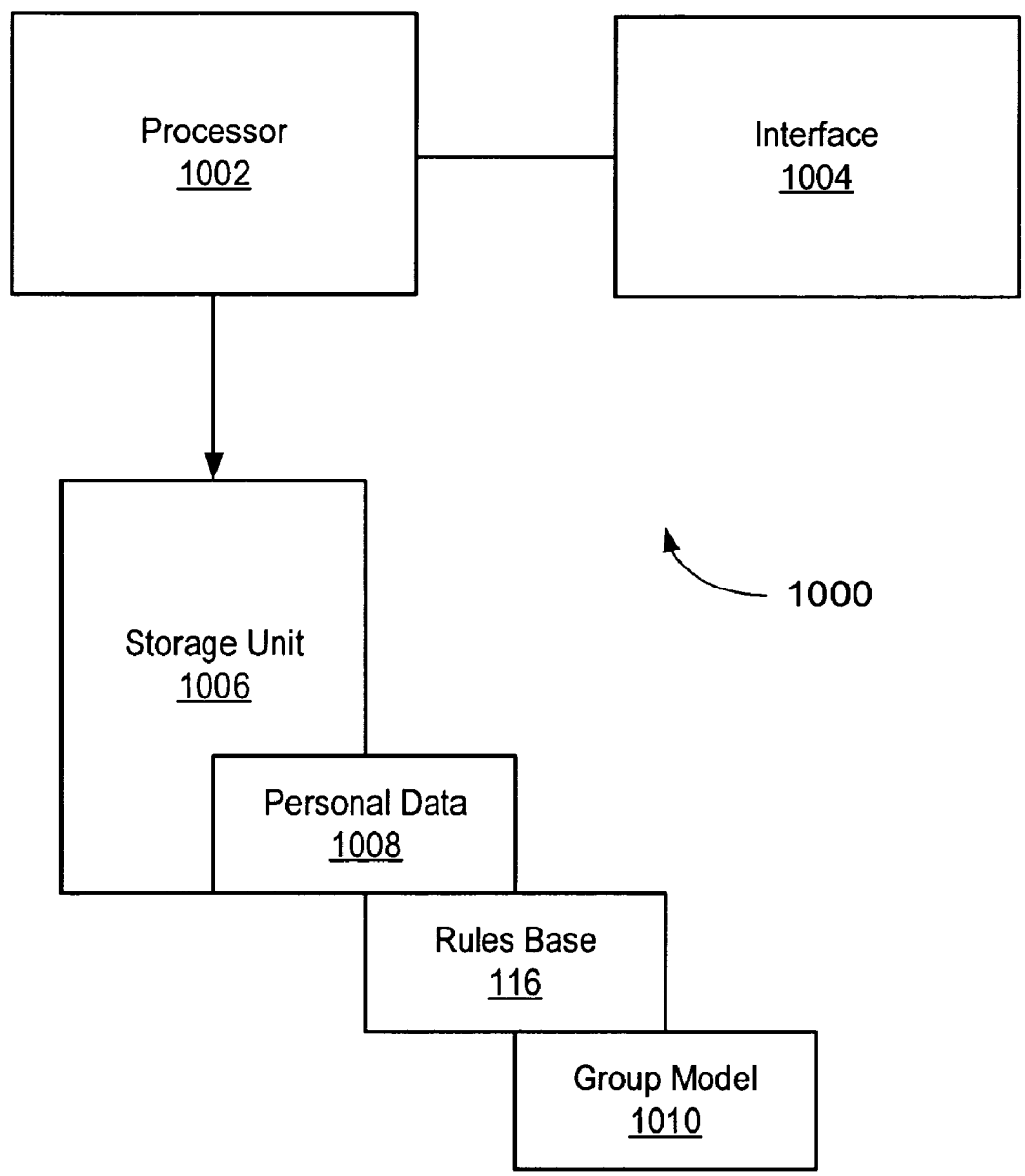
FIG. 10 shows a medical evaluation system, in accord with one embodiment of the invention.

By way of example, FIG. 10 shows a medical evaluation system 1000 that is configured for predicting or describing patient health outcome in a person with sub-marginal cardiac function. Medical evaluation system 1000 may include processor 1002, graphical user interface 1004, and a data storage unit 1006. The graphical user interface 1004 may be configured for presenting questionnaires to the person. Graphical user interface 1004 may receive the responses from the person for subsequent processing by processor 1002 and storage in the data storage unit 1006, e.g., in a logically defined personal database storage component 1008. Graphical user interface 1004, by way of example, could be administered over the internet, locally through a touch screen, via computer keyboard, by voice recognition technology, or through a mouse-driven interface. An appropriate device containing interface 1004 may, for example, be a personal computer, personal data assistant (PDA), cellular telephone, or other electronic device.

In medical system 1000, processor 1002 is communicatively connected to interface 1004 for scoring the responses and evaluating the responses. Evaluation may be performed using the expert-defined rules base 116 and information from a group study model 1010 that is produced using the methodologies shown and described in Examples 1-7. Processor 1002 reports the evaluation results to a system user through interface 1004, or by another means such as a printer or electronic messaging. By way of example, the group data 1010 may be compiled from a single hospital or insurance carrier population or may be representative of a national or global population. In one embodiment, group data 1010 may be downloaded from the internet.

A feature of the test study group model 1010 is that it may contain information from a statistically validated survey, i.e., one having statistical correlation indicators indicating that measured predictive parameters are closely related to a measured outcome. For example, validation may be proven through the use of delimiting metrics, such as p values less than a delimiting value of 0.05 (see, e.g., Tables 1-3). The group study model 1010 may be accessed to provide a prognostic ranking or other measure of health outcomes. For example, processor 1002 could use models represented by any of FIG. 2-9 or Tables 1-3 to identify SAQ scores in domains where the scores indicate sub-marginal cardiac function. New responses in the personal data 1008 may be scored and input for comparison against the group study model 1010 and the expert-defined rules base 116 to assess the respondent's odds of encountering an outcome.

A user of medical system 1000 may be able to generate reports from the system by interactively adjusting pre-defined delimiters or parameters. For example, the test study group data 1010 might be accessed to calculate a Kaplan-Meier curve like FIG. 1, except stratification might include an additional 30% SAQ range and new responses could be evaluated and filtered on the basis of this new range. Alternatively, the shaded region 900 in FIG. 9 might be manipulated as a graphical user interface through the use of drag and drop functions to produce a new spatial range that triggers calculation and reporting of outcome statistics that are attributed to that spatial range.

Processor 1002 may also rank medical information scores, such as health status scores, to predict patient health outcome of an individual patient. For example, where the patient has sub-marginal cardiac function, the questionnaire may be the SAQ, the Kansas City Cardiomyopathy Questionnaire (KCCQ), or any other questionnaire that includes a disease-specific health status measure.

The test study group data 1010 may also include, for example, a reporting network of other administrative data, such as the date of last visit with a cardiovascular specialist or a list of specific cardiovascular medications that the patient may or may not be taking. A patient's current treatment may be automatically reported to the personal database 1008 by other databases (not shown) that are linked to storage unit 1006. For example, a pharmaceutical database describing what therapies have been prescribed may allow relationships between categories of scores so that opportunities for further treatment and treatment efficacy may be linked to medical information. Other diagnostic databases, such as those for angiography or echocardiography, can be used to suggest certain treatments. For example, outcomes from these diagnostic databases may be linked with health status information to suggest an increase in dosage for a certain pharmaceutical agent; the use of a device, such as a stent; or a procedure including angiography or bypass surgery. Further statistical linkage of medical information data to actual health outcomes associated with the recommended treatments may provide statistical optimization that improves health outcomes for a group of patients that is studied.

Figure 11:
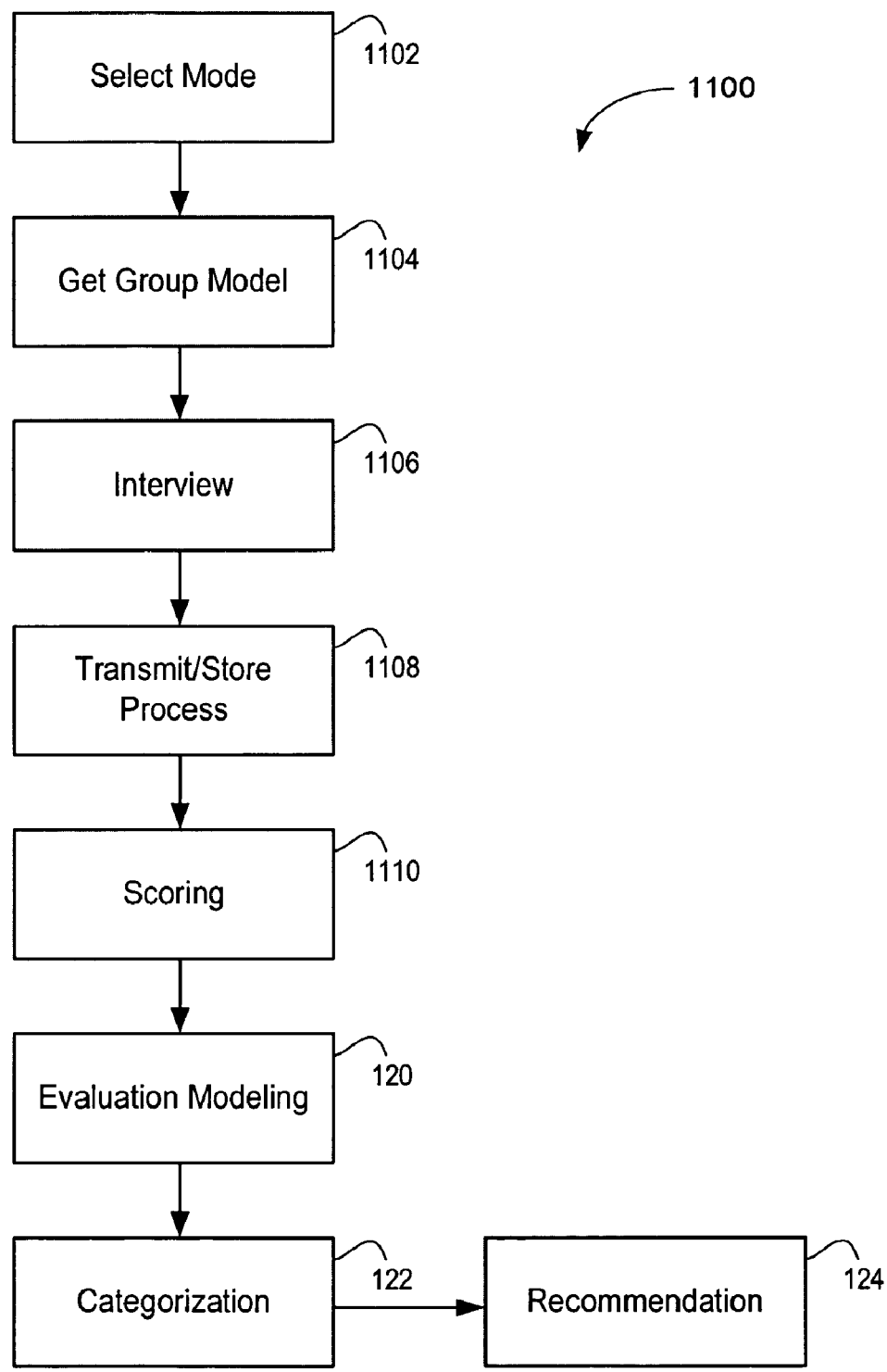
FIG. 11 shows a flow chart illustrating an operation of the system of FIG. 10.

FIG. 11 shows a flow chart illustrating operation 1100 of system 1000, in accord with one method. Operation 1000 commences with mode selection 1102, which may entail user selection of a medical mode for a particular disease or medical condition from among a plurality of such diseases or conditions, e.g., ACS, diabetes, or cancer. Step 1104 entails processor 1102 retrieving a model group that may comprise a selected medical information questionnaire, program instruction for implementing the rules base 116, and the group model 1010 for the selected medical mode.

The graphical user interface 1004 receives responses from a person in an interview step 1106, which may also entail retrieval of information, such as demographic and clinical information, from other databases (not shown). Processor 1002 may receive transmitted personal responses from graphical user interface 1004, store the responses in the personal database 1008, and process the responses. Processing may include scoring 1110 to obtain scores, followed by evaluation modeling 120, categorization 122, and recommendation 124, as described above in the context of FIG. 1.

Figure 12A:
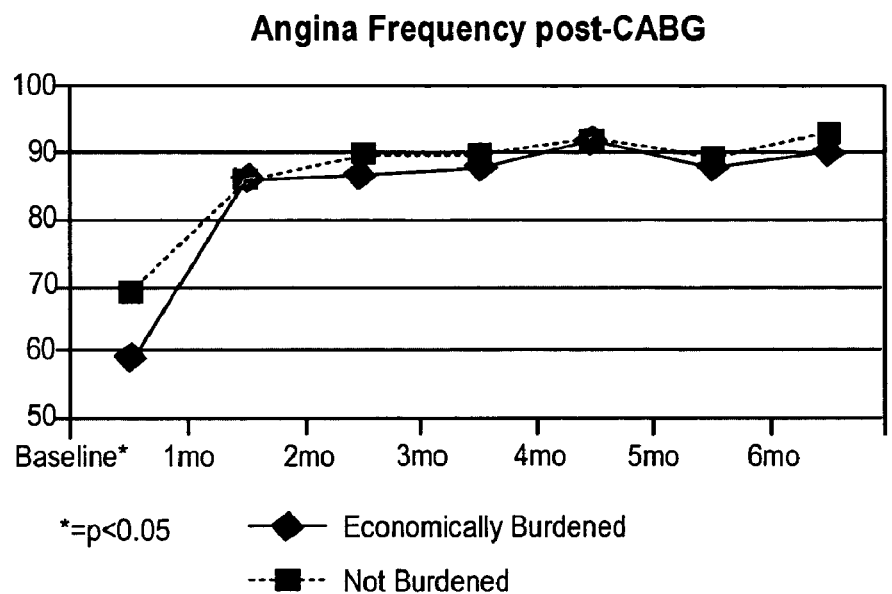
FIGS. 12A and 12B are comparative graphs showing that angina frequency may vary depending upon the type of clinical procedure a patient has undergone and the demographic background of the patient.
Figure 12B:
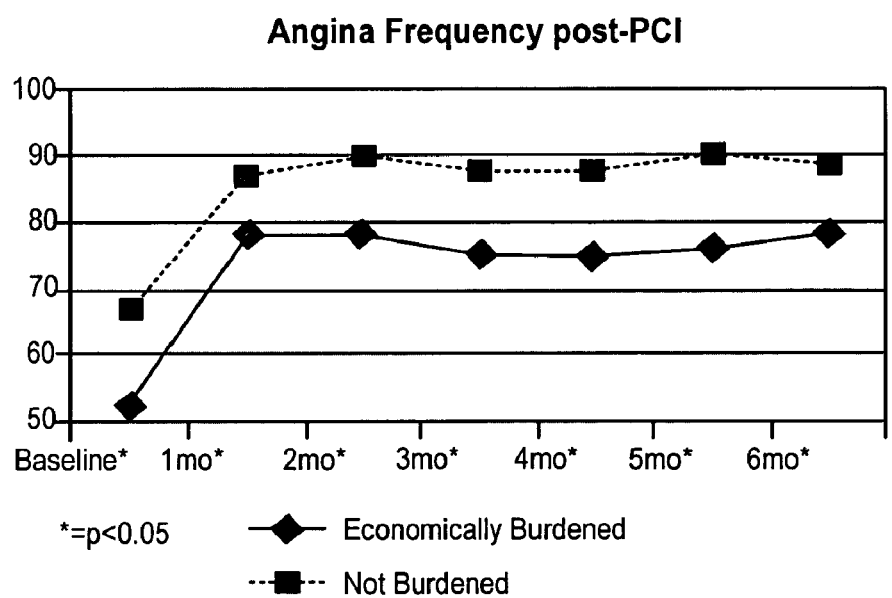

The foregoing discussion emphasizes methodology for using patient self-assessment data to monitor cardiac health, with overtones on how this data might be used in treatment programs, e.g., by changing medication in response to a changing self-assessment score. In additional contexts, the self assessment data, perhaps additionally including patient satisfaction surveys, may be statistically processed to relate demographics and/or and patient satisfaction with having undergone a particular procedure or treatment. By way of example, FIG. 12A is a graph of angina frequency post-CABG (diamond is economically burdened patient; square is not economically burdened patient). Patients characterized as economically burdened had about the same frequency of angina post CABG as did the patient population characterized as economically burdened. FIG. 12B is a graph of angina frequency in patients post-PCI (Percutaneous Coronary Intervention) revascularization. Patients characterized as not economically burdened demonstrate a higher frequency of angina after PO revascularization procedure. These results show that clinical patient outcomes may vary by the type of procedure and demographic background of the patient.

Figure 13:
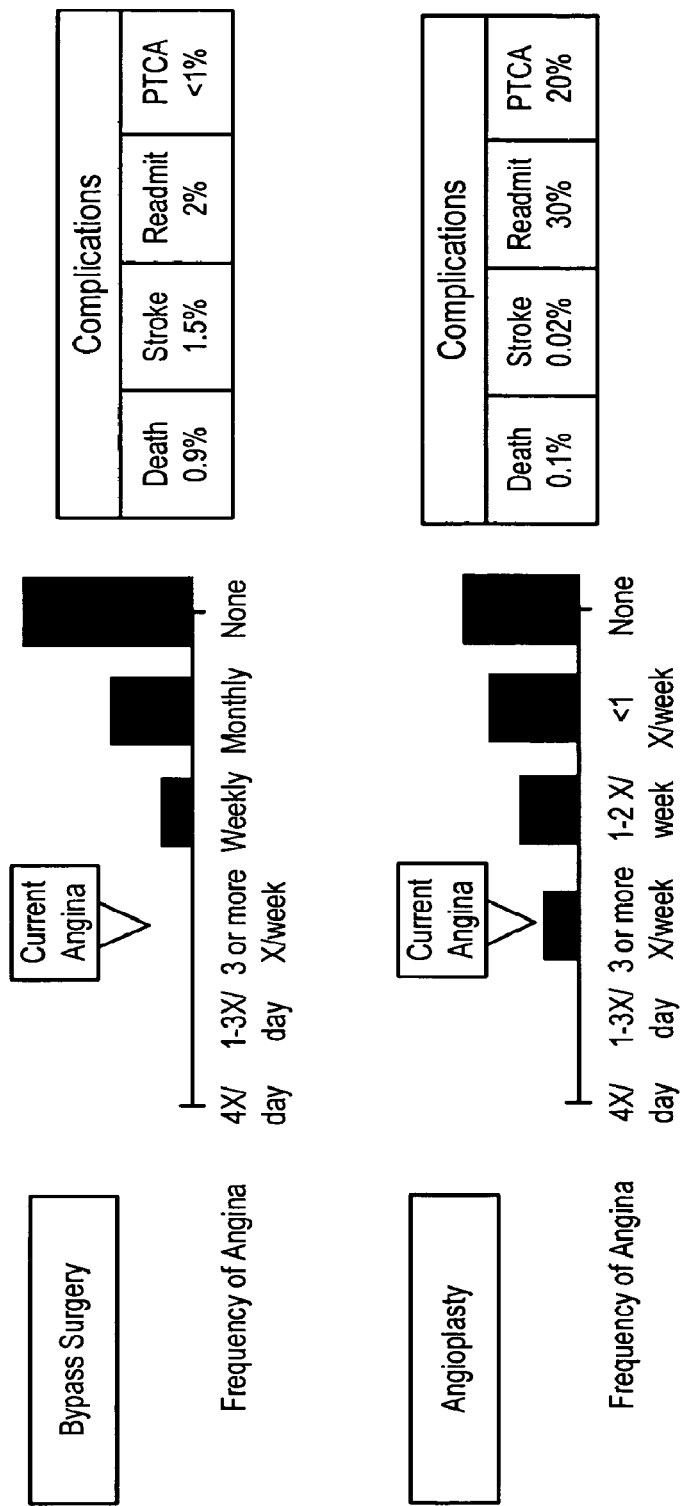
FIG. 13 shows comparative statistics including complications and angina frequency according to different therapeutic options.

FIG. 13 is a graph demonstrating the frequency of angina and statistical likelihood of complications in a post-coronary attack patient having had bypass surgery, as compared to patients having had angioplasty. The complications monitored in these patients were death (0.9%), stroke (1.5%), readmit (2%) and PTCA (less than 1%). FIG. 2 also shows a graph demonstrating the frequency of angina in a post-coronary event patient that had an angioplasty. The same complications were monitored in these patients, with a reported frequency of 0.1% death, 0.02% stroke, 30% readmission to the hospital, and 20% Re PTCA.

Figure 14:
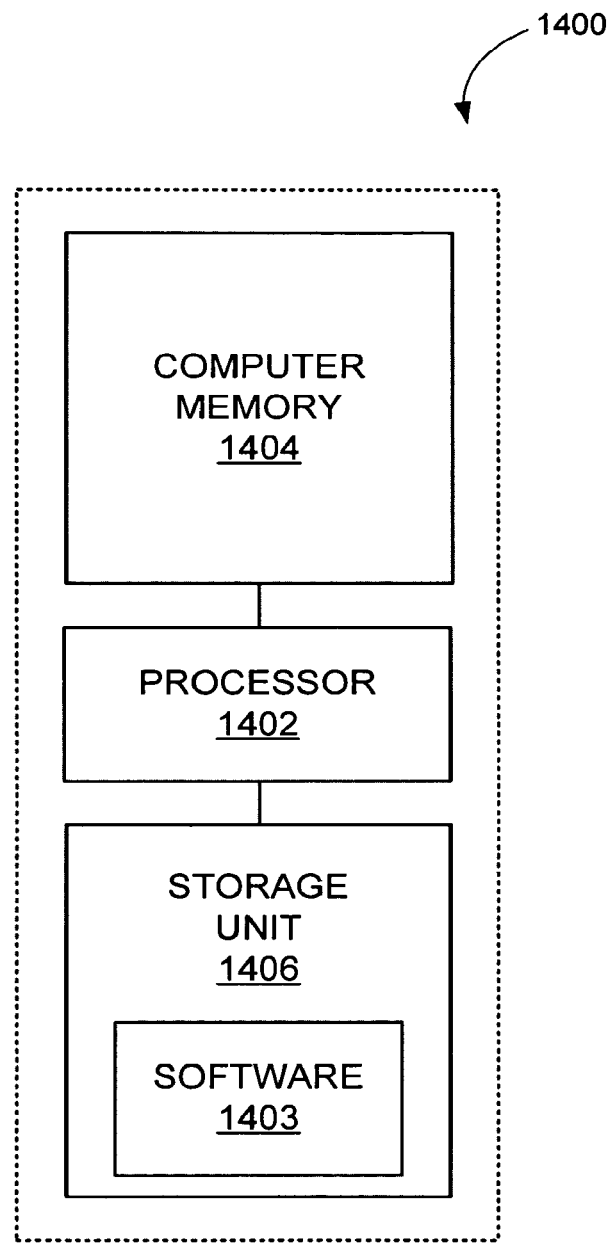
FIG. 14 is a system schematic diagram illustrating various components that may be used to assist patients and medical workers in selecting a clinical procedure based upon a desired patient goal or outcome.

FIG. 14 shows computer system 1400 configured for use in a medical or clinical health care facility to identify an appropriate post-cardiac event regimen according to a desired patient outcome. An individual patient considering options for pre or post-coronary event treatment, in accord with one embodiment, may review statistical information as show in FIGS. 12 and 13. The patient may complete a survey that provides computer system 1400 with the patient's demographic data, lifestyle, and goals. Computer system 1400 processes this information, categorizes the patient, and provides a comparison of outcomes from similarly situated persons who have previously undergone procedures of the types being contemplated. The report is useful in assisting the patient and medical workers in selecting a clinical procedure that is best for the patient according to the desired outcome, adjusted for demographics.

Computer system 1400 may include processor 1402, computer memory 1404, and storage unit 1406. In computer system 1400, processor 1402 is communicatively connected to computer memory 1404 and to storage unit 1406 for operating in accord with a mode of selecting a clinical procedure with assistance of statistics pertaining to other outcomes that may be used as a predictive tool. In one embodiment, computer system 1400 is configured for identifying an individual patient's disease state and demographics of the individual patient comprising age, sex, economic burden, living situation, social support, employment status, type of employment, education level, disease severity, symptoms and clinical setting.

Computer system 1400 may, for example, assess a set of medical information parameters (which may include or consist of "clinical data," as that term is used in the art) from the individual patient to provide a first data assessment profile and identify the projected health outcome desired by the individual patient based upon said individual patient's preferences and goals. Computer system 1400 may also assess a set of medical information parameters from a population of patients having similar demographics to said individual patient, the population of patients having received different treatments, in providing a library of specific projected health outcomes for each different treatment.

Upon assessing the medical information parameters from the population of patients, computer system 1400 may select preferred outcomes from the library of specific projected health outcomes that similarly coincide with preferences and goals of the individual patient, present the preferred outcomes to the patient, and select a clinical treatment that has a projected health outcome that is most similar to the individual patient's desired projected health outcome for the patient based on the preferred outcomes. In one embodiment, software 1403 is configured for operatively controlling computer system 1400 and may initially reside in storage unit 1406. Upon initializing computer system 1400, software 1403 may be loaded in computer memory 1404. Processor 1402 may then run software 1403.

Figure 15:
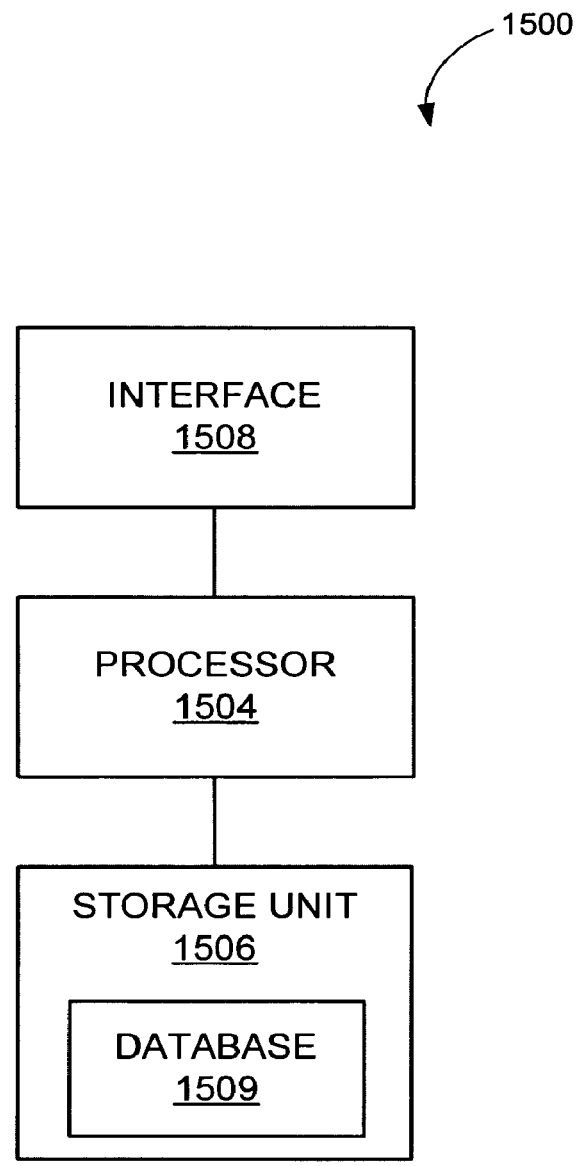
FIG. 15 shows additional aspects that may be included in the system of FIG. 14 according to one embodiment.

FIG. 15 shows medical system 1500 configured for identifying an appropriate post-cardiac event regimen for an individual patient considering options for post-coronary event treatment, in accord with one embodiment of the invention. Medical system 1500 may include processor 1504, storage unit 1506, and interface 1508. In medical system 1500, storage unit 1506 is configured for storing group data in a database 1509. The group data may comprise responses to a questionnaire having a plurality of questions regarding quality of life and demographic information. The response may be derived from a plurality of patients having survived a coronary event. A first group of the patients have received a post-coronary event revascularization procedure. A second group of the patients had not received a post-coronary event revascularization procedure. Demographics of the first and second groups of patients may be similar to those of the individual patient. In medical system 1500, interface 1508 is configured for receiving responses to questions from an individual patient. In medical system 1500, processor 1504 is communicatively connected to interface 1508 and to storage unit 1506 for performing statistical analysis on the responses from the plurality of patients and from the individual patient. A comparison of the statistical analysis of the responses from the group of patients and from the individual patient may provide a basis upon which the individual patient may select a post-cardiac event treatment appropriate to the individual patient preferences and goals of the individual patient.

While the example is given of the selection of a mode of coronary revascularization, other configurations of the present invention may assist, for example, in the cessation of smoking, the institution of an exercise program or compliance with a particular medication regimen. Thus, configurations of the present invention may provide a powerful way of motivating patients to adopt a healthy lifestyle by demonstrating important benefits of lifestyle decisions.

With further regard to FIGS. 13 and 15, those skilled in the art should appreciate that storage unit 1506 and storage unit 1406 may illustratively represent the same storage memory and/or one or a combination of storage unit 1406 and computer memory 1404 within computer system 1400. Processor 1402 may incorporate functionality including processor 1504, for example.

Figure 16:
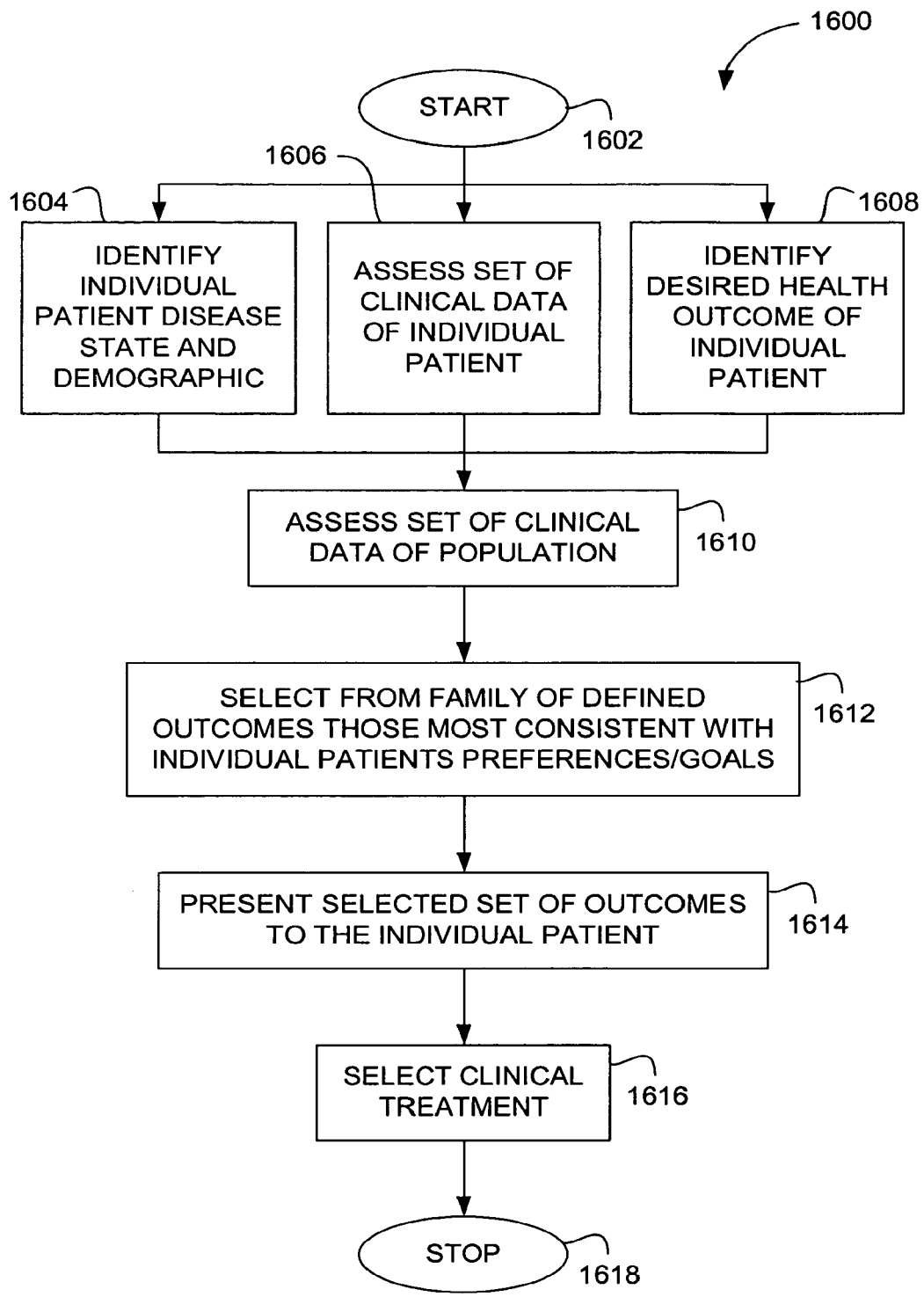
FIG. 16 is a flow diagram of process steps to obtain and to store data according to one embodiment.

FIG. 16 shows a flow chart illustrating operation 1600 of medical system 1500 (shown in FIG. 15), in accord with one methodology. Operation 1600 commences in step 1602. Processor 1504 identifies an individual patient's disease state and demographics of the individual patient comprising age, sex, economic burden, living situation, social support, employment status, type of employment, education level, disease severity, symptoms and clinical setting, in step 1604. Processor 1504 assesses a set of clinical data (as that term is used in the art) of the individual patient, in step 1606. Processor 1504 identifies the projected health outcome desired by the individual patient based upon said individual patient's preferences and goals, in step 1608. Processor 1504 assesses a set of clinical data from a population of patients having similar demographics to the individual patient to provide a library of specific projected health outcomes for each different treatment, in step 1610. Processor 1504 selects preferred outcomes from the library of specific projected health outcomes that similarly coincide with preferences and goals of the individual patient, in step 1612. In step 1614, interface 1508 presents the preferred outcomes to the patient, wherein the outcomes are presented, for example, as a function of available treatment options. Processor 1504 selects a clinical treatment having a projected health outcome that is most similar to the individual patient's desired projected health outcome for the patient based on the preferred outcomes, in step 1616. Operation 1600 ends in step 1618.

Instructions that perform the operation discussed in FIG. 16 may be stored in storage media or computer memory. The instructions may be retrieved and executed by processor 1504. Some examples of instructions include software, program code, and firmware. Some examples of storage media include memory devices, tapes, disks, integrated circuits, and servers. The instructions are operational when executed by processor 1504 to direct processor 1504 to operate in accord with the invention. Those skilled in the art are familiar with instructions and storage media.

Figure 17:
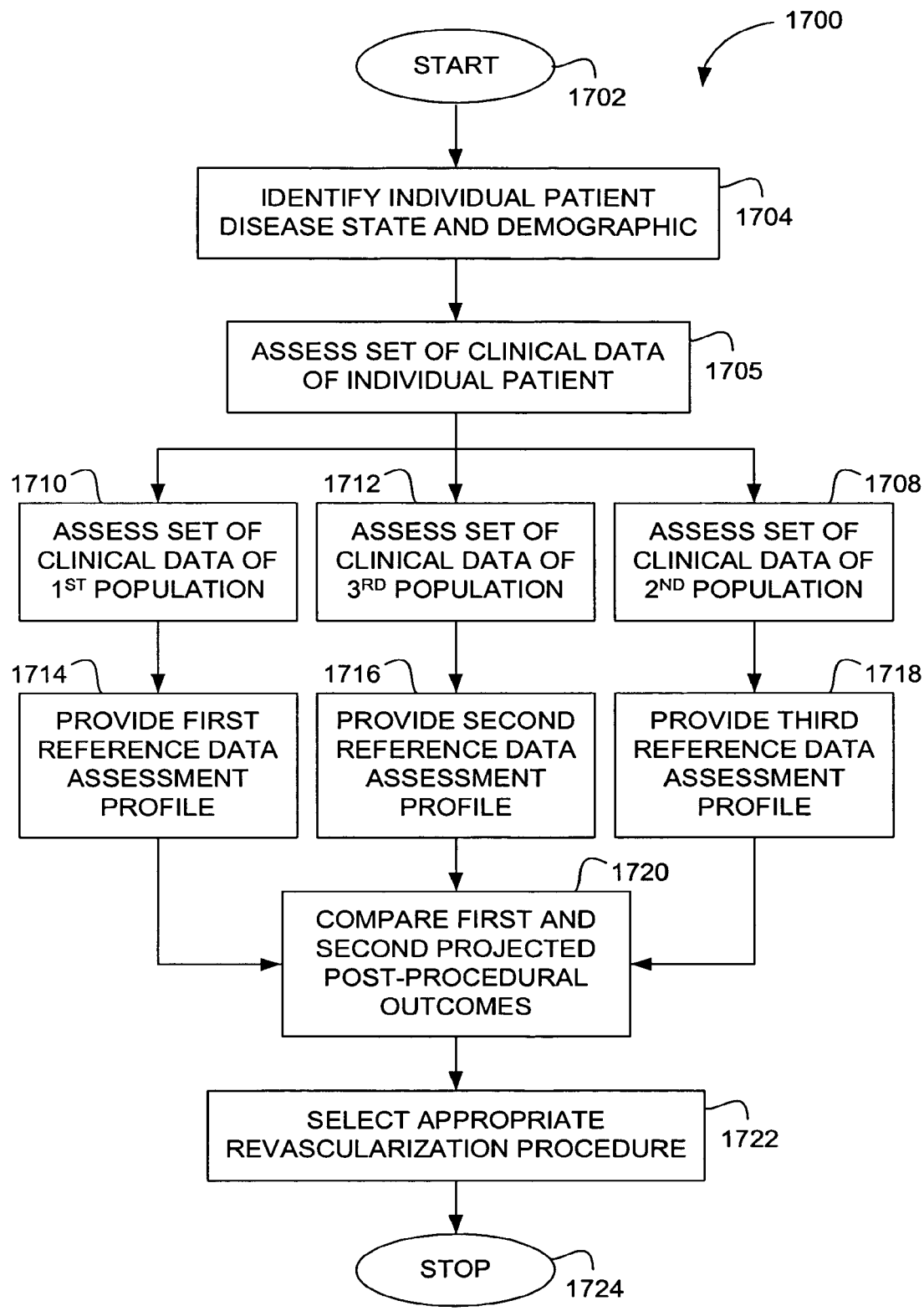
FIG. 17 is a flow diagram of process steps to obtain stored data according to one embodiment.

FIG. 17 shows a flow chart illustrating operation 1700 of medical system 1500 (shown in FIG. 15), in accord with one methodology. Operation 1700 commences in step 1702. Processor 1504 identifies the disease state and demographics of the individual patient, in step 1704. The demographics may include age, sex, economic burden, living situation, social support, employment status, type of employment, education level, disease severity, symptoms and clinical setting. Processor 1504 assesses a set of clinical data from the patient to provide a first data assessment profile, in step 1705. Processor 1504 assesses a set of clinical data from a first population of patients to provide a first reference data assessment profile, in step 1710. Processor 1504 assesses a set of clinical data from a second population of patients to provide a second reference data assessment profile, in step 1712. Processor 1504 assesses a set of clinical data from a third population of patients to provide a third reference data assessment profile, in step 1708. The first, second, and third populations may have similar demographics as the individual patient and differing treatments such as revascularization. Processor 1504 projects the patient's survival and quality of life probability of the individual patient from any number of clinical options. For example, first, second, and third reference data assessment profiles grouped by type of revascularization procedure may be statistically profiled by a processing algorithm to respectively provide first, second, and third projected post-procedural outcomes for the patient prospectively based upon statistics from other patients who have undergone the respective vascularization procedures and/or treatments, in steps 1714, 1716, and 1718. The revascularization procedures may include a coronary artery bypass grafting (CABG) procedure and assessing a set of medical information parameters from a second population having had a Percutaneous Coronary Intervention (PCI) procedure. The treatment may include, for example, an anti-coronary disease medication, diet modification, herbal remedy, or other non-surgical intervention procedure. Processor 1504 compares the first projected post-procedural outcome to the second projected post-procedural outcome, in step 1720. Processor 1504 selects an appropriate revascularization procedure for the individual patient in response to the step of comparing the projected first to the second projected post-procedural outcome, in step 1722. Operation 1700 ends in step 1724.

Figure 18:
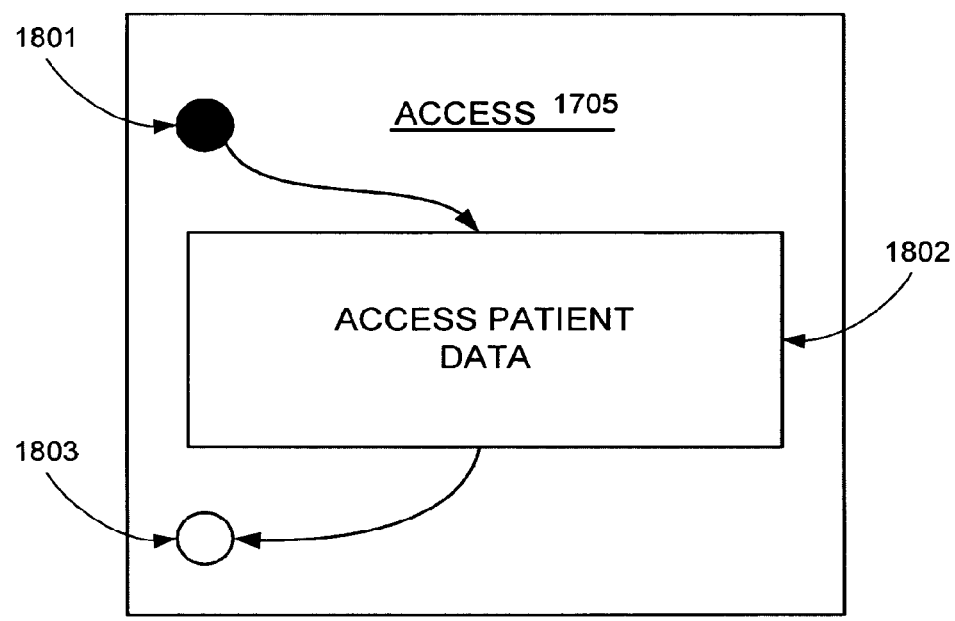
FIG. 18 is a flow chart illustrating additional detail with respect to FIG. 17.

FIG. 18 shows a flow chart illustrating step 1705 of operation 1700, in accord with one methodology. Step 1705 commences through entry point 1801, designating a specific processing algorithm, for example, one operating off of expert rules or a self training algorithm such as a neural network that associates outcomes with clinical procedures. Processor 1504 assesses the individual patient's data, in step 1802. Step 1705 exits through exit point 1803.

Figure 19:
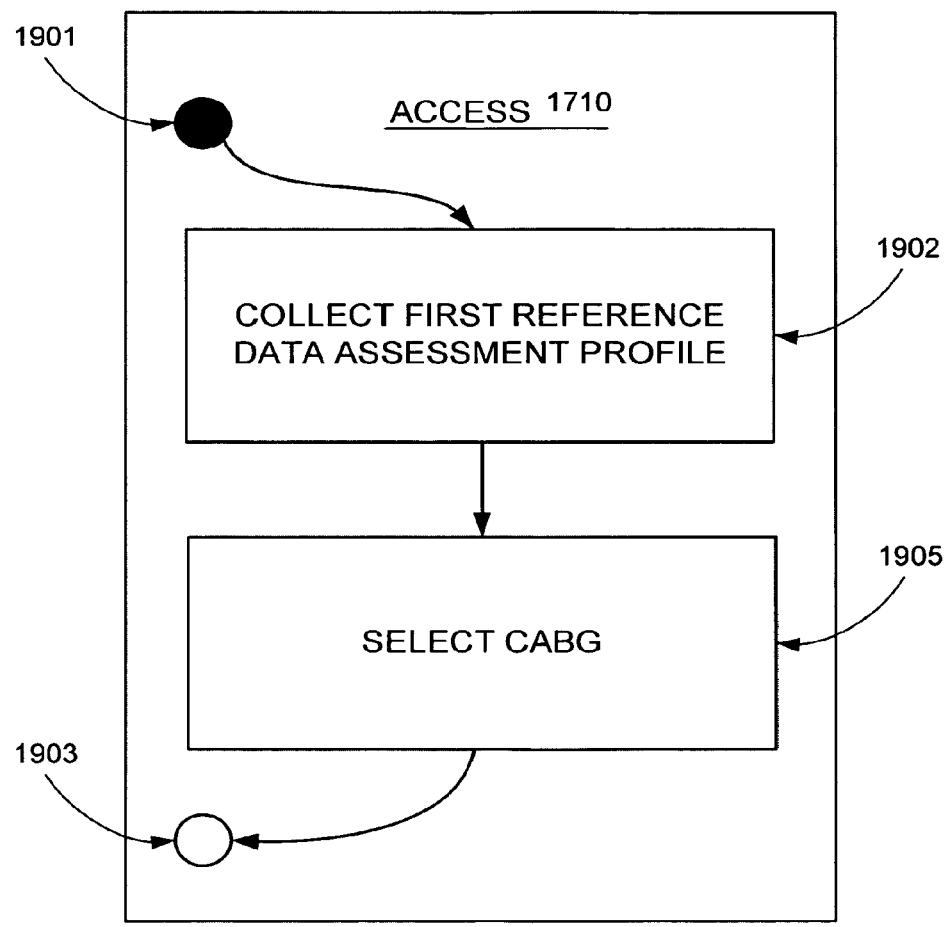
FIG. 19 is a flow chart illustrating additional detail with respect to FIG. 17.

FIG. 19 shows a flow chart illustrating step 1710 of operation 1700, in accord with one methodology. Step 1710 commences through entry point 1901. Processor 1504 may collect the first data assessment profile of the first group of patients, in step 1902. Processor 1504 may select the CABG revascularization procedure, in step 1905. Step 1710 exits through exit point 1903.

Figure 20:
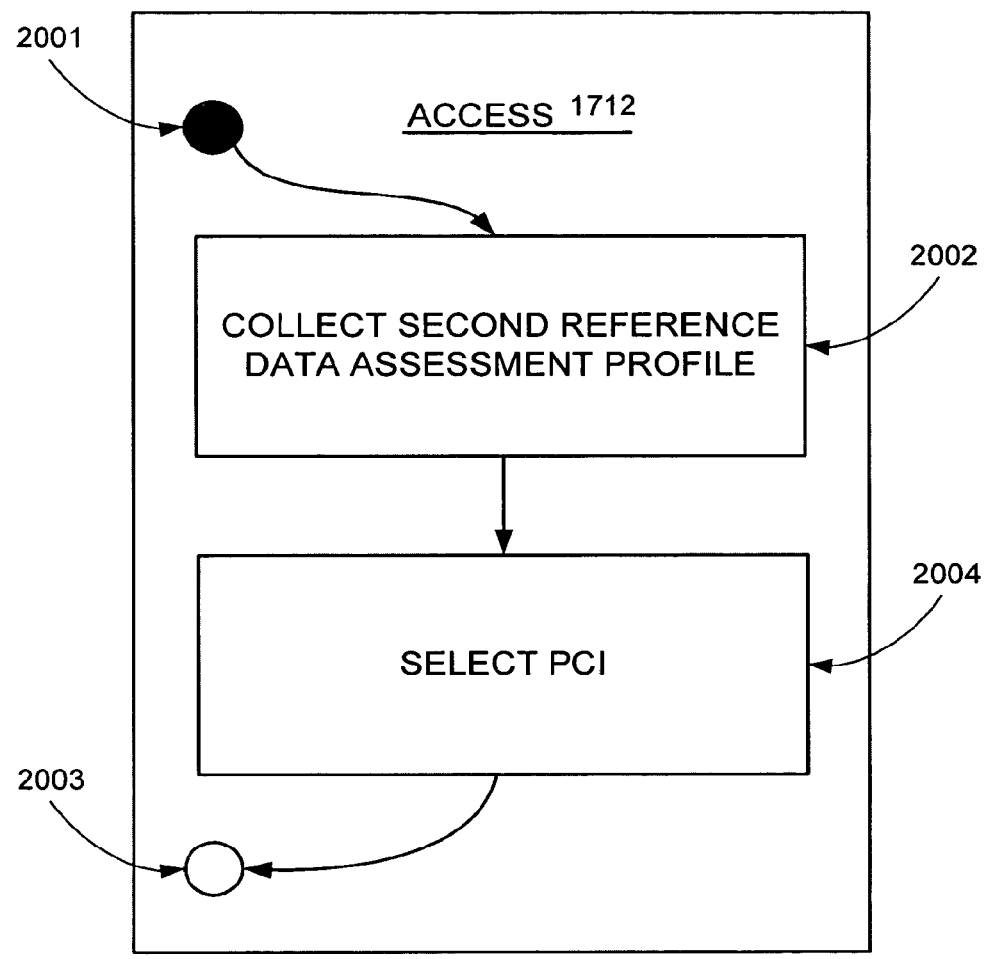
FIG. 20 is a flow chart illustrating additional detail with respect to FIG. 17.

FIG. 20 shows a flow chart illustrating step 1712 of operation 1700, in accord with one methodology. Step 1712 commences through entry point 2001. Processor 1504 may collect the second data assessment profile of the second group of patients, in step 2002. Processor 1504 may select the PCI revascularization procedure, in step 2004. Step 1712 exits through exit point 2003.

Figure 21:
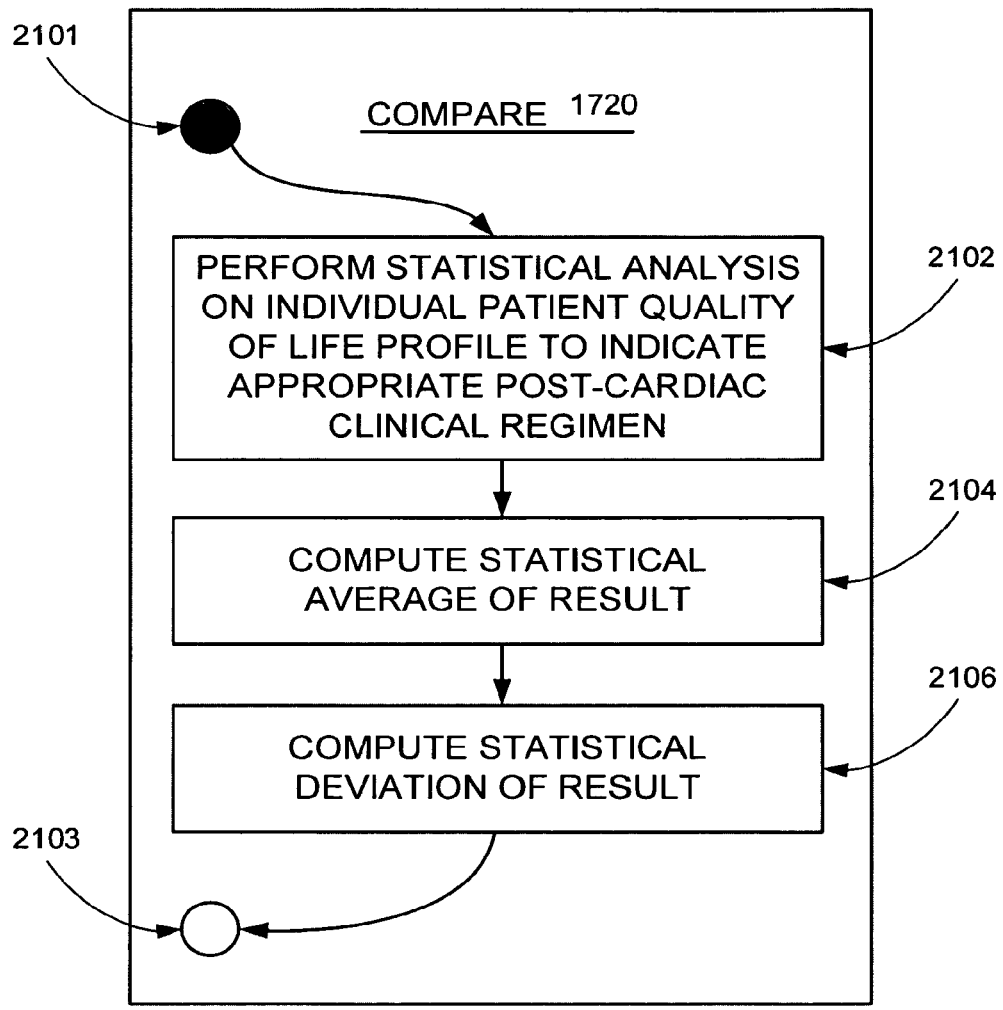
FIG. 21 is a flow chart illustrating additional detail with respect to FIG. 17.

FIG. 21 shows a flow chart illustrating step 1720 of operation 1700, in accord with one methodology. Step 1720 commences through entry point 2101. Processor 1504 may perform a statistical analysis on the individual patient quality of life profile, in step 2102. Then from the subset of the group data statistical analysis may indicate to the individual patient an appropriate post-cardiac clinical regimen. Processor 1504 may compute a statistical average that indicates the appropriate post-cardiac clinical regimen based on the statistical analysis, in step 2104. Processor 1504 may compute a statistical deviation about the average, in step 2106. Step 1720 exits through exit point 2103.

Figure 22:
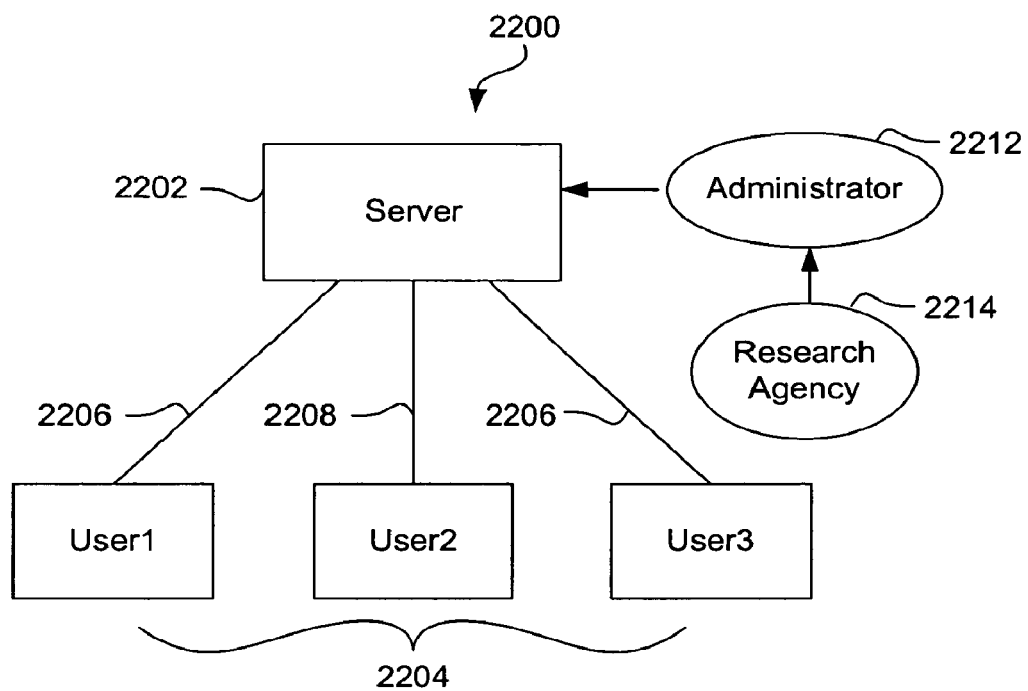
FIG. 22 illustrates an intranet of medical evaluation system users connected to a local server which permits the users to share information.

FIG. 22 illustrates an intranet system 2200 including a server 2202 that may be configured with program instructions and data to implement the foregoing instrumentalities, such as the process 100 of FIG. 1, the medical system 1000 of FIG. 10, operation 1100 of FIG. 11, operation 1600 of FIG. 16, and/or operation 1700 of FIG. 17. Intranet system 2202 may, for example, be a proprietary local area network or a wide area network. Server 2202 is connected with a plurality of users 2204 who are able to access the server 2202 for statistical processing of information. Connections 2206, 2208, and 2210 may be any type of data connection including wireless connection, coaxial connection, optical connection, Internet connection, or other type of connection across any geographic area. The intranet 2200 may be implemented in a local hospital or in a plurality of local hospitals across a city, a state, a nation, or countries throughout the world. The users 2204 are each provided with suitable electronic equipment for establishing these connections, such as a personal computer or PDA. This equipment is preferably adapted for compatibility with other extant systems, such as billing systems, patient information systems, emergency response systems, and barcoding identification and tracking systems for patients and materials.

The server 2202 may, for example, store group data 1010 and/or may provide back-up storage for individual medical evaluation systems 1400, as discussed above. Additionally, server 2202 may provide a local agent or translator for a plurality of individual medical evaluation systems 1400 to exchange information.

Server 2202 provides centralized control under the supervision of an administrator 2212. A research agency 2214 generates statistical models of any type that may relate validated statistical models with human responses to status questionnaires for any purpose. For example, the statistical model may be used to provide a prognostic indication of a health outcome or to assist a patient in selecting a therapeutic modality, as described above. The program instructions configuring server 2202 for use towards these ends are capable of accepting new models for different purposes, where these models are provided by the research agency 2214. In this manner, the research agency is able to provide updates to existing models that have been revalidated and/or expanded by comparing outcomes and demographics to survey responses. Additionally, the research agency may provide new models that may be selected by users 2204 to meet a particular need in the intended environment of use. One benefit of the administrator 2212 using the services of research agency 2214 is that the server 2202 receives the benefit of extremely specialized expertise in the creation, validation, and maintenance of the statistical models and questionnaires. For example, it is a usual business reality that a single hospital deploying intranet 2200 would not have internal access to this level of expertise. Services of the research agency 2214 may, for example, be contracted for on a subscription basis or an access basis.

Figure 23:
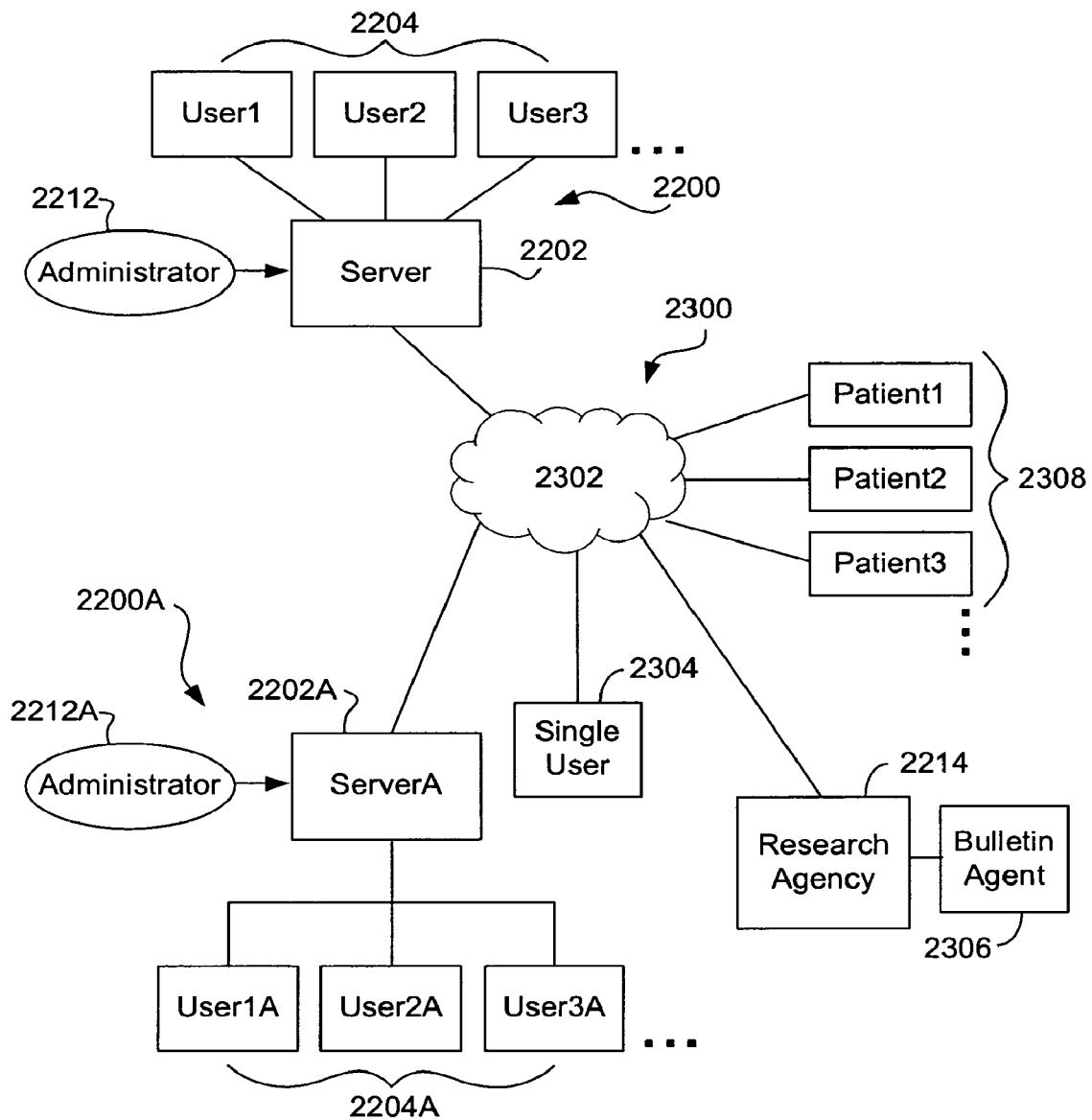
FIG. 23 illustrates an internet of medical evaluation system users connected to a website server which permits the users to share information.

FIG. 23 illustrates an Internet system 2300, which is one embodiment of Intranet system 2200 shown in FIG. 22. Research agency 2214 provides the aforementioned services to one proprietary intranet 2200, as describe in context of FIG. 22, and to a different proprietary intranet 2200 which is identical to intranet A, as well as any number of other proprietary intranets (not shown). Access to research agency 2214 is provided via the Internet 2302. A single user 2304 may also access research agency 2214, for example, from a geographically isolated medical clinic in a rural area. Internet system 2300 enables a user community, such as users associated with intranet 2200, 2200A, and user 2304 to access a bulletin agent 2306 in sharing information, such as experiences, cautionary warnings, feedback, and observations. Research agency 2214 may choose to respond to this flow of information by updating and disseminating program instructions and/or statistical models among the user community, as the need arises. In some configurations of the present invention, servers 2200A are operated by an intermediary agency, and users 2204A and 2304 communicate with a server 2200A via a local network, an intranet, or via the Internet or other public or private, wired or wireless network. In turn, server 2200A communicates with server 2202.

One benefit of Internet system 2300 is that the user community may assist and facilitate research and/or statistical validation efforts on behalf of the research agency 2214. For example, if a new statistical model is published in a scientific paper, the research agency may be provided access to a pool of demographic and health outcome information stored in the respective intranets 2200 and 2200A. This data may be used to improve the statistical model and/or expand the model-such as by inverting the model to create a prognostic tool.

An optional feature of Internet system 2300 is to provide direct monitoring of a plurality of patients 2308. Each patient may use a personal computer to periodically access one of server 2202, 2202A, or research agency 2214 for processing of health questionnaire responses. Computer-assisted processing of these responses according to a system of expert rules, for example, as defined by a cardiologist or made in reference to documented risk factors, may provide a reply to the patient indicating a recommendation. A patient may be informed of an increased risk or change in status.

In some configurations, a method for supplying information using, for example, an Internet or other networked system 2300 includes operating, or contracting with an agent to operate server 2202 to communicate via one or more networks (in this example, the Internet 2302) with a research agency 2214 and an intermediary agency (not explicitly shown in the figures, but an agency operating server 2200A, for example). In addition, the method further includes contracting with research agency 2214 to supply to server 2202, via at least one of the networks (e.g., 2302), statistical models each using one or more parameters. The models are configured, for example, to determine statistical outcomes of at least one course of procedure, for example, bypass surgery. Other examples of models are those configured to determine outcomes of non-treatment, and those configured to determine risks of developing a pathological condition later in life. The method further includes contracting with the intermediary agency for the intermediary agency to receive, on request from the intermediary agency (e.g., via its server or servers 2200A via at least one of the networks, e.g., 2302), parameter lists with reduced redundancy sufficient to apply the requested statistical models to produce model results, and with default values of parameters when such default values are available. By "reduced redundancy," it is meant herein that, where common parameters exist between a plurality of models, and/or where functions of one or more parameters completely determine the values other parameters (e.g., birthday and either age or "years since 40th birthday"), only one request for the same parameter is made and/or parameters not required because they are determinable from other parameters are not requested.

The intermediary agency is also contracted to receive and reformat the parameters list and default values, when available, for retransmission to end users (e.g., 2204A, 2304) or their agents as queries, to transmit information received in response to the queries to server 2202 for processing the requested models, to receive statistical results from the models (at server 2200A, for example), and to reformat the results and transmit the reformatted results to end users 2204A, 2304 or their agents.

In some configurations of the present invention, the operator of server 2200A or the operator's agent performs the functions contracted to the research agency and/or intermediary agent, thus eliminating the need for the research agency and/or intermediary agent and their respective contracts. For example, a system may be used to deploy the operator's own models either directly to physicians over the Internet or other public or private, wired or wireless network, or published as (for example) XML web services for consumption of third party vendors.

In some configurations of the present invention, contracting with the research agency further includes contracting with the research agency to supply updated models to server 2200 at mutually agreed-to intervals. The intervals need not be periodic. For example, the intervals may be aperiodic or defined by the occurrence of an event, such as the publication of a new model or the availability of a predetermined number of statistical observations.

In some configurations, contracting with the intermediary agency includes agreeing to provide structured lists of parameters and default values (e.g., XML-formatted lists or lists formatted in another structured form, e.g., comma, space, tab, and/or line break delimited data or tables or data and/or tables delimited in another specified manner), when default values are available. The contract can also include the intermediary agency agreeing to provide reformatted results embedded in a format customized dependent upon which of end users 2204A, 2304 or their agents is to receive the reformatted results. For example, end users 2204A may work at a different hospital or clinic than user 2304, and thus receive a result which, when printed, includes a different letterhead or contact information. In some configurations, the customized format is an informed consent agreement between a medical provider and a medical patient.

In some configurations, end users 2204A, 2304 are medical providers, patients, purchasers, payers, or combinations thereof (The term "end users or their agents" is intended to encompass these entities and combinations thereof.) Also, the courses of procedures modeled include at least one of medical procedures, medial treatments, medical procedures combined with medical treatments, and refraining from both a medial treatment and a medical procedure (i.e., doing nothing medical to treat a condition).

In some configurations of the present invention, contracting with the research agency includes agreeing that the research agency will provide access to a medical database of information relating to specific patients to allow default values of parameters to be obtained. Also, in some configurations, contracting with the intermediary agency includes agreeing that the intermediary agency will transmit medical data relating to specific patients back to server 2202 and allow the medical data to be provided as default data when a subsequent request is received at the server regarding the specific patient, and this configuration also includes transmitting the default parameter data from server 2202 to the intermediary, e.g., to the intermediary agent's server 2200A.

Some configurations of the present invention include, before sending, to the intermediary agency via at least one of the networks (e.g., Internet 2302), parameter lists with reduced redundancy sufficient to apply the requested statistical models to produce model results, analyzing the request from the intermediary agency to determine common parameters between the models invoked in the request and transmitting a list of parameters (to be filled in by the users and/or with default values that can be changed by users) sufficient to process a plurality of the requested models without transmitting any repeated parameter (i.e., a parameter used in more than one requested model) more than once.

In some configurations of the present invention, the contract with the intermediary agent provides that the intermediary supply HTML or WML-formatted pages to end users 2204A, 2304 or their agents, including lists of the parameters and the default values. Where at least some end users or their agents select courses of action corresponding to requested models and an outcome resulting from the course of action is achieved (whether the outcome was desired and expected or otherwise), some configurations also include contracting with the intermediary agent for the intermediary agent to receive information concerning the selected courses of action and the resulting outcomes and for the intermediary agent to transmit these results to the server (e.g., server 2202) for further analysis and model revision. The further analysis and model revision may be performed in some configurations after a transmission of the results from server 2202 to research agency 2214 and be performed by research agency 2214. Thus, in some configurations, contracting with the research agency further includes contracting for research agency 2214 to receive information concerning the selected courses of action and the resulting outcomes via server 2202, for example, and for the research agency to analyze and revise models using the received information concerning the selected courses of action and the resulting outcomes, and to transmit the revised models to server 2202.

Also in some configurations, a method for risk-stratifying individual patients is provided that includes contracting with a research agency 2214 for research agency 2214 to create statistical health models configured to provide model results including patient risk assessments using health query responses, health parameter data, or both. The method also includes operating a server 2202 to store instructions to receive requests to use the models, to distribute requests for data used by the models, and to apply a redundancy reduction procedure to the requests for data when a plurality of models are requested that pertain to a single patient, to analyze data received in response to the requests, and to transmit results from the analysis. The redundancy reduction procedure is a program or sequence of instructions that removes or reduces requests for duplicated parameters between requested models and/or requests for functions of parameters that can be calculated using only other requested parameters. The method further includes contracting with an intermediary agency for the intermediary agency to receive model requests from users 2204A, 2304, to transmit the model requests to server 2202 to, upon such request, use the stored instructions relating to the model, to disseminate reduced redundancy requests for data relating to requested models, and to transmit data received in response to the data requests to server 2202. The intermediary is also contracted to receive the transmitted results from the analysis, and to format said results from the analysis for transmission to users 2204A, 2304. In some configurations, this method further includes contracting with research agency 2214 to update the models and/or contracting with research agency 2214 to expand the statistical model to accommodate additional health outcomes. Also, some configurations include contracting with research agency 2214 to supply models for a plurality of diseases.

In yet additional configurations, the present invention includes a statistical processing system that includes a server 2202 operably configured with program instructions implementing a plurality of statistical models to at least one of (a) predict a health outcome based on questionnaire responses, (b) assist a patient's choice of therapeutic modality based on questionnaire responses, and (c) assess a health risk or status based on questionnaire responses. The system further includes a research agency 2214 communicating with server 2202 and contracted to provide the statistical models using a visual interface communicated by server 2202. Server 2202 is configured to analyze requests received from users 2204 over the Internet 2302, an intranet, or another network that relate to a plurality of the statistical models and to reduce redundancy in requests for patient data. Also, in some configurations, the statistical processing system further includes server 2202 operatively configured to present medical information questions to a user 2204 for human response and for receiving human responses to the medical information questions. Further, in some configurations, the statistical processing system has program instructions that are configured to assign a percentage range associated with likelihoods of encountering adverse outcomes.

In some configurations of the present invention, contracts are not issued to separate research agency and/or a separate intermediary agency, and the operator of server 2202 or a related party performs the functions of either or both of the separate agencies. For example in some configurations, the operator of server 2202 provides, in server 2202, statistical models each using one or more parameters, the models configured to determine statistical outcomes of at least one course of procedure or of non-treatment, or risks of developing a pathological condition later in life. The intermediary agency is contracted as described above. In some other configurations, the research agency is contracted as described above, but the functions described above as being contracted to the intermediary agency are performed by the operator of server 2202. These functions do not necessarily require communication with users via remote servers (such as 2202A) connected to a network (i.e., the functions can be performed by server 2202 in some configurations), but the operator can do so if desired. For example, in some configurations of the present invention the operator operates, or contacts with an agent to operate a server to communicate via one or more networks with a research agency and with either end users or their agents. This method also includes contracting with the research agency for the research agency to supply to the server, via at least one of the networks, statistical models each using one or more parameters, wherein the models are configured to determine statistical outcomes of at least one course of procedure or of non-treatment, or risks of developing a pathological condition later in life. The operator receives, via at least one of the networks, requests for use of the statistical models and constructs parameter lists with reduced redundancy sufficient to apply the requested statistical models to produce model results and with default values of parameters when such default values are available. These reduced redundancy parameter lists and default values, when available, are transmitted to end users or their agents as queries. The operator receives information in response to the queries for processing in the requested models, and transmits statistical results of the models to the end users or their agents.

It will be appreciated that patient outcomes following clinical procedures selected with the assistance of system 1700 may be monitored by the medical evaluation system 1400, for example, using the Seattle Angina Questionnaire (SAQ) and the Kansas City Cardiomyopathy Questionnaire (KCCQ). The patient self assessment data from these questionnaires may be used as feedback into system 1700 to facilitate better selections of clinical procedures, e.g., to assess the statistical likelihood of accomplishing the patient's desired goals from the clinical procedure. By way of example, one procedure versus another may have a different level of mortality risk that might be incurred for relatively small benefit. The patient would be able to assess whether the benefit of the riskier procedure is worth taking that risk. The patient might also be told, for example, what percentage of patients in their position of selecting a particular clinical procedure, with analogous goals, were ultimately satisfied with the selected procedure in terms of accomplishing the intended goals, or what percentage in hindsight would select a different procedure.

Figure 24:
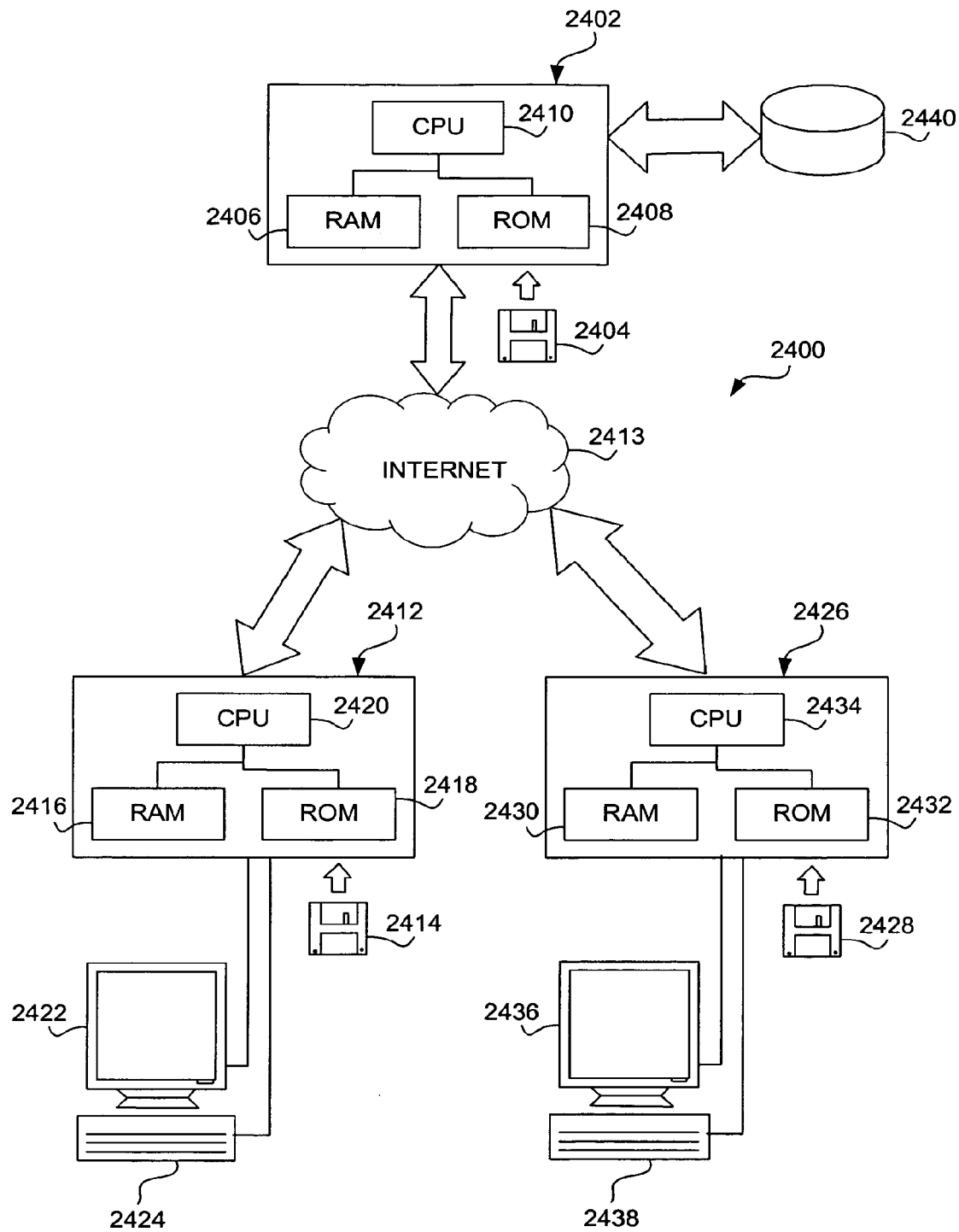
FIG. 24 is a pictorial block diagram of a configuration of a computer network of the present invention.

Other technical effects of configurations of the present invention include the generation of visual displays and printed reports useful for decision making in various fields. Thus, In some configurations of the present invention and referring to FIG. 24, a computer network 2400 is configured for providing decision support. Decision support computer network 2400 may be used, for example, in a medical or clinical health care environment to identify an appropriate regimen for treatment of a medical condition. However, uses for computer network 2400 are not limited to the health field. To give but one of many examples, decision support computer network 2400 is useful in an advertising environment to determine strategies for marketing products. More generally, computer network 2400 is useful in many varied contexts in which statistical regression models can be used to predict outcomes.

In some configurations, computer network 2400 comprises a server computer 2402 that executes a server module. The server module comprises software instructions recorded on a machine-readable medium or media 2404. The machine readable medium or media may comprise, for example, one or more floppy diskettes, CD-ROMs, CD-RWs, DVDs, DVD+Rs, DVD-Rs, DVD+RWs, DVD-RWs, memory devices such as USB memory sticks or other types of memory cards, internal readable and writable memory 2406 of any of various kinds, such as internal or external RAM, etc., read-only memory (ROM) 2408 of any of various kinds, hard disks, optical drives, and combinations thereof. (As used herein, "media" includes not only "removable" media, but also "non-removable" media such as primary and secondary storage. For example, RAM, ROM, and hard disk drives are included as "media," as well as the aforementioned types of media.) Server computer 2402 can include devices (not specifically illustrated in FIG. 24) for reading removable media, such as a CD-ROM drive, a DVD drive, a floppy disk drive, etc. In many configurations, server computer 2402 will comprise at least a readable and writeable memory 2406, read-only memory 2408 or non-volatile memory of a suitable type, and a processor 2410 (e.g., a central processing unit or CPU) which may itself comprise one or more microprocessors, coprocessors, etc. Thus, the term "processor," as used herein, is not literally restricted to a single CPU. Moreover, server computer 2402 may itself comprise a network of one or more computers, as can any other device referred to as a "computer" herein.

Computer network 2400 further comprises one or more first client computers 2412. In many configurations, it is in communication with server computer 2402 via a network 2413, for example, the Internet. In many configurations of the present invention, Client computer 2412 comprises a first client module comprising software instructions recorded on a machine-readable medium or media 2414. In many configurations, client computer 2412 further comprises at least a readable and writable memory 2416, read-only memory 2418, and a processor 2420 that may itself comprise one or more microprocessors, coprocessors, etc. First client computer 2412 may itself comprise one or more computers in a network. First client computer 2412 further comprises a first user display device 2422, such as a CRT display, LCD display, plasma display, and/or a hardcopy device such as a printer. First client computer 2412 also comprises a first user input device 2424, such as a keyboard, a mouse, a touch screen (which may be part of display 2422), and/or a trackball, etc.

Computer network 2400 further comprises one or more second client computers 2426. In many configurations, second client computer 2426 is in communication with server computer 2402 via network 2413. Also in many configurations, second client computer 2426 comprises a second client module comprising software instructions recorded on a machine-readable medium or media 2428. In many configurations, second client computer 2426 further comprises at least a readable and writable memory 2430, read-only memory 2432, and a processor 2434 that may itself comprise one or more microprocessors, coprocessors, etc. Second client computer 2426 may itself comprise one or more computers in a network. Second client computer 2426 further comprises a second user display device 2436, such as a CRT display, LCD display, plasma display, and/or a hardcopy device such as a printer. Second client computer 2426 also comprises a second user input device 2438, such as a keyboard, a mouse, a touch screen (which may be part of display 2436), and/or a trackball, etc.

As used herein, software instructions are said to "instruct a computer to display" information even if such information is communicated via a network to another computer for display on a remote display terminal. In this sense code running on a web server instructs a processor executing that code to "display" a web page, even though the code actually instructs the processor to communicate data via a network that allows a browser program to instruct another computer to construct a display of the web page on the display of the other computer. For example, the server module described in the examples presented herein can include a web server and the client modules can comprise web browsers. Also, in some configurations, client computers 2412 and 2426 comprise laptop, desktop, or mobile computing devices or communication terminals. The broader scope of the phrase "instruct a computer to display" is used because server computer 2402 and the one or more client computers 2412, 2426 need not necessarily be different computers. For example, communication protocols known in the art allow a server software module and a client software module running on a multitasking computer system to communicate with one another on the same computer system, and the same server software module can also communicate with a client software module running on a different computer via a network connection. The examples used herein assume, without loss of generality, that different physical computers and a network are used, as such will be the case in many, but not all, configurations of the present invention.

The terms "display" and "accept" as used in the descriptions herein refer to a suitably programmed computing apparatus "displaying" or "accepting" data, not to a person "displaying" or "accepting" something. A person might, however, view the displayed data on an output device or on a page produced by an output device or supply the accepted data using an input device.

In some configurations of the present invention, a method is provided to provide decision support via software that comprises the server module. Some configurations of the present invention provide server modules that utilize the ASP.NET platform available from Microsoft Corporation as well as MS Internet Information Services (IIS) and MS SQL Server from Microsoft Corporation for web services and data storage, respectively. A multi-tier system architecture provided in some configurations enables scaling of server module components as needed to meet specific demands of a particular deployment. In addition, a modular design framework is provided in some configurations to facilitate extensibility and incorporation of new functionality via custom modules. In some configurations, the server module is written in C# using the code-behind convention; except for its SQL data access components which are stored procedures written in Transact-SQL.

Figure 25A:
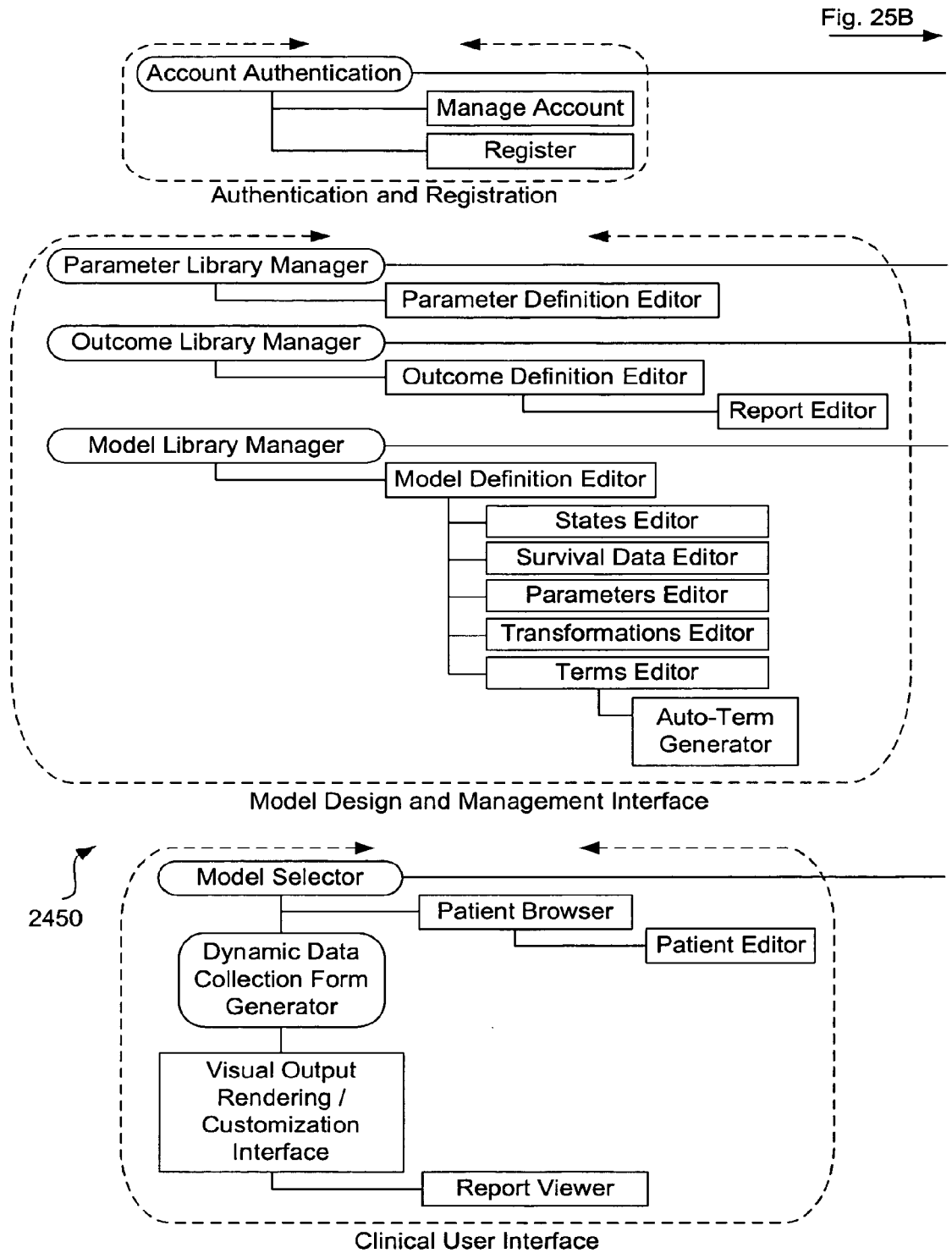
FIG. 25 is a block diagram showing the logical structure of an example configuration of a server module.
Figure 25B:
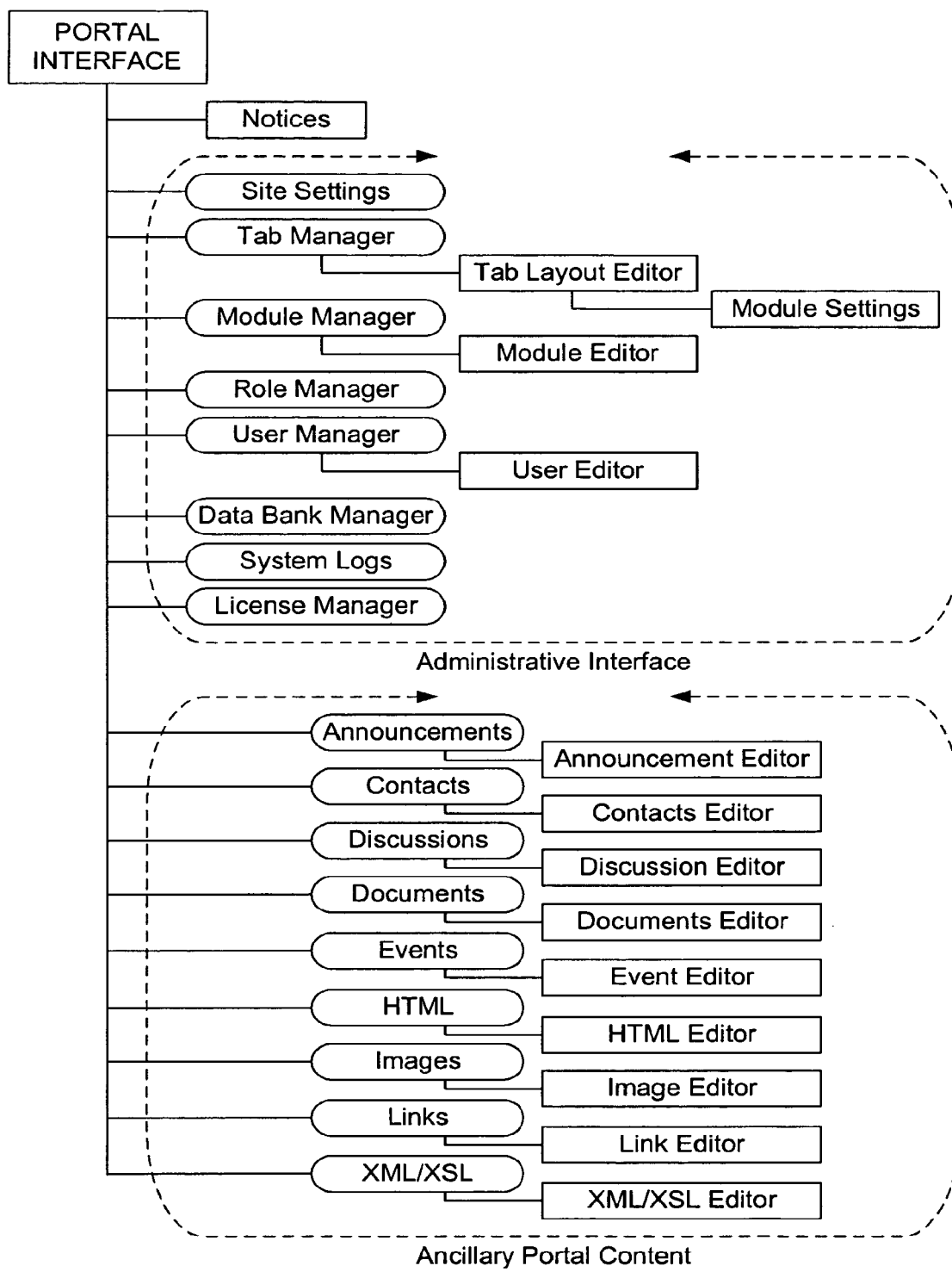
Figure 26:
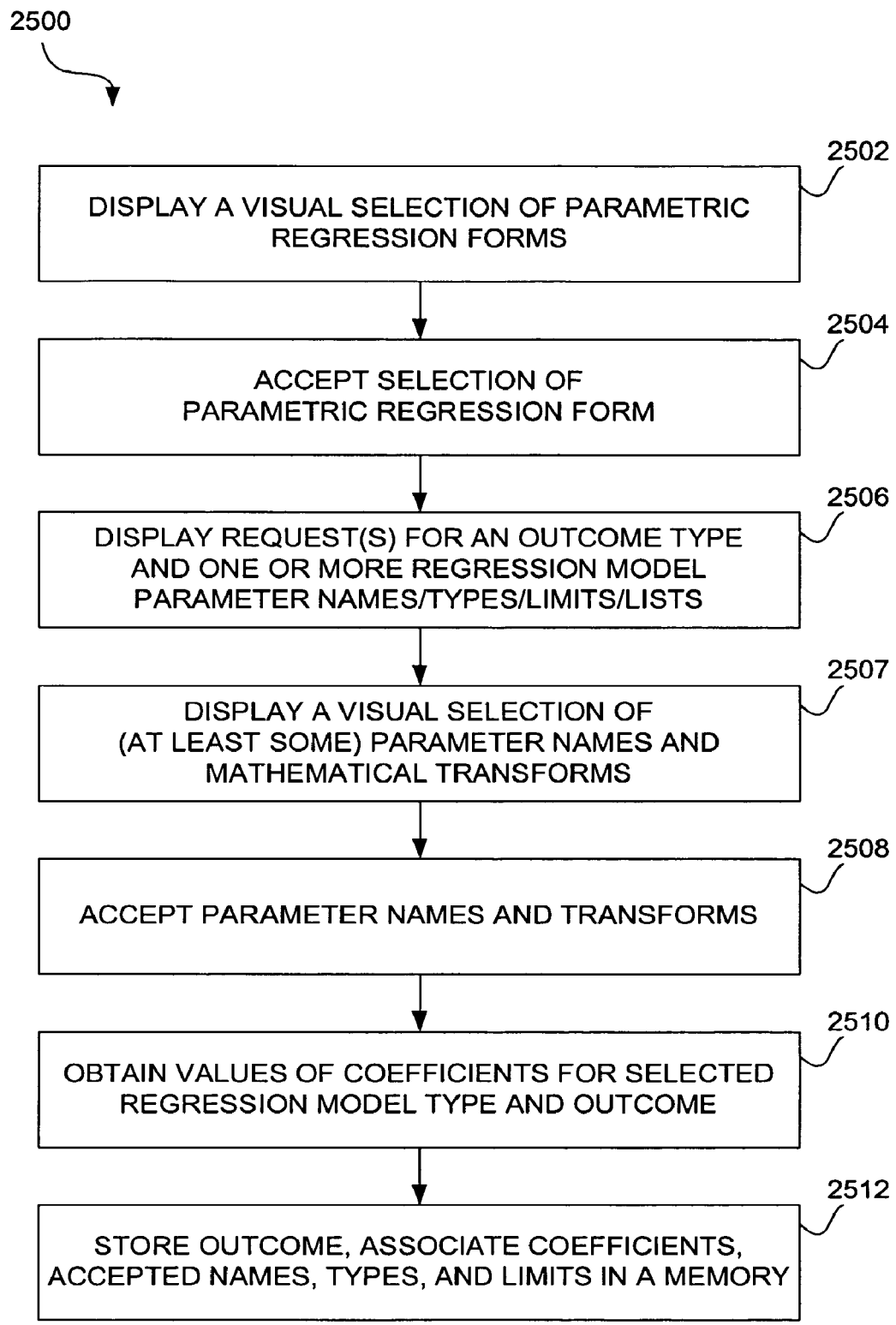
FIG. 26 is a flow chart illustrating instruction steps provided by some configurations of the server module of FIG. 25 in some configurations of the present invention.

More particularly, and referring to FIGS. 25 and 26, a server module 2450 is provided on a machine readable medium or media. In some configurations of the present invention, server module 2450 instructs processor 2410 to perform a method illustrated by flow chart 2500 of FIG. 26. Although the flow charts provided herein are illustrative of configurations of methods used herein, it will be understood that the order of steps shown can be varied from the order illustrated in other configurations of the present invention, that steps illustrated as being separate can be combined (e.g., various displays and requests for data can be combined into a single output screen), and that not all steps illustrated are necessarily required in all configurations.

A technical effect is achieved first by a user logging in with appropriate credentials. Server module 2450 instructs processor 2410 to display, at 2502, a visual selection of parametric regression model forms (on user display device 2422, for example). (An example of such a display is shown in FIG. 27.) A general regression model framework is used for expressing predictions. The model types can include, for example, linear, generalized linear, cumulative multinomial, generalized multinomial and proportional hazard models, thereby providing coverage for major medical prognostic model types. For example, the selection may include a linear regression model of the form $f(x)=\beta_1 x_1 + \beta_2 x_2 + \beta_3 x_3 + \ldots + \beta_n x_n$ as well as intrinsically non-linear forms and forms that are linear in transformed variables, e.g., $x_1 = \ln(y)$, where y is an input variable. Some configurations provide the ability to implement custom model types using a built-in scripting interface. The visual display of model type is associated with a drop-down list in some configurations, for example, and the visual display of model type changes depending upon the item selected from the drop-down list.

Model types are defined in terms of a coefficient vector and an optional covariance matrix for calculating confidence intervals. For example, the coefficient vector and covariance matrix are defined as follows:

In the definitions above, $b_i' = (b_{i1} b_{i2} \ldots b_{is})$ is the vector of coefficients associated with the $i^{th}$ predictor in x, with one coefficient for each state s (except the reference state). Also, $V_{ikjl} = \text{Cov}(b_{ik}, b_{jl})$ denotes the covariance between the ($i^{th}$ predictor, $k^{th}$ state) and ($j^{th}$ predictor, $l^{th}$ state) coefficients.

The user at client computer 2412 enters a selection of a model type (for example, a selection of one of the following model types: linear, generalized linear, cumulative multinomial, generalized multinomial or proportional hazard model) from a visual menu. ("Visual" displays and menus include one or more elements such as graphical illustrations, drop-down lists, selection buttons, checklists, etc.) Server computer 2402 is programmed with instructions by the server module to accept this selection at step 2504. Next, at step 2506, instructions in the server module instruct processor 2410 to display a request or requests for an outcome type and one or more regression model parameter names (e.g., in a medical or surgical environment, "blood pressure," "diabetes," "ejection fraction," and/or other statistically significant parameters) and corresponding parameter types (for example, and not necessarily in correspondence to the example parameter names, "binary," "enumerated," "positive integer," "decimal," etc.) and, in appropriate cases, limits and/or lists of possible input values. An example of an outcome type screen is shown in FIG. 5 and an example of a parameter name screen is shown in FIG. 29. At step 2507, some configurations of the present invention also display a visual selection of at least some of the parameter names along with a visual selection of mathematical transforms for each displayed name. The user selects a transform, which can include, for example, logarithms, exponentials, squares, square roots, and other transformations, so that these functions of the values later used for each corresponding variable name are used in the regression equation instead of the variables themselves.

At step 2508, these names, types, limits and/or transforms are accepted by processor 2410. At step 2510 (which may be combined with step 2508), values of the coefficients for the selected regression model type and outcome are obtained. In some configurations, these values are obtained by requesting that they be input by a user at first client computer 2412. In other configurations, they are obtained by instructions to processor 2410 to run a regression analysis on data obtained from a database 2440, which may be a local database stored in computer 2404 or a database accessible via a network such as network 2413. The outcome, associated coefficients and accepted names, types, and limits for variables are stored in a memory (e.g., memory 2406 or a secondary storage unit) of server computer 2406 at step 2512.

In some configurations, the procedure represented by flow chart 2500 can be repeated when necessary to add further outcome models representing different combinations of variables for different procedures, such as medical or surgical procedures. Some configurations further allow the editing and/or deletion of stored models.

Figure 30:
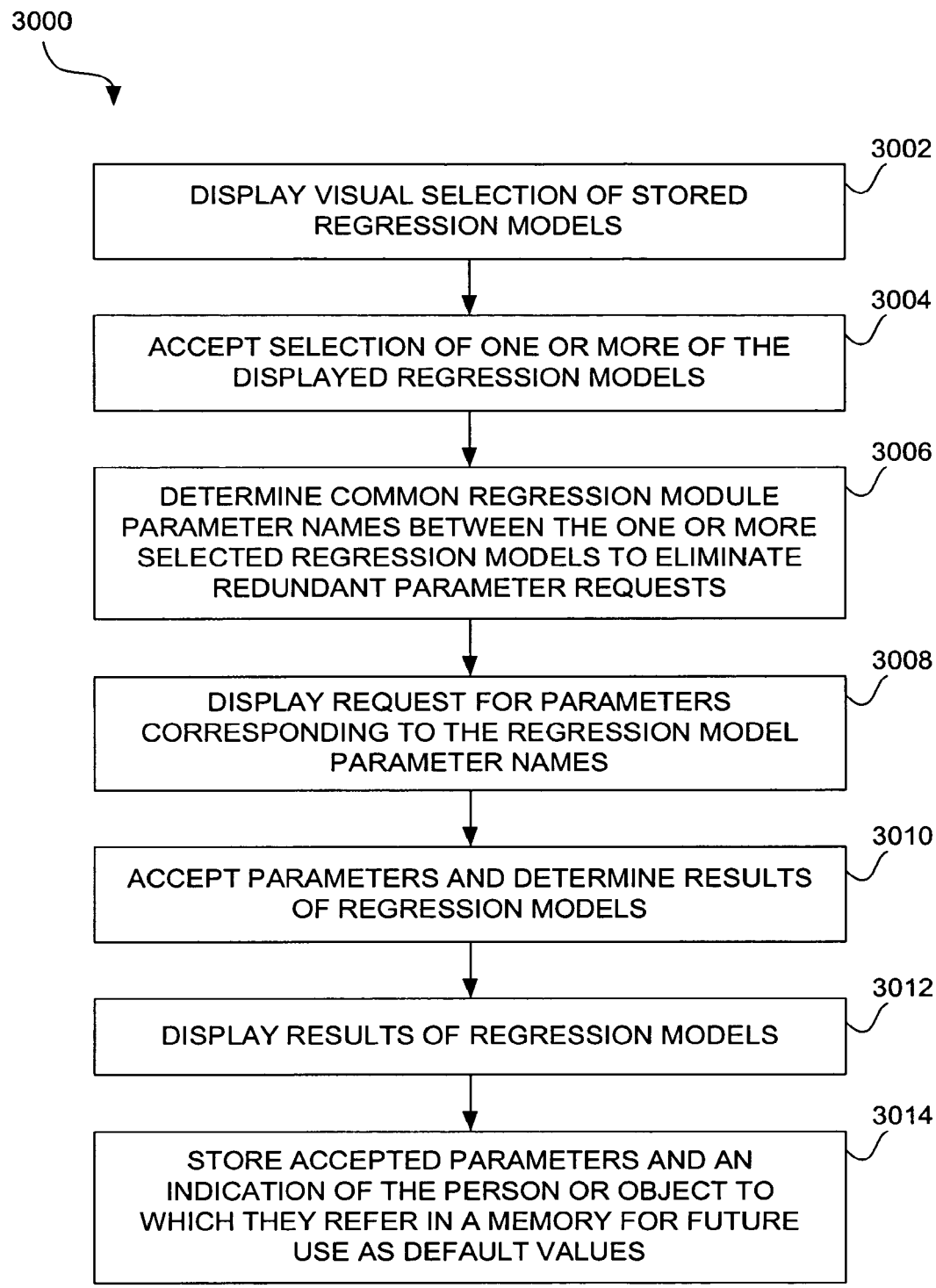
FIG. 30 is a flow chart illustrating additional instruction steps provided by some configurations of the server module of FIG. 25 in some configurations of the present invention.

Referring next to flow chart 3000 of FIG. 30, server module 2450 also contains instructions configured to instruct processor 2410 to allow a user (usually different from the user at first client computer 2412) at second client computer 2426 is logged into the server module. The user at second client computer 2426 is able to select one or more of the stored models, input data corresponding to the stored models, run a regression analysis and be presented with results of the regression analysis or analyses. More particularly, at step 3002, processor 2410 is instructed to display a visual selection of previously stored regression models on second user display device 2436 by communicating data via network 2413 with a program (e.g., a web browser) running on second client computer 2426. An example of a display that provides a visual selection of previously stored models is shown in FIG. 31. A user at second client computer 2426 uses second user input device 2438 to indicate a selection of one or more of the displayed regression models, which is communicated to processor 2410 via network 2413, and processor 2410 is instructed to accept this selection at step 3004. At step 3006, the server module determines common regression module parameter names between the one or more selected, stored regression models so that redundant requests for parameters can be eliminated or reduced. By a "reduced redundancy" of parameters, it is meant herein that common parameters between models and/or parameters that are functions derivable from other parameters, do not result in an unnecessary plurality of requests for similar data.

Figure 33:
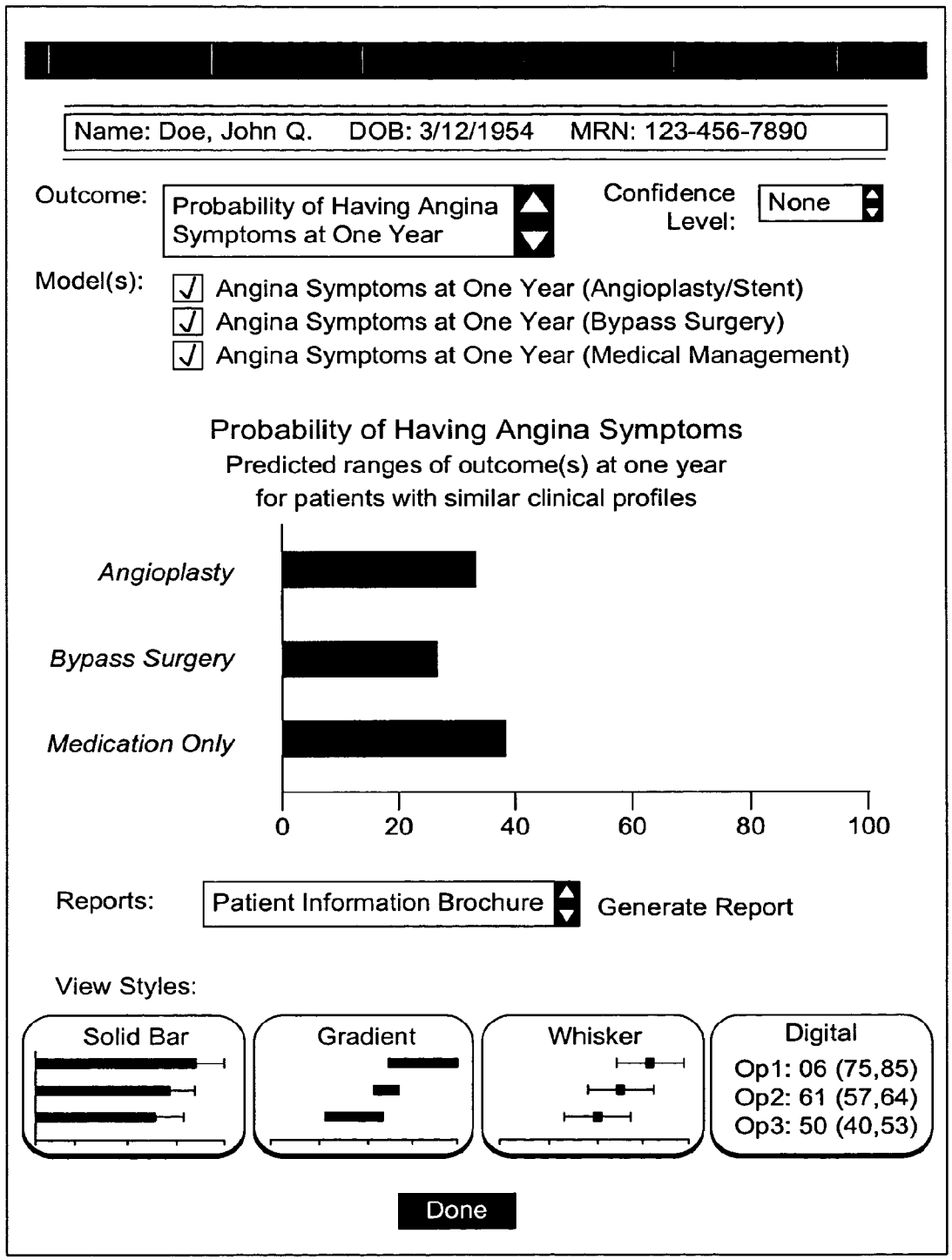
FIG. 33 is an example of a result display provided by some configurations of the present invention.

Thus, at step 3008, the server module displays a request or requests for parameters that correspond to the regression model parameter names in the set of all such names stored for all the selected regression models at step 3004. An example of such a displayed request is shown in FIG. 32. The server module accepts the collected parameter data at 3010 (which may also include an identification of a person or object to which the parameters apply) and runs the selected regression models. At step 3012, results of the selected regression models are displayed. An example of such a display is shown in FIG. 33. The displayed results can also include a visual representation of a statistical range. In some configurations, at step 3014, processor 2410 is instructed to use customizable letterhead data, previously stored in a memory or database accessible to processor 2410 and optionally including return addresses, logos, etc. to print the results or to cause the results to be printed. The server module can include instructions to print different letterheads depending upon credentials (e.g., login information) provided by the current user. Also, in some configurations, instructions to processor 2410 at step 3016 cause processor 2410 to store parameters accepted at step 3010 and an indication of the person or object to which the parameters apply in a memory or database (such as memory 2404) accessible to processor 2410. Instructions in the server module are provided to instruct processor 2410 to provide default values for the stored parameters when outcome results of the same or different type are requested for that person or object at a different time.

More particularly, at runtime, collected model parameters (i.e., user inputs) are serialized into a Predictor Vector:

$$x' = (x_1 \; x_2 \; \ldots \; x_r) = \begin{cases} (1 \; z') & \text{Intercept} \\ z' & \text{No Intercept} \end{cases}$$

where z is the transformed response vector, each of whose elements correspond to a single data item (e.g., systolic blood pressure).

The Linear Predictor is then calculated as $$\hat{\eta}' = (\hat{\eta}_1 \hat{\eta}_2 \ldots \hat{\eta}_s) = (x'(e_1 \circ b) x'(e_2 \circ b) \ldots x'(e_s \cdot b))$$

in which each $e_i$ is an extraction vector derived from the appropriate Extraction Matrix:

$$E = \begin{bmatrix} e'_1 \\ e'_2 \\ \vdots \\ e'_s \end{bmatrix}$$

where each row $e_i'$ identifies the relevant sub-vector of b and the sub-matrix of V needed to predict the $i^{th}$ independent parameter of the predictand. The exact form of E is dependent on the model type (see Table 4).

TABLE 4

Extraction Matrices

| Model Type | Intercept | No Intercept |
|---|---|---|
| Linear | $1_{1 \times (r+1)}$ | $1_{1 \times r}$ |
| Generalized Linear | $1_{1 \times (r+1)}$ | $1_{1 \times r}$ |
| Cumulative Multinomial | $[I_{s \times s} \; 1_{s \times r}]$ | $[I_{(s-1) \times (s-1)} \; 1_{(s-1) \times r}]$ |
| Generalized Multinomial | $[\underbrace{I_{s \times s} \; \ldots \; I_{s \times s}}_{r+1 \text{ times}}]$ | $[\underbrace{I_{s \times s} \; \ldots \; I_{s \times s}}_{r \text{ times}}]$ |
| Proportional Hazards | N/A | $1_{1 \times r}$ |

In the table above, I denotes the identity matrix (i.e., a matrix with all diagonal entries=1 and all off-diagonal entries=0), and 1 denotes a matrix of all 1s.

The Prediction Vector containing the outcome point-estimate(s) is then given by $$\hat{\mu} = g^{-1}(\hat{\eta})$$

where $g^{-1}$ is the appropriate inverse link function (see Table 5). The Linear Predictor Variance Vector is given by $$\hat{\sigma}'^2 = (x'(e_1 \circ V)x \; x'(e_2 \circ V)x \ldots x'(e_s \circ V)x)$$

from which confidence intervals can be calculated as:

$$(\hat{\mu}_{LO}, \hat{\mu}_{HI}) = g^{-1}(\hat{\eta} \pm F_v^{-1}(1-\alpha/2)\sqrt{\hat{\phi}^2 + \hat{\sigma}^2})$$

where $F_v^{-1}$ is the inverse t-distribution function with v degrees of freedom at confidence level $\alpha$ and $\hat{\phi}^2$ is the mean square error ($\hat{\phi}^2$ defined only for linear models).

TABLE 5

Inverse Link Functions

| | |
|---|---|
| Identity | $\mu = \eta$ |
| Log | $\mu = e^\eta$ |
| Logit | $\mu = (1 + e^{-\eta})^{-1}$ |
| Probit | $\mu = \Phi(\eta)^*$ |
| Power | $\mu = \begin{cases} \eta^{1/\lambda} & \text{if } \lambda > 0 \\ e^\eta & \text{if } \lambda = 0 \end{cases}$ |
| Complementary log-log | $\mu = 1 - e^{-e^\eta}$ |
| Cumulative logit[†] | $\pi_i = (1 + e^{-\eta_i})^{-1} \quad i = 1, \ldots, s$ |
| Cumulative probit[†] | $\pi_i = \Phi(\eta_i)^* \quad i = 1, \ldots, s$ |
| Cumulative complementary log-log[†] | $\pi_i = 1 - e^{-e^{\eta_i}} \quad i = 1, \ldots, s$ |
| Generalized logit | $\mu_i = \begin{cases} e^{\eta_i}\left(1 + \sum_{j=1}^{s} e^{\eta_j}\right)^{-1} & i = 1, \ldots, s \\ \left(1 + \sum_{j=1}^{s} e^{\eta_j}\right)^{-1} & i = s+1 \end{cases}$ |
| Proportional hazards | $\mu = S_j^{e^\eta}$ |

[†]For multi-state models, $\mu_i = \begin{cases} \pi_i & i = 1 \\ \pi_i - \sum_{j=1}^{i-1} \pi_j & i = 2, \ldots, s \\ 1 - \sum_{j=1}^{i-1} \pi_j & i = s+1 \end{cases}$

*$\Phi$ is the standard normal distribution function

In various configurations of the present invention, model building is greatly facilitated by a visual editing environment that provides dynamic on-screen instructions and rendering of prediction formulae as well as robust validation services. Parameters are identified that are used in a prediction formula. New parameters can be created de novo or selected from an existing parameter library (thereby allowing for standardization of parameter definitions across all models).

Once parameters have been defined, one or more data transformations can be assigned to each. A broad array of built-in transformation types are available to the user, and custom transformation types can be readily defined via scripting, allowing configurations of the present invention to handle a wide range of complex formulae.

Main effects and interaction terms derived from the input parameters and their transformations can be derived in some configurations of the present invention, and regression coefficients for calculating point estimates for outcome of interest and optional covariance estimates can be provided for computing confidence intervals.

Once models have been built and deployed, health care providers (or, in other environments, other individuals) can readily access them through an integrated and customizable portal interface using a variety of web-enabled devices. Dynamically generated data entry screens are provided based on the parameters required by the selected model(s). For example, in medical environments, data for patients can either be entered de novo or retrieved from a patient information system, which can be readily integrated with existing clinical information systems via XML web services support.

Some configurations of the present invention render model outputs in a variety of graphical and non-graphical formats, including solid bar plots, gradient bar plots, whisker line plots, pie charts, and/or digital LED-style displays, which can be user-selectable. Output from multiple models can be grouped onto a single plot to facilitate inter-model comparisons (for example, stroke risk with angioplasty versus bypass surgery). In addition, some configurations allow a user to customize the output plot style, the selection of models to include in a final output and the display of confidence intervals (when model covariance data has been provided). In various configurations, users can print outcome plots using customizable report templates in order to generate documents such as patient educational materials and informed consent sheets. Also in some configurations, outcomes researchers can customize report and page content using a built-in Microsoft Word®-like interface or by editing HTML code. A feature rich set of portal content modules, including workgroup directories, discussion threads, and document repositories can be provided in server module configurations of the present invention to allow outcomes research groups to easily create, manage, and build their own collaborative web sites.

It will thus be appreciated that configurations of the present invention can be used to handle various aspects of data collection, validation, storage/retrieval, and processing, thereby freeing outcomes researchers from intricacies of programming and networking so that they may focus their efforts upon implementation of their research models towards the betterment of patient care.

While the invention has been described in terms of various specific embodiments, those skilled in the art will recognize that the invention can be practiced with modification within the spirit and scope of the claims.

What is claimed is:

1. A method of utilizing a statistical health model, the method comprising:
   storing in computer readable memory associated with a statistical health model translation system a first plurality of statistical health models from respective sources in a plurality of different sources,
      wherein at least one statistical health model in the first plurality of statistical health models from the respective sources is a medical prognostic risk stratification model and/or a medical prognostic outcomes prediction model in the form of at least one of a:

linear model,
a generalized linear model,
a cumulative multinomial model,
a generalized multinomial model,
a proportional hazard model;
providing via the statistical health model translation system one or more user interfaces including a plurality of fields that enable one or more users to specify for the at least one statistical health model:
an outcome predicted by the at least one statistical health model;
one or more outcome predictors;
a mathematical relationship between:
the outcome predicted by the at least one statistical health model, and
the one or more outcome predictors;
providing via the statistical health model translation system one or more user interfaces that enable one or more users to select models from the first plurality of statistical health models for execution;
receiving a user selection of one or more of the first plurality of statistical health models;
automatically generating data-input interfaces for collecting patient-specific predictors utilized when executing the selected one or more of the first plurality of statistical health models based at least in part on the one or more outcome predictors;
processing, via a computing device, the one or more outcome predictors and information regarding a patient received via the automatically generated data-input interfaces, where the information received via the automatically generated data-input interfaces includes one or more patient medical conditions, using the selected one or more of the first plurality of statistical health models; and
providing, via the computing device, an output from the selected one or more of the first plurality of statistical health models.

2. The method of claim 1, the method further comprising providing via the statistical health model translation system a user interface including a plurality of fields configured to:
receive one or more predictor coefficients; and
receive one or more predictor coefficient covariances for calculating confidence intervals.

3. The method of claim 1, wherein the first plurality of statistical health models includes a statistical health model configured to determine a statistical outcome of a medical procedure, medical treatment or intervention, and/or medical condition with respect to the patient.

4. The method of claim 3, wherein at least one outcome includes risks associated with genetic factors or biochemical factors.

5. The method of claim 1, the method further comprising:
receiving an update to a first statistical health model of the first plurality of statistical health models from the source entity; and
storing the update in computer readable memory associated with a statistical health model translation system.

6. The method of claim 1, wherein the first plurality of statistical health models includes a statistical health model of the form:

$$f(x)=\beta 0+\beta 1X1+\beta 2X2+\beta 3X3+\beta nXn.$$

7. The method of claim 1, wherein the first plurality of statistical health models includes a statistical health model that is non-linear.

8. The method of claim 1, wherein the first plurality of statistical health models includes one or more outome predictor transforms, wherein a first of the one or more outome predictor transforms is an identity, inverse, square root, power, polynomial, exponential, logarithm, or mapping transformation.

9. The method of claim 1, the method further comprising converting at least one of the one or more statistical health model predictors into a predictor vector.

10. The method of claim 1, the method further comprising providing a web service via which a patient population database is passed through at least a first selected plurality of the first plurality of statistical health models to project disease prevalences, treatment costs, and/or resource requirements.

11. The method of claim 1, wherein the one or more user interfaces that enable one or more users to select models from the first plurality of statistical health models for execution further comprises a control via which the user can initiate the execution of all of the selected models.

12. The method of claim 1, the method further comprising:
contracting with a research agency to provide a first statistical health model to the statistical health model translation system;
contracting with a hospital to provide the hospital with access to the first statistical health model;
storing in computer readable the first statistical health model of the contracted research agency; and
electronically providing the contracted hospital with access to the first statistical health model.

13. The method of claim 1, the method further comprising providing access to a first statistical health model of the first plurality of statistical health models to a hospital.

14. The method of claim 1, the method further comprising providing reformatted results obtained via the statistical health model embedded in a format that is customized, wherein the customization is based at least in part upon which end user is to receive the results.

15. The method of claim 1, the method further comprising transmitting over a network a first output from the statistical health model to a first medical entity using a first letterhead and second output from the statistical health model to a second medical entity using a second letterhead.

16. The method of claim 1, the method further comprising providing a first output from a first statistical health model of the first plurality of statistical health models to a first medical entity in a format as an informed consent agreement, wherein the informed consent agreement is formatted based at least in part on the identity of the first medical entity.

17. The method of claim 1, wherein a first statistical health model of the first plurality of statistical health models is configured to perform at least one of the following:
predict a health outcome based on questionnaire responses,
assist a patient's choice of therapeutic modality based on questionnaire responses,
assess a health risk or status based on questionnaire responses.

18. The method of claim 1, the method further comprising providing structured lists of parameters and default values to a remote system.

19. The method of claim 1, the method further comprising obtaining values of coefficients for a first statistical health model of the first plurality of statistical health models.

20. The method of claim 1, the method further comprising receiving default values of model parameters.

21. The method of claim 1, the method further comprising transmitting to a remote client a response including HTML, WML, or XML formatting, including lists of the model parameters and default values.

22. The method of claim 1, the method further comprising transmitting to the remote system information concerning selected courses of action with respect to treating a medical condition and corresponding resulting outcomes.

23. The method of claim 1, the method further comprising receiving from the remote system patient risk assessments using health query responses and health parameter data.

24. The method of claim 1, the method further comprising providing for display a user interface configured to receive information regarding the patient and the patient medical condition(s).

25. The method of claim 1, the method further comprising providing a programmatic interface to receive information regarding the patient and one or more patient medical conditions.

26. The method of claim 1, the method further comprising providing via the statistical health model translation system one or more user interfaces that enable one or more users to specify via a plurality of defined fields:
   one or more limits and/or lists of possible input values for the one or more outcome predictors; and
   one or more transforms for the one or more statistical health model predictors.

27. The method of claim 1, the method further comprising providing, via the computing device, an output from a first statistical health model of the first plurality of statistical health models for display and/or returning an output from the first statistical health model of the first plurality of statistical health models via a programmatic interface.

28. A tangible computer-readable medium having computer-executable instructions stored thereon that, if executed by a computing device, cause the computing device to perform a method comprising:
   storing in computer readable memory associated with a statistical health model translation system a first plurality of statistical health models from respective sources in a plurality of different sources,
      wherein at least one statistical health model in the first plurality of statistical health models from the respective sources is a medical prognostic risk stratification model and/or a medical prognostic outcomes prediction model in the form of at least one of a:
         linear model,
         a generalized linear model,
         a cumulative multinomial model,
         a generalized multinomial model,
         a proportional hazard model;
   providing via the statistical health model translation system one or more user interfaces including a plurality of fields that enable one or more users to specify for the at least one statistical health model:
      an outcome predicted by the at least one statistical health model;
      one or more outcome predictors;
      a mathematical relationship between:
         the outcome predicted by the at least one statistical health model, and
         the one or more outcome predictors;
      providing via the statistical health model translation system one or more user interfaces that enable one or more users to select models from the first plurality of statistical health models for execution;
   receiving a user selection of one or more of the first plurality of statistical health models;
   automatically generating data-input interfaces for collecting patient-specific predictors utilized when executing the selected one or more of the first plurality of statistical health models based at least in part on the one or more outcome predictors;
   processing, via a computing device, the one or more outcome predictors and information regarding a patient received via the automatically generated data-input interfaces, where the information received via the automatically generated data-input interfaces includes one or more patient medical conditions, using the selected one or more of the first plurality of statistical health models; and
   providing, via the computing device, an output from the selected one or more of the first plurality of statistical health models.

29. The tangible computer-readable medium of claim 28, the method further comprising providing via the statistical health model translation system a user interface including a plurality of fields configured to:
   receive one or more predictor coefficients; and
   receive one or more predictor coefficient covariances for calculating confidence intervals.

30. The tangible computer-readable medium of claim 28, wherein the first plurality of statistical health models includes the statistical health model is configured to determine a statistical outcome of a medical procedure, medical treatment or intervention, and/or medical condition with respect to the patient.

31. The tangible computer-readable medium of claim 30, wherein at least one outcome includes risks associated with genetic factors or biochemical factors.

32. The tangible computer-readable medium of claim 28, the method further comprising:
   receiving an update to a first statistical model of the first plurality of statistical health models from the source entity; and
   storing the update in computer readable memory associated with a statistical health model translation system.

33. The tangible computer-readable medium of claim 28, wherein the first plurality of statistical health models includes a statistical health model of the form:

$$f(x)=\beta 0+\beta 1X1+\beta 2X2+\beta 3X3+\beta bXn.$$

34. The tangible computer-readable medium of claim 28, wherein the first plurality of statistical health models includes a statistical health model that is non-linear.

35. The tangible computer-readable medium of claim 28, wherein the first plurality of statistical health models includes one or more outome predictor transforms, wherein a first of the one or more outome predictor transforms is an identity, inverse, square root, power, polynomial, exponential, logarithm, or mapping transformation.

36. The tangible computer-readable medium of claim 28, the method further comprising converting the one or more statistical health model predictors into a predictor vector.

37. The tangible computer-readable medium of claim 28, the method further comprising providing a web service via which a patient population database is passed through the statistical health model to project disease prevalences, treatment costs, and/or resource requirements.

38. The tangible computer-readable medium of claim 28, wherein the one or more user interfaces that enable one or more users to select models from the first plurality of statistical health models for execution further comprises a control via which the user can initiate the execution of all of the selected models.

39. The tangible computer-readable medium of claim 28, the method further comprising:
contracting with a research agency to provide a first statistical health model to the statistical health model translation system;
contracting with a hospital to provide the hospital with access to the first statistical health model;
storing in computer readable the first statistical health model of the contracted research agency; and
electronically providing the contracted hospital with access to the first statistical health model.

40. The tangible computer-readable medium of claim 28, the method further comprising providing access to a first statistical health model of the first plurality of statistical health models to a hospital.

41. The tangible computer-readable medium of claim 28, the method further comprising providing reformatted results obtained via the statistical health model embedded in a format that is customized, wherein the customization is based at least in part upon which end user is to receive the results.

42. The tangible computer-readable medium of claim 28, the method further comprising transmitting over a network a first output from the statistical health model to a first medical entity using a first letterhead and second output from the statistical health model to a second medical entity using a second letterhead.

43. The tangible computer-readable medium of claim 28, the method further comprising providing a first output from a first statistical health model of the first plurality of statistical health models to a first medical entity in a format as an informed consent agreement, wherein the informed consent agreement is formatted based at least in part on the identity of the first medical entity.

44. The tangible computer-readable medium of claim 28, wherein a first statistical health model of the first plurality of statistical health models is configured to perform at least one of the following:
predict a health outcome based on questionnaire responses,
assist a patient's choice of therapeutic modality based on questionnaire responses,
assess a health risk or status based on questionnaire responses.

45. The tangible computer-readable medium of claim 28, the method further comprising providing structured lists of parameters and default values to a remote system.

46. The tangible computer-readable medium of claim 28, the method further comprising obtaining values of coefficients for a first statistical health model of the first plurality of statistical health models.

47. The tangible computer-readable medium of claim 28, the method further comprising receiving default values of model parameters.

48. The tangible computer-readable medium of claim 28, the method further comprising transmitting to a remote client a response including HTML, WML, or XML formatting, including lists of the model parameters and default values.

49. The tangible computer-readable medium of claim 28, the method further comprising transmitting to the remote system information concerning selected courses of action with respect to treating a medical condition and corresponding resulting outcomes.

50. The tangible computer-readable medium of claim 28, the method further comprising receiving from the remote system patient risk assessments using health query responses and health parameter data.

51. The tangible computer-readable medium of claim 28, the method further comprising providing for display a user interface configured to receive information regarding the patient and the patient medical condition(s).

52. The tangible computer-readable medium of claim 28, the method further comprising providing a programmatic interface to receive information regarding the patient and one or more patient medical conditions.

53. The tangible computer-readable medium of claim 28, the method further comprising providing via the statistical health model translation system one or more user interfaces that enable one or more users to specify via a plurality of defined fields:
one or more limits and/or lists of possible input values for the one or more outcome predictors; and
one or more transforms for the one or more statistical health model predictors.

54. The tangible computer-readable medium of claim 28, the method further comprising providing, via the computing device, an output from a first statistical health model of the first plurality of statistical health models for display and/or returning an output from the first statistical health model of the first plurality of statistical health models via a programmatic interface.

55. A system, comprising:
a computing device;
tangible computer-readable medium having computer-executable instructions stored thereon that, if executed by a computing device, cause the computing device to perform a method comprising:
storing in computer readable memory associated with a statistical health model translation system a first plurality of statistical health models from respective sources in a plurality of different sources,
wherein at least one statistical health model in the first plurality of statistical health models from the respective sources is a medical prognostic risk stratification model and/or a medical prognostic outcomes prediction model in the form of at least one of a:
linear model,
a generalized linear model,
a cumulative multinomial model,
a generalized multinomial model,
a proportional hazard model;
providing via the statistical health model translation system one or more user interfaces including a plurality of fields that enable one or more users to specify for the at least one statistical health model:
an outcome predicted by the at least one statistical health model;
one or more outcome predictors;
a mathematical relationship between:
the outcome predicted by the at least one statistical health model, and
the one or more outcome predictors;
providing via the statistical health model translation system one or more user interfaces that enable one or more users to select models from the first plurality of statistical health models for execution;
receiving a user selection of one or more of the first plurality of statistical health models;
automatically generating data-input interfaces for collecting patient-specific predictors utilized when executing the selected one or more of the first plurality of statistical health models based at least in part on the one or more outcome predictors;
processing, via a computing device, the one or more outcome predictors and information regarding a patient received via the automatically generated data-input interfaces, where the information received via the automatically generated data-input interfaces includes one or more patient medical conditions using the selected one or more of the first plurality of statistical health models; and providing, via the computing device, an output from the selected one or more of the first plurality of statistical health models.

56. The system of claim 55, the method further comprising providing via the statistical health model translation system a user interface including a plurality of fields configured to:
receive one or more predictor coefficients; and
receive one or more predictor coefficient covariances for calculating confidence intervals.

57. The system of claim 55, wherein the first plurality of statistical health models includes a statistical health model is configured to determine a statistical outcome of a medical procedure, medical treatment or intervention, and/or medical condition with respect to the patient.

58. The method of claim 57, wherein at least one outcome includes risks associated with genetic factors or biochemical factors.

59. The system of claim 55, the method further comprising:
receiving an update to a first statistical health model of the first plurality of statistical health models from the source entity; and
storing the update in computer readable memory associated with a statistical health model translation system.

60. The system of claim 55, wherein the first plurality of statistical health models includes a statistical health model is of the form:

$$f(x)=\beta 0+\beta 1X1+\beta 2X2+\beta 3X3+\beta nXn.$$

61. The system of claim 55, wherein the first plurality of statistical health models includes a statistical health model that is non-linear.

62. The system of claim 55, wherein the first plurality of statistical health models includes one or more outome predictor transforms, wherein a first of the one or more outome predictor transforms is an identity, inverse, square root, power, polynomial, exponential, logarithm, or mapping transformation.

63. The system of claim 55, the method further comprising converting at least one of the one or more statistical health model predictors into a predictor vector.

64. The system of claim 55, the method further comprising providing a web service via which a patient population database is passed through at least a first selected plurality of the first plurality of statistical health models to project disease prevalences, treatment costs, and/or resource requirements.

65. The system of claim 55, wherein the one or more user interfaces that enable one or more users to select models from the first plurality of statistical health models for execution further comprises a control via which the user can initiate the execution of all of the selected models.

66. The system of claim 55, the method further comprising:
contracting with a research agency to provide a first statistical health model to the statistical health model translation system;
contracting with a hospital to provide the hospital with access to the first statistical health model;
storing in computer readable the first statistical health model of the contracted research agency; and
electronically providing the contracted hospital with access to the first statistical health model.

67. The system of claim 55, the method further comprising providing access to a first statistical health model of the first plurality of statistical health models to a hospital.

68. The system of claim 55, the method further comprising providing reformatted results obtained via the statistical health model embedded in a format that is customized, wherein the customization is based at least in part upon which end user is to receive the results.

69. The method of claim 1, wherein the plurality of sources includes a plurality of servers associated with one or more research agencies and wherein the first plurality of statistical health models are received electronically.

70. The method of claim 1, wherein the selected one or more of the first plurality of statistical health models includes a plurality of selected models, the method further comprising:
providing for display the results of the execution of the plurality of selected models, wherein the results of the execution of the plurality of selected models are displayed at the same time via a first output user interface;
descriptively identifying the plurality of selected models via the first output user interface; and
identifying the specified outcome that the plurality of selected models are predicting.

71. The method of claim 1, wherein the selected one or more of the first plurality of statistical health models includes a model that is linear in transformed variables.

* * * * *

UNITED STATES PATENT AND TRADEMARK OFFICE
CERTIFICATE OF CORRECTION

PATENT NO. : 7,853,456 B2
APPLICATION NO. : 11/072053
DATED : December 14, 2010
INVENTOR(S) : Gabriel Enrique Soto et al.

It is certified that error appears in the above-identified patent and that said Letters Patent is hereby corrected as shown below:

Title page, (item 56), Page 2, Col. 2, line 23, Under Other Publications, change "Joumal" to --Journal--.

Column 8, line 11-12 (Approx.), Change "Microsoft.NET" to --Microsoft .NET--.

Column 10, line 3, Change "Microsoft.NET" to --Microsoft .NET--.

Column 11, line 14-15, Change "Studio.NET™" to --Studio .NET™--.

Column 16, line 42, Change "Hosmer-Lameshow" to --Hosmer-Lemeshow--.

Column 26, line 22 (Approx.), Change "FIG. 2-9" to --FIGS. 2-9--.

Column 33, line 38 (Approx.), Change "thereof" to --thereof.--.

Column 33, line 41 (Approx.), Change "medial" to --medical--.

Column 33, line 43 (Approx.), Change "medial" to --medical--.

Column 36, line 11, Change "In" to --in--.

Column 38, line 33, Change "$x_1=1n(y)$," to --$x_1=ln(y)$,--.

Column 40, line 34 (Approx.), Change "$x'(e_x \cdot b))$" to --$x'(e_s \circ b))$--.

Column 44, line 2, In Claim 8, change "outome" to --outcome--.

Column 44, line 3, In Claim 8, change "outome" to --outcome--.

Signed and Sealed this
Twenty-first Day of June, 2011

David J. Kappos
*Director of the United States Patent and Trademark Office*

CERTIFICATE OF CORRECTION (continued)
U.S. Pat. No. 7,853,456 B2

Column 46, line 26, In Claim 30, after "model" delete "is".

Column 46, line 43 (Approx.), In Claim 33, change "βbXn." to --βnXn.--.

Column 46, line 50, In Claim 35, change "outome" to --outcome--.

Column 46, line 51, In Claim 35, change "outome" to --outcome--.

Column 49, line 3, In Claim 55, change "conditions" to --conditions,--.

Column 49, line 16, In Claim 57, after "model" delete "is".

Column 49, line 20, In Claim 58, change "method" to --system--.

Column 49, line 30, In Claim 60, after "model" delete "is".

Column 49, line 38, In Claim 62, change "outome" to --outcome--.

Column 49, line 39, In Claim 62, change "outome" to --outcome--.